S009383357B2

(12) United States Patent
Goldman et al.

(10) Patent No.: US 9,383,357 B2
(45) Date of Patent: Jul. 5, 2016

(54) BIOMARKER FOR REPLICATIVE SENESCENCE

(71) Applicant: NORTHWESTERN UNIVERSITY, Evanston, IL (US)

(72) Inventors: Robert D. Goldman, Chicago, IL (US); Takeshi Shimi, Chicago, IL (US); Stephen A. Adam, Glenview, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 14/099,444

(22) Filed: Dec. 6, 2013

(65) Prior Publication Data
US 2014/0162288 A1 Jun. 12, 2014

Related U.S. Application Data

(60) Provisional application No. 61/734,676, filed on Dec. 7, 2012.

(51) Int. Cl.
*G01N 31/00* (2006.01)
*G01N 33/53* (2006.01)
*G01N 33/569* (2006.01)

(52) U.S. Cl.
CPC ...... *G01N 33/56966* (2013.01); *G01N 2333/78* (2013.01)

(58) Field of Classification Search
CPC . A61K 45/06; A61K 2300/00; C12Q 1/6886; A01N 65/00; A01N 65/385
See application file for complete search history.

(56) References Cited

U.S. PATENT DOCUMENTS

| | | | |
|---|---|---|---|
| 4,179,337 A | 12/1979 | Davis et al. |
| 4,399,216 A | 8/1983 | Axel et al. |
| 4,740,461 A | 4/1988 | Kaufman |
| 4,816,567 A | 3/1989 | Cabilly et al. |
| 4,912,040 A | 3/1990 | Kaufman et al. |
| 4,959,455 A | 9/1990 | Clark et al. |
| 5,530,101 A | 6/1996 | Queen et al. |
| 5,585,089 A | 12/1996 | Queen et al. |
| 5,693,761 A | 12/1997 | Queen et al. |
| 5,693,762 A | 12/1997 | Queen et al. |
| 5,766,886 A | 6/1998 | Studnicka et al. |
| 5,869,619 A | 2/1999 | Studnicka et al. |
| 5,877,397 A | 3/1999 | Lonberg et al. |
| 6,075,181 A | 6/2000 | Kucherlapati et al. |
| 6,114,598 A | 9/2000 | Kucherlapati et al. |
| 6,180,370 B1 | 1/2001 | Queen et al. |

FOREIGN PATENT DOCUMENTS

| | | |
|---|---|---|
| EP | 0154316 | 9/1985 |
| EP | 0401384 | 12/1990 |
| WO | 92/16221 | 10/1992 |
| WO | 95/13312 | 5/1995 |
| WO | 95/34326 | 12/1995 |
| WO | 96/11953 | 4/1996 |
| WO | 96/19459 | 6/1996 |
| WO | 98/24893 | 6/1998 |

OTHER PUBLICATIONS

Shimi et al. (Genes & Development, vol. 25, pp. 2579-2593, Dec. 15, 2011).*
Vergnes et al. (PNAS, Jul. 13, 2004, vol. 101, No. 28, pp. 10428-10433).*
Freund et al. (Molecular Biology of the Cell, Jun. 1, 2012, vol. 23, No. 11, pp. 2066-2075).*
Neuberger et al., "Recombinant antibodies possessing novel effector functions," Nature, 1984, 312: 604-608.
Nitta et al., "Stabilization of the retinoblastoma protein by A-type nuclear lamins is required for INK4A-mediated cell cycle arrest," Molecular and cellular biology, 2006, 26: 5360-5372.
Packer and Fuehr, "Low oxygen concentration extends the lifespan of cultured human diploid cells," Nature, 1977, 267: 423-425.
Parrinello et al., "Oxygen sensitivity severely limits the replicative lifespan of murine fibroblasts," Nat Cell Biol, 2003, 5: 741-747.
Passos et al., Feedback between p21 and reactive oxygen production is necessary for cell senescence. Mol Syst Biol, 2010, 6: 347.
Pekovic et al., "Nucleoplasmic LAP2{alpha}-lamin A complexes are required to maintain a proliferative state in human fibroblasts," J Cell Biol, 2007, 176: 163-172.
Polager and Ginsberg, "p53 and E2f: partners in life and death," Nat Rev Cancer, 2009, 9: 738-748.
Queen et al., "A humanized antibody that binds to the interleukin 2 receptor," Proc. Nat'l Acad. Sci., 1989, 86:10029-10033.
Ragnauth et al., "Prelamin A acts to accelerate smooth muscle cell senescence and is a novel biomarker of human vascular aging," Circulation, 2010, 121: 2200-2210.
Rheinwald et al., "A two-stage, p16(INK4A)- and p53-dependent keratinocyte senescence mechanism that limits replicative potential independent of telomere status," Molecular and cellular biology, 2002, 22: 5157-5172.
Rodier et al., "DNA-SCARS: distinct nuclear structures inflammatory that sustain damage-induced senescence growth arrest and inflammatory cytokine secretion," J Cell Sci, 2011, 124: 68-81.
Rodriguez et al., "ERK1/2 MAP kinases promote cell cycle entry by rapid, kinase-independent disruption of retinoblastoma-lamin A complexes," J Cell Biol, 2010, 191: 967-979.
Rodriguez et al., "Increased expression of the Hutchinson-Gilford progeria syndrome truncated lamin A transcript during cell aging," European journal of human genetics : EJHG, 2009 17(7): 928-937.
Sablina et al, "The antioxidant function of the p53 tumor suppressor," Nature medicine, 2005, 11: 1306-1313.
Sahin et al., "Telomere dysfunction induces metabolic and mitochondrial compromise," Nature, 2011, 470: 359-365.

(Continued)

*Primary Examiner* — Lisa Cook
(74) *Attorney, Agent, or Firm* — Casimir Jones SC; David Staple

(57) ABSTRACT

The present invention provides biomarkers for replicative senescence. In particular, Lamin B1 is provided as a biomarker for replicative senescence.

1 Claim, 14 Drawing Sheets

(56) References Cited

OTHER PUBLICATIONS

Scaffidi and Misteli, "Reversal of the cellular phenotype in the premature aging disease Hutchinson-Gilford progeria syndrome," Nature medicine, 2005, 11: 440-445.

Scaffidi and Misteli, "Lamin A-dependent nuclear defects in human aging," Science, 2006, 312: 1059-1063.

Schefe et al., "Quantitative real-time RT-PCR data analysis: current concepts and the novel "gene expression's CT difference" formula," J Mol Med, 2006, 84: 901-910.

Schermelleh et al., "Subdiffraction multicolor imaging of the nuclear periphery with 3D structured illumination microscopy." Science, 2008, 320: 1332-1336.

Sebti, SM. Protein farnesylation: implications for normal physiology, malignant transformation, and cancer therapy. Cancer cell, 2005, 7: 297-300.

Sekharam et al., "Suppression of fibroblast cell cycle progression in G1 phase by N-acetylcysteine," Toxicology and applied pharmacology, 1998, 149: 210-216.

Serrano et al., "Oncogenic ras provokes premature cell senescence associated with accumulation of p53 and p16INK4a," Cell, 1997, 88: 593-602.

Shaulian et al., "Identification of a minimal transforming domain of p53: negative dominance through abrogation of sequence-specific DNA binding," Molecular and cellular biology, 1992, 12: 5581-5592.

Shimi et al., "The A- and B-type Nuclear Lamin Networks: Microdomains Involved in Chromatin Organization and Transcription," Genes Dev, 2008, 22: 3409-3421.

Shumaker et al., "The Highly Conserved Nuclear Lamin Ig-fold Binds to PCNA: Its Role in DNA Replication," J Cell Biol, 2008, 181: 269-280.

Spanier et al., "Resveratrol reduces endothelial oxidative stress by modulating the gene expression of superoxide dismutase 1 (SOD1), glutathione peroxidase 1 (GPx1) and NADPH oxidase subunit (Nox4)," J Physiol Pharmacol, 2009, 60 Suppl 4:111-116.

Spann et al., "Alteration of nuclear lamin organization inhibits RNA polymerase II- dependent transcription," J Cell Biol, 2002, 156: 603-608.

Spann et al., "Disruption of nuclear lamin organization alters the distribution of replication factors and inhibits DNA synthesis," J Cell Biol, 1997, 136: 1201-1212.

Sullivan et al., "Loss of A-type lamin expression compromises nuclear envelope integrity leading to muscular dystrophy," J Cell Biol, 1999, 147: 913-920.

Taimen et al., A progeria mutation reveals functions for lamin A in nuclear assembly, architecture, and chromosome organization. Proceedings of the National Academy of Sciences of the United States of America, 2009, 106: 20788-20793.

Takeda et al., "Construction of chimaeric processed immunoglobulin genes containing mouse variable and human constant region sequences," Nature, 1985, 314:452-454.

Tomizuka et al., "Double trans-chromosomic mice: Maintenance of two individual human chromosome fragments containing Ig heavy and κ loci and expression of fully human antibodies," Proc. Nat'l Acad. Sci. USA, 2000, 97:722-727.

Ukekawa et al., "Accumulation of multiple forms of lamin A with down-regulation of FACE-1 suppresses growth in senescent human cells," Genes to cells : devoted to molecular & cellular mechanisms, 2007, 12: 397-406.

Varani et al., "A Novel Benzodiazepine Selectivity Inhibits Keratinocyte Proliferation and Reduces Retinoid-Induced Epidermal Hyperplasia in Organ-Cultured Human Skin," The Journal of Pharmacology and Experimental Therapeutics, 2005 313: 56-63.

Vergnes et al., "Lamin B1 is required for mouse development and nuclear integrity," Proceedings of the National Academy of Sciences of the United States of America, 2004, 101: 10428-10433.

Weinberg et al., "Mitochondrial metabolism and ROS generation are essential for Krasmediated tumorigenicity," Proceedings of the National Academy of Sciences of the United States of America, 2010, 107: 8788-8793.

Wright et al., "Cellular senescence as a tumor-protection mechanism: the essential role of counting," Curr Opin Genet Dev, 2001, 11:98-103.

Yang et al., "An absence of both lamin B1 and lamin B2 in keratinocytes has no effect on cell proliferation or the development of skin and hair," Hum Mol Genet, 2011, 20: 3537-3544.

Yang and Hekimi, "A mitochondrial superoxide signal triggers increased longevity in Caenorhabditis elegans," PLoS biology, 2010, 8: e1000556.

Yuan et al., "Statistical analysis of real-time PCR data," BMC Bioinformatics, 2006, 7(85): 1-12.

Havens et al., "Regulation of late G1/S phase transition and APC Cdh1 by reactive oxygen species," Molecular and cellular biology, 2006, 26: 4701-4711.

Hoogenboom, H. "Overview of Antibody Phage-Display Technology and Its Applications," Methods in Molecular Biology: Antibody Phage Display: Methods and Protocols (2002) 178:1-37.

Hopp and Woods, "Prediction of protein antigenic determinants from amino acid sequences," Proc. National Acad. Sci. USA, 1981, 78(6):3824-3828.

Huang, et al., "Accelerated telomere shortening and replicative senescence in human fibroblasts overexpressing mutant and wild-type lamin A," Experimental cell research, 2008, 314: 82-91.

Hudson et al., "Engineered antibodies," Nature Med., 2003, 9:129-134.

Hussain et al., "p53-induced up-regulation of MnSOD and GPx but not catalase increases oxidative stress and apoptosis," Cancer research, 2004,64: 2350-2356.

Ibarra et al., "Excess MCM proteins protect human cells from replicative stress by licensing backup origins of replication," Proceedings of the National Academy of Sciences of the United States of America, 2008, 105: 8956-8961.

Jakobovits, A., "Production of fully human antibodies by transgenic mice," Curr. Opin. Biotechnol, 1995, 6:561-566.

Jakobovits et al., "Germ-line transmission and expression of a human-derived yeast artificial chromosome," Nature, 1993, 362:255-258.

Johnson et al., "A-type lamins regulate retinoblastoma protein function by promoting subnuclear localization and preventing proteasomal degradation," Proceedings of the National Academy of Sciences of the United States of America, 2004,101: 9677-9682.

Jones, N.C. "Transformation by the human adenoviruses," Seminars in Cancer Biol, 1990, 1: 425-435.

Kandert et al., "Nesprin-2 giant safeguards nuclear envelope architecture in LMNA S143F progeria cells," Hum Mol Genet, 2007, 16: 2944-2959.

Kandert et al., "Impaired nuclear functions lead to increased senescence and inefficient differentiation in human myoblasts with a dominant p.R545C mutation in the LMNA gene," European journal of cell biology, 2009, 88: 593-608.

Kang et al., "Antibody redesign by chain shuffling from random combinatorial immunoglobulin libraries," Proc. Nat'l Acad. Sci., 1991, USA 88:11120-11123.

Kapinos et al., "Characterization of the head-to-tail overlap complexes formed by human lamin A, B1 and B2 "half-minilamin" dimers," J Mol Biol, 2010, 396: 719-731.

Karlsson et al., "Kinetic analysis of monoclonal antibody-antigen interactions with a new biosensor based analytical system," J. Immunol. Methods, 1991, 145:229-240.

Kennedy et. al., "Nuclear organization of DNA replication in primary mammalian cells," Genes Dev, 2000,14: 2855-2868.

Kohler et al., "Continuous cultures of fused cells secreting anitbody of predefined specificity," Nature, 1975, 256:495-497.

Kosak et al., "Subnuclear compartmentalization of immunoglobulin loci during lymphocyte development," Science, 2002, 296: 158-162.

Kumaran et al., "A genetic locus targeted to the nuclear periphery in living cells maintains its transcriptional competence," J Cell Biol, 2008, 180: 51-65.

Kyte and Doolittle, "A Simple Method for Displaying the Hydropathic Character of a Protein," J. Mol. Biol., 1982 157:105-132.

Laemmli UK. 1970. Cleavage of structural proteins during the assembly of the head of bacteriophage T4. Nature 227: 680-685.

(56) References Cited

OTHER PUBLICATIONS

Lebedeva et al., "Loss of p53 causes mitochondrial DNA depletion and altered mitochondrial reactive oxygen species homeostasis," Biochim Biophys Acta, 2009, 1787: 328-334.
Lee et al., "Inhibition of respiration extends C. elegans life span via reactive oxygen species that increase HIF-1 activity," Curr Biol, 2010, 20: 2131-2136.
Little et al., "Of mice and men: hybridoma and recombinant antibodies," Immunol. Today, 2000, 21(8):364-370.
Liu et al., "Recapitulation of premature ageing with iPSCs from Hutchinson-Gilford progeria syndrome," Nature, 2011, 472: 221-225.
Lonberg et al., "Human antibodies from transgenic mice," Int Rev. Immunol., 1995, 13:65-93.
Macip et al., "Inhibition of p21-mediated ROS accumulation can rescue p21-induced senescence," The EMBO Journal, 2002, 21: 2180-2188.
Malhas et al., "Lamin B1 controls oxidative stress responses via Oct-1," J Cell Biol, 2009, 184:45-55.
Malik et al., "Polyethylene glycol (PEG)-modified granulocyte-macrophage colony-stimulating factor (GM-CSF) with conserved biological activity," Exp. Hematol., 1992, 20:1028-1035.
Malmqvist, M. "Surface plasmon resonance for detection and measurement of antibody-antigen affinity and kinetics," Curr. Opin. Immunol., 1993, 5:282-286.
Mancini et al., "The retinoblastoma gene product is a cell cycle-dependent, nuclear matrix-associated protein," Proceedings of the National Academy of Sciences of the United States of America, 1994, 91: 418-422.
Marks et al., "By-passing immunization: building high affinity human antibodies by chain shuffling," Biotechnology, 1992, 10:779-83.
Marks, et al., "By-passing Immunization: Human Antibodies from V-gene Libraries Displayed on Phage," J. Mol. Biol., 1991, 222: 581-597.
Maske et al., "A carboxyl-terminal interaction of lamin B1 is dependent on the CAAX endoprotease Rce1 and carboxymethylation," J Cell Biol, 2003, 162: 1223-1232.
Matoba et al., "p53 Regulates Mitochondrial Respiration," Science, 2006, 312: 1650-1653.
McCafferty et al., Antibody Engineering: A Practical Approach, 1996, Oxford University Press, Table of Contents only.
McClintock et al., "Hutchinson-Gilford progeria mutant lamin A primarily targets human vascular cells as detected by an anti-Lamin A G608G antibody," Proceedings of the National Academy of Sciences of the United States of America, 2006, 103: 2154-2159.
McClintock et al, "The mutant form of lamin A that causes Hutchinson-Gilford progeria is a biomarker of cellular aging in human skin," PloS one, 2007, 2: e1269.
Meaburn et al., "Primary laminopathy fibroblasts display altered genome organization and apoptosis," Aging Cell, 2007, 6(2): 139-53.
Mendez et al., "Functional transplant of megabase human immunoglobulin loci recapitulates human antibody response in mice," Nat. Genet., 1997, 15:146-156.
Moir et al., "Dynamic properties of nuclear lamins: lamin B is associated with sites of DNA replication," J Cell Biol, 1994, 125: 1201-1212.
Moir et al., "The Dynamic Properties and Possible Functions of Nuclear Lamins," Int Rev Cytol, 1995, 162B:141-182.
Moir et al., "Disruption of nuclear lamin organization blocks the elongation phase of DNA replication," J Cell Biol, 2000, 149: 1179-1192.
Moir et al., "Nuclear Lamins A and B1. Different pathways of assembly during nuclear envelope formation in living cells," J Cell Biol, 2000, 151: 1155-1168.
Moiseeva et al., "Retinoblastoma-independent regulation of cell proliferation and senescence by the p53-p21 axis in lamin A/C-depleted cells," Aging cell, 2011,10: 789-797.

Morrison et al., "Chimeric human antibody molecules: Mouse antigen-binding domains with human constant region domains," Proc. Nat'l Acad. Sci, 1984, 81: 6851-6855.
Mounkes et al., "The laminopathies: nuclear structure meets disease," Curr Opin Genet Dev, 2003, 13: 223-230.
Narita et al., "A Novel Role for High-Mobility Group A Proteins in Cellular Senescence and Heterochromatin Formation," Cell, 2006, 126: 503-514.
Narita et al., "Rb-mediated heterochromatin formation and silencing of E2F target genes during cellular senescence," Cell, 2003, 113: 703-716.
Aebi et al., "The nuclear lamina is a meshwork of intermediate-type filaments," Nature, 1986, 323: 560-564.
Atamna et al., "N-t-butyl hydroxylamine, a hydrolysis product of alpha-phenyl-N-t-butyl nitrone, is more potent in delaying senescence in human lung fibroblasts," The Journal of biological chemistry, 2000, 275: 6741-6748.
Ausubel et al. (1989) Current Protocols in Molecular Biology Ch. 11.15 (John Wiley & Sons, NY), Table of Contents Only.
Ausubel et al., "Immunoblotting and Immunodetection,"Current Protocols in Molecular Biology, 2008, Ch. 10.8 (John Wiley & Sons, NY).
Behrend et al., "Manganese superoxide dismutase induces p53-dependent senescence in colorectal cancer cells," Molecular and cellular biology, 2005, 25: 7758-7769.
Bell et al., "Mitochondrial reactive oxygen species trigger hypoxia-inducible factor-dependent extension of the replicative life span during hypoxia," Molecular and cellular biology, 2007, 27: 5737-5745.
Blake et al., "Metal Binding Properties of a Monoclonal Antibody Directed toward Metal-Chelate Complexes," J. Biol. Chem., 1996, 271 (44):27677-27685.
Boder and Wittrup, "Yeast surface display for screening cobinatorial polypeptide libraries," Nature Biotechnology, 1997, 15:553-557.
Boder et al., "Directed evolution of anitbody fragments with monovalent femtomolar antigen-binding affinity," Proc. Nat'l Acad. Sci., 2000, 97:10701-10705.
Borreback et al., "Human monoclonal antibodies produced by primary in vitro immunization of peripheral blood lymphocytes," Proc. Nat'l. Acad. Sci., 1988, 85:3995-3999.
Boyer et al., "E7 protein of human papilloma virus-16 induces degradation of retinoblastoma protein through the ubiquitin-proteasome pathway," Cancer research, 1996, 56: 4620-4624.
Brekke et al., "Therapeutic antibodies for human diseases at the dawn of the twenty-first century," Nature Reviews Drug, 2003, 2:52-62.
Burkhart and Sage, "Cellular mechanisms of tumour suppression by the retinoblastoma gene," Nat Rev Cancer, 2008, 8: 671-682.
Campisi et al., "Cellular senescence: when bad things happen to good cells," Nat Rev Mol Cell Biol, 2007, 8: 729-740.
Cao et al., "Progerin and telomere dysfunction collaborate to trigger cellular senescence in normal human fibroblasts," The Journal of clinical investigation, 2011,121(7): 2833-2844.
Carpenter et al., "Response of Dogs to Repeated Intravenous Injection of Polyethylene Glycol 4000 with Notes on Excretion and Sensitization," Toxicol. Appl. Pharmacol., 1971, 18, 35-40.
Chou and Fasman, "Empirical Predictions of Protein Conformation," Ann. Rev. Biochem., 1978, 47:251-276.
Clackson et al., "Making Antibody Fragments Using Phage Display Libraries," Nature 352: 624-628 (1991).
Coffinier et al., "Abnormal development of the cerebral cortex and cerebellum in the setting of lamin B2 deficiency," Proceedings of the National Academy of Sciences of the United States of America, 2010,107: 5076-5081.
Coffinier et al., "Deficiencies in lamin B1 and lamin B2 cause neurodevelopmental defects and distinct nuclear shape abnormalities in neurons," Molecular biology of the cell, 2011, 22(23):4683-93.
Coller, H. "What's taking so long? S-phase entry from quiescence versus proliferation," Nat Rev Mol Cell Biol, 2007, 8:667-670.
Corrigan and Huang, "A Basic microcomputer program for plotting the secondary structure of proteins," Comput. Programs Biomed., 1982, 15:163-168.
Crameri et al., "Construction and evolution of antibody-phage libraries by DNA shuffling," 1996 Nature Med. 2:100-102.

(56) References Cited

OTHER PUBLICATIONS d'Adda dl Fagagna et al., "A DNA damage checkpoint response in telomere-initiated senescence," Nature, 2003 426: 194-198.

DeCaprio et al., "The product of the retinoblastoma susceptibility gene has properties of a cell cycle regulatory element," 1989, Cell 58: 1085-1095.

Dechat et al., "Nuclear Lamins: Major Factors in the Structural Organization and Function of the Nucleus and Chromatin," Genes and Development, 2008, 22: 832-853.

Deng et al- "The ability of E1A to rescue ras-induced premature senescence and confer transformation relies on inactivation of both p300/CBP and Rb family proteins," Cancer research, 2005,65: 8298-8307.

Dimri et al., "A biomarker that identifies senescent human cells in culture and in aging skin in vivo," Proceedings of the National Academy of Sciences of the United States of America, 1995,92: 9363-9367.

Dooley et al., "Imaging dynamic redox changes in mammalian cells with green fluorescent protein indicators," The Journal of biological chemistry, 2004,279: 22284-22293.

Dorner et al.,"Nucleoplasmic lamins and their interaction partners, LAP2alpha, Rb, and BAF, in transcriptional regulation," The Febs Journal, 2007,274: 1362-1373.

Drake et al., "Characterizing high-affinity antigen/antibody complexes by kinetic- and equilibrium-based methods," Anal. Biochem, 2004, 328:35-43.

Fermer et al., "Specificity Rescue and Affinity Maturation of a Low-Affinity IgM Antibody against Pro-Gastrin-Releasing Peptide using Phage Display and DNA Shuffling," Tumor Biology, 2004, 25:7-13.

Finkel et al., "Oxidants, oxidative stress and the biology of ageing," Nature, 2000,408: 239-247.

Fishwild et al., "High-avidity human IgGK monoclonal antibodies from a novel strain of minilocus transgenic mice," Nat. Biotechnol., 1996, 14:845-851.

Foote et al., "Breaking the affinity ceiling for antibodies and T cell receptors," Proc. Nat'l Acad. Sci., 2000, USA 97:10679-10681.

Forsyth et al., "Developmental differences in the immortalization of lung fibroblasts by telomerase," Aging cell, 2003, 2: 235-243.

Francis et al., "Focus on Growth Factors," Mediscript, Mountain Court, Freiem Barnet Lane, London, 1992, 3(2): 4-10.

Gjoerup et al., "Surveillance mechanism linking Bub1 loss to the p53 pathway," Proceedings of the National Academy of Sciences of the United States of America, 2007,104: 8334-8339.

Goldberg et al., "Methods for measurement of antibody/antigen affinity based on ELISA and RIA," Curr. Opin. Immunol., 1993, 5:278-281.

Goldman et al., "Accumulation of mutant lamin A causes progressive changes in nuclear architecture in Hutchinson-Gilford progeria syndrome," Proceedings of the National Academy of Sciences of the United States of America, 2004,101: 8963-8968.

Gonzalez-Suarez et al., "Novel roles for A-type lamins in telomere biology and the DNA damage response pathway," EMBO Journal, 2009, 28: 2414-2427.

Green, LL. "Antibody engineering via genetic engineering of the mouse: XenoMouse strains are a vehicle for the facile generation of therapeutic human monoclonal antibodies," J. Immunol. Methods, 1999, 231:11-23.

Guelen et al., "Domain organization of human chromosomes revealed by mapping of nuclear lamina interactions," Nature, 2008,453: 948-951.

Guzy et al., "Loss of the SdhB, but Not the SdhA, subunit of complex II triggers reactive oxygen species-dependent hypoxia-inducible factor activation and tumorigenesis," Molecular and cellular biology, 2008, 28: 718-731.

Hagen et al., "Mitochondrial decay in hepatocytes from old rats: membrane potential declines, heterogeneity and oxidants increase," Proceedings of the National Academy of Sciences of the United States of America, 1997, 94: 3064-3069.

Hallstrom, et al., "An E2F1-dependent gene expression program that determines the balance between proliferation and cell death," Cancer cell, 2008, 13: 11-22.

Hanes et al., "Ribosome display efficiently selects and evloves high-affinity antibodies in vitro from immune libraries," Proc. Nat'l Acad. Sci., USA, 1998, 95:14130-14135.

Hanson et al., "Investigating mitochondrial redox potential with redox-sensitive green fluorescent protein indicators," The Journal of biological chemistry, 2004, 279: 13044-13053.

Harley et al., "Telomeres shorten during ageing of human fibroblasts," Nature, 1990,345: 458-460.

Harlow, et al. Antibodies: A Laboratory Manual Ch. 6, (Cold Spring Harbor Laboratory, Cold Spring Harbor, N.Y.) 1988.

\* cited by examiner

SEQUENCE LISTING

<160> NUMBER OF SEQ ID NOS: 2

<210> SEQ ID NO 1
<211> LENGTH: 19
<212> TYPE: DNA
<213> ORGANISM: Artificial sequence
<220> FEATURE:
<223> OTHER INFORMATION: Synthetic

<400> SEQUENCE: 1
ttcccgtgca accagtttg                                              19

<210> SEQ ID NO 2
<211> LENGTH: 20
<212> TYPE: DNA
<213> ORGANISM: Artificial sequence -continued

```
<220> FEATURE:
<223> OTHER INFORMATION: Synthetic

<400> SEQUENCE: 2
ttcacctcgc acttctcgaa                                              20
```

BIOMARKER FOR REPLICATIVE SENESCENCE

CROSS-REFERENCE TO RELATED APPLICATIONS

The present application claims priority to U.S. Provisional Patent Application Ser. No. 61/734,676 filed Dec. 7, 2012; which is hereby incorporated by reference in its entirety.

STATEMENT REGARDING FEDERAL FUNDING

This invention was made with government support under 5 R01 CA 031760-29 awarded by the National Institutes of Health. The government has certain rights in the invention.

FIELD

The present invention provides biomarkers for replicative senescence. In particular, Lamin B1 is provided as a biomarker for replicative senescence.

BACKGROUND

The nuclear lamina is closely apposed to the inner membrane of the nuclear envelope (NE) and contributes to the size, shape and mechanical stability of the nucleus. The major structural proteins of the lamina are the A- and B-type nuclear lamins, comprised of lamins A and C (LA, LC), and lamins B1 (LB1) and B2 (LB2). Although the major fraction of lamins is found in the lamina, they are also located throughout the nucleoplasm (Moir et al. 2000b; Shimi et al. 2008; herein incorporated by reference in their entireties). LA and LC are derived from a single gene (LMNA) by alternative splicing and are expressed only in differentiated cells. LB1 and LB2 are encoded by LMNB1 and LMNB2, respectively, and at least one of the B-type lamins is expressed in all cells throughout development (Dechat et al. 2008; herein incorporated by reference in its entirety). There is growing evidence that the nuclear lamins play important roles in the anchorage of peripheral elements of chromatin, in regulating the organization of chromosome territories and in gene expression (Kosak et al. 2002; Guelen et al. 2008; Kumaran and Spector 2008; Shimi et al. 2008; herein incorporated by reference in their entireties). The lamins have also been shown to play important roles in DNA replication and repair, RNA polymerase II transcription, and the epigenetic control of chromatin remodeling (Moir et al. 2000a; Spann et al. 2002; Shimi et al. 2008; Shumaker et al. 2008; herein incorporated by reference in their entireties).

All lamins share a common structure with a conserved α-helical central rod domain flanked by globular head and tail domains (Dechat et al. 2008; herein incorporated by reference in its entirety). The central rod domains of two lamins dimerize into in-parallel and in-register coiled-coil structures which then interact head-to-tail to form long protofilaments. Lateral interactions between anti-parallel protofilaments, with influence from the head and tail domains, form the higher order structures found in the nucleus (Kapinos et al. 2010; herein incorporated by reference in its entirety). Using electron microscopy, the lamina in *Xenopus* oocytes appears as a meshwork of ~10 to 15 nm filaments (Aebi et al. 1986; herein incorporated by reference in its entirety). Higher order LB1 structures organized into meshworks have been seen in mouse cells by immunofluorescence (Schermelleh et al. 2008; herein incorporated by reference in its entirety). Additionally, A- and B-type lamin fibrils form interacting meshworks within the lamina in HeLa cells (Shimi et al. 2008; herein incorporated by reference in its entirety). Support for these interactions has been derived from silencing LB1 expression using shRNA. The loss of LB1 leads to a dramatic increase in the size of the LA/C meshwork and induces the formation of LA/C-rich and LB2-deficient NE blebs. These findings demonstrate that LB1 plays an essential role in maintaining normal LA/C and LB2 meshwork structures (Shimi et al. 2008; herein incorporated by reference in its entirety). Furthermore, the LA/C-rich NE blebs induced by LB1 silencing contain gene rich chromatin with low transcriptional activity even though the activated form of RNA polymerase II (Pol IIo) is enriched in these regions. This suggests that both A- and B-type lamins are required for properly regulating gene expression (Shimi et al. 2008). Interestingly, the nuclei of cells from patients with diseases caused by mutations in LMNA, such as Hutchinson-Gilford Progeria and Emery-Dreifuss Muscular Dystrophy type 2, frequently exhibit alterations in the structural organization of the A- and B-type lamin meshworks and contain NE blebs similar to those induced by silencing LB1 expression (Goldman et al. 2004; Meaburn et al. 2007; Shimi et al. 2008; Taimen et al. 2009; herein incorporated by reference in their entireties).

The detection of senescent cells is an important parameter for all types of biomedical research studies as well as in pathology, aging and cancer.

SUMMARY

In some embodiments, the present invention provides compositions comprising specific antibodies directed against nuclear Lamin B1 (LB1). In some embodiments, the antibodies bind to lamin B1 but not to other nuclear lamins. In some embodiments, the antibodies do not bind lamin B2 and lamin A/C. In some embodiments, the antibodies are markers for replicative senescence.

In some embodiments, the present invention provides methods to detect senescent cells comprising detecting the presence, absence, and/or level of lamin B1. In some embodiments, the present invention provides methods to detect senescent cells in a population comprising contacting said cells with a primary antibody comprising a specific antibody directed against nuclear Lamin B1 (LB1). In some embodiments, the antibodies bind to lamin B1 but not to other nuclear lamins. In some embodiments, antibodies do not bind lamin B2 and lamin A/C. In some embodiments, the cells are chemically fixed and processed for indirect immunofluorescence. In some embodiments, binding of said antibodies to nuclear Lamin B1 indicates replicative senescence. In some embodiments, methods further comprise binding a detectable secondary antibody to the antibodies directed against nuclear Lamin B1.

In some embodiments, the present invention provides methods of inducing senescence in cells by silencing Lamin B1. In some embodiments, Lamin B1 neutralizing antibodies are administered to cells to silence Lamin B1 and induce senescence.

In some embodiments, the present invention provides methods of increasing the proliferation rate of cells comprising increasing expression of, and/or the cellular concentration of Lamin B1.

DEFINITIONS

Figure 1:
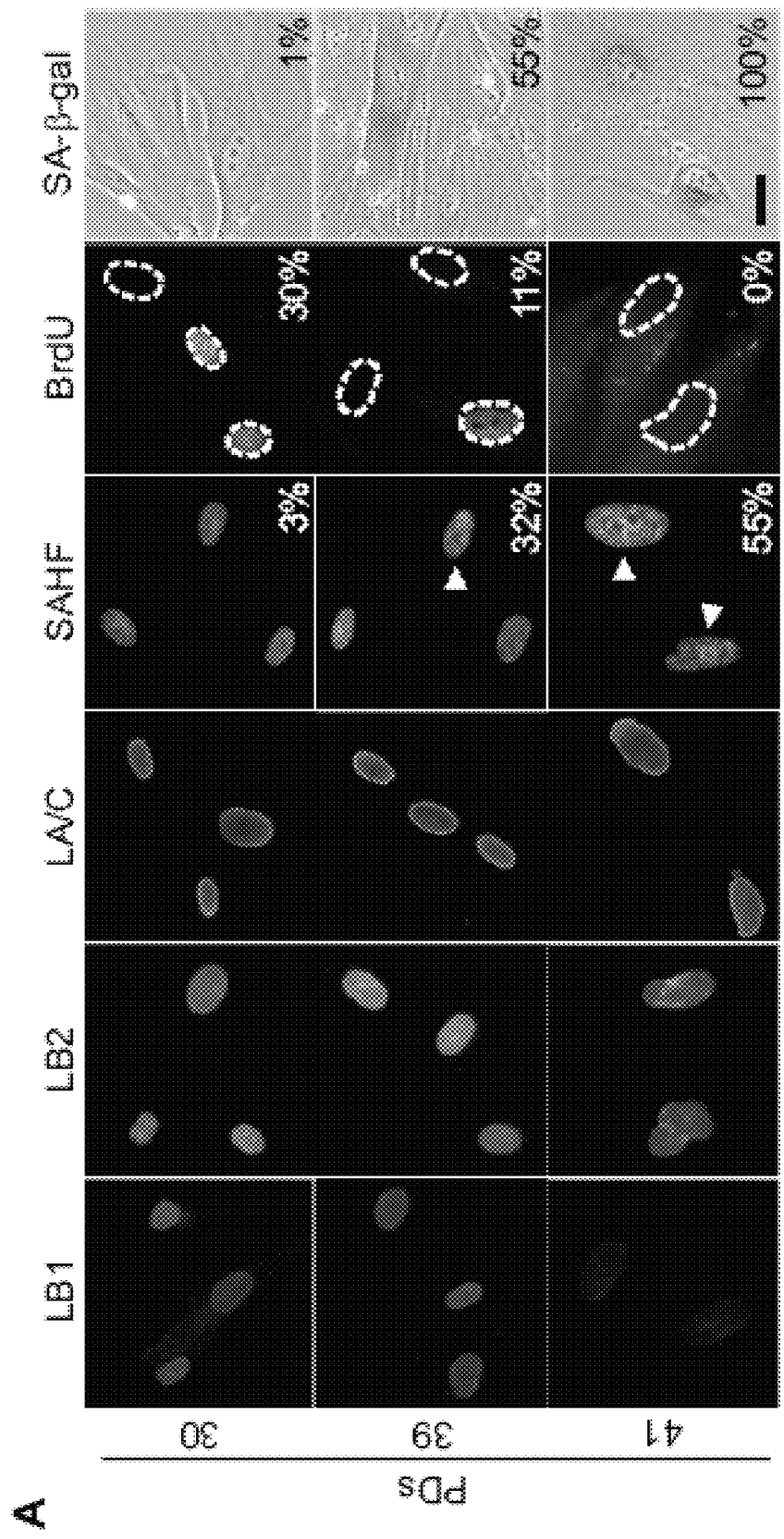
FIG. 1 shows loss of LB1 is associated with senescence in WI-38 cells. (A) The nuclear localization of LB1, LB2, and LA/C in WI-38 cells were examined by immunofluorescence at PDs 30, 39 and 41. Senescent cells were identified by Hoechst staining of SAHFs, SA-β-gal activity, and BrdU incorporation. The numbers on the panels indicate the percentage of cells positive for the marker indicated at the top of the column. Scale bar=10 µm. (B) LB1 protein levels were assayed by western blotting after culture from PD30 to PD41 (top panel) and quantified (see Materials and Methods). The relationship between PDs (black) and the amount of LB1 (red) is shown (bottom graph). (C) The expression levels of LB1, LB2, and LA/C were examined at PDs 30, 41 and in quiescent cells by immunoblotting. It should be noted that neither pre-LA nor LAΔ50 progerin were detected in the senescent cells (see Discussion). Actin was used as a loading control. (D) LMNB1, LMNB2, and LMNA mRNA levels were determined by quantitative PCR at PD30, 39 and 41. The error bars represent standard error of the mean (n=6).
Figure 1:
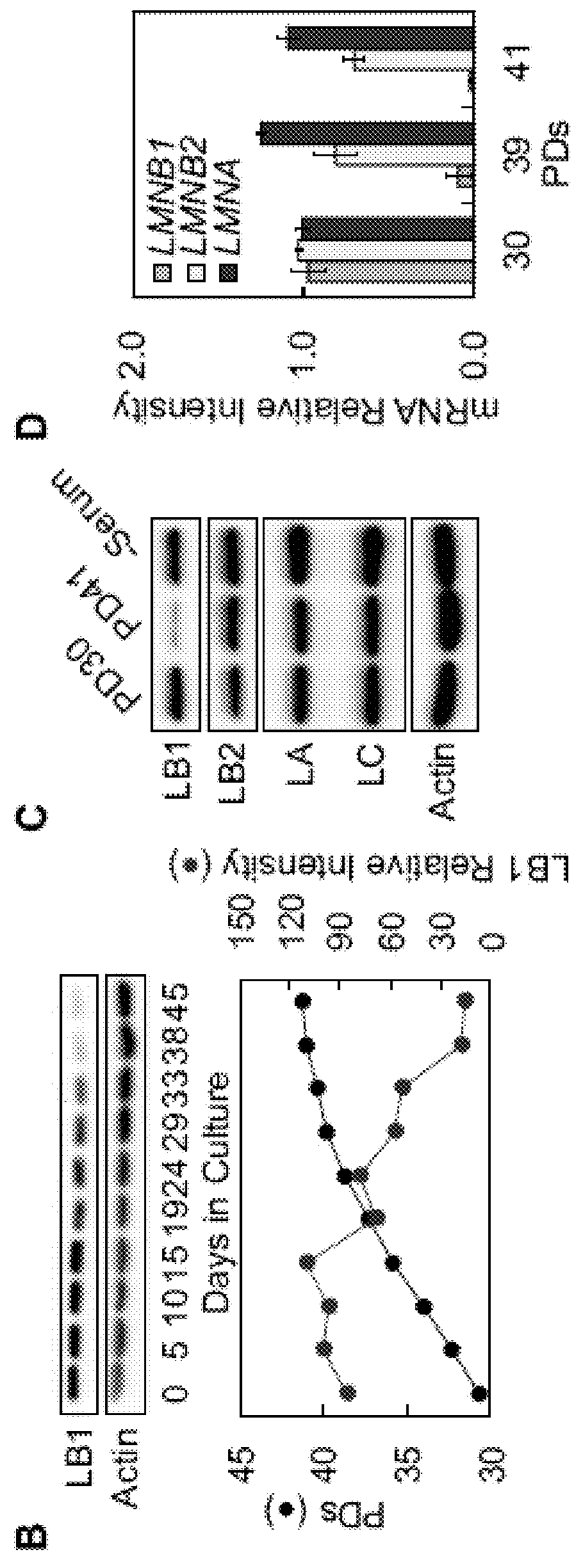

The terms "polypeptide," "peptide," and "protein" are used herein to refer to a polymer of amino acid residues. The terms apply to amino acid polymers containing naturally occurring amino acids as well as amino acid polymers in which one or more amino acid residues is an artificial chemical analogue of a corresponding naturally occurring amino acid. The amino acid polymers can be of any length.

The term "antibody," as used herein, refers to an intact antibody or a fragment of an antibody that competes with the intact antibody for antigen binding. Antibody fragments include, but are not limited to, Fab, Fab', F(ab').sub.2, Fv, scFv, Fd, diabodies, and other antibody fragments that retain at least a portion of the variable region of an intact antibody. See, e.g., Hudson et al. (2003) Nature Med. 9:129-134; herein incorporated by reference in its entirety. In certain embodiments, antibody fragments are produced by enzymatic or chemical cleavage of intact antibodies. In certain embodiments, antibody fragments are produced by recombinant DNA techniques.

The term "neutralizing antibody" or "antibody that neutralizes" refers to an antibody that reduces at least one activity of a polypeptide comprising the epitope to which the antibody specifically binds. In certain embodiments, a neutralizing antibody reduces an activity in vitro and/or in vivo.

The term "native polypeptide" refers to a naturally occurring polypeptide. The term "native antibody" refers to a naturally occurring antibody.

The term "monoclonal antibody" refers to an antibody from a substantially homogeneous population of antibodies that specifically bind to the same epitope. In certain embodiments, a monoclonal antibody is secreted by a hybridoma. In certain such embodiments, a hybridoma is produced according to certain methods known to those skilled in the art. See, e.g., Kohler and Milstein (1975) Nature, 256: 495-499; herein incorporated by reference in its entirety). In certain embodiments, a monoclonal antibody is produced using recombinant DNA methods (see, e.g., U.S. Pat. No. 4,816,567; herein incorporated by reference in its entirety). In certain embodiments, a monoclonal antibody refers to an antibody fragment isolated from a phage display library (see, e.g., Clackson et al. (1991) Nature 352: 624-628, and Marks et al. (1991) J. Mol. Biol. 222: 581-597; herein incorporated by reference in their entireties). For various other monoclonal antibody production techniques, see, e.g., Harlow and Lane (1988) Antibodies: A Laboratory Manual (Cold Spring Harbor Laboratory, Cold Spring Harbor, N.Y.; herein incorporated by reference in its entirety).

A "chimeric" antibody refers to an antibody made up of components from at least two different sources. In certain embodiments, a chimeric antibody comprises a portion of an antibody derived from a first species fused to another molecule, e.g., a portion of an antibody derived from a second species. In certain such embodiments, a chimeric antibody comprises a portion of an antibody derived from a non-human animal fused to a portion of an antibody derived from a human. In certain such embodiments, a chimeric antibody comprises all or a portion of a variable region of an antibody derived from a non-human animal fused to a constant region of an antibody derived from a human.

A "humanized" antibody refers to a non-human antibody that has been modified so that it more closely matches (in amino acid sequence) a human antibody. A humanized antibody is thus a type of chimeric antibody. In certain embodiments, amino acid residues outside of the antigen binding residues of the variable region of the non-human antibody are modified. In certain embodiments, a humanized antibody is constructed by replacing all or a portion of a complementarity determining region (CDR) of a human antibody with all or a portion of a CDR from another antibody, such as a non-human antibody, having the desired antigen binding specificity. In certain embodiments, a humanized antibody comprises variable regions in which all or substantially all of the CDRs correspond to CDRs of a non-human antibody and all or substantially all of the framework regions (FRs) correspond to FRs of a human antibody. In certain such embodiments, a humanized antibody further comprises a constant region (Fc) of a human antibody.

The term "human antibody" refers to a monoclonal antibody that contains human antibody sequences and does not contain antibody sequences from a non-human animal. In certain embodiments, a human antibody may contain synthetic sequences not found in native antibodies. The term is not limited by the manner in which the antibodies are made. For example, in various embodiments, a human antibody may be made in a transgenic mouse, by phage display, by human B-lymphocytes, or by recombinant methods.

The term "antigen-binding site" refers to a portion of an antibody capable of specifically binding an antigen. In certain embodiments, an antigen-binding site is provided by one or more antibody variable regions.

The term "epitope" refers to any polypeptide determinant capable of specifically binding to an immunoglobulin or a T-cell receptor. In certain embodiments, an epitope is a region of an antigen that is specifically bound by an antibody. In certain embodiments, an epitope may include chemically active surface groupings of molecules such as amino acids, sugar side chains, phosphoryl, or sulfonyl groups. In certain embodiments, an epitope may have specific three dimensional structural characteristics (e.g., a "conformational" epitope) and/or specific charge characteristics.

An epitope is defined as "the same" as another epitope if a particular antibody specifically binds to both epitopes. In certain embodiments, polypeptides having different primary amino acid sequences may comprise epitopes that are the same. In certain embodiments, epitopes that are the same may have different primary amino acid sequences. Different antibodies are said to bind to the same epitope if they compete for specific binding to that epitope.

An antibody "specifically binds" an antigen when it preferentially recognizes the antigen in a complex mixture of proteins and/or macromolecules. In certain embodiments, an antibody comprises an antigen-binding site that specifically binds to a particular epitope. In certain such embodiments, the antibody is capable of binding different antigens so long as the different antigens comprise that particular epitope. In certain instances, for example, homologous proteins from different species may comprise the same epitope. In certain embodiments, an antibody is said to specifically bind an antigen when the dissociation constant ($K_D$) is <1 µM, in certain embodiments, when the dissociation constant is <100 nM, and in certain embodiments, when the dissociation constant is <10 nM.

DETAILED DESCRIPTION

Experiments conducted during development of embodiments of the present invention demonstrate that nuclear lamin B1 is selectively lost during cellular senescence in human diploid cells. Loss of nuclear lamin B1 was detected in situ by the use of a specific Lamin B1 antibody. The detection of senescent cells is an important parameter for all types of biomedical research studies as well as in pathology, aging and cancer. In some embodiments, compositions and methods are provided for staining senescent cells with an antibody that only stains nuclei in normal cells, but is lost in senescent cells. In some embodiments, methods and compositions provide an advantage over other techniques, based upon the difficulty of applying other more time consuming methods such as BrdU incorporation, detection of Senescence Associated Heterochromatin Foci (SAHF) or the detection of senescence associated β-galactosidase. In some embodiments, detection systems are provided that can readily be applied to animal and human tissues and can further be developed to speed up the processing of cells and tissues by using directly conjugated antibodies.

In some embodiments, the present invention provides specific antibodies directed against nuclear Lamin B1 (LB1). In some embodiments, antibodies distinguish between lamin B1 and the other nuclear lamins, lamin B2, and lamin A/C. In some embodiments, in order to detect senescent cells in a population, cells are chemically fixed and processed for indirect immunofluorescence. In some embodiments, the primary LB1 specific antibody is followed by fluorophore-tagged or horseradish peroxidase tagged secondary antibodies. In some embodiments, the entire procedure requires 2 hrs or less and senescent cells are readily detected in readily available conventional fluorescence microscopes. In contrast the BrdU procedure requires anywhere from 5-8 hr and is extremely difficult to employ in tissues. The detection of senescence associated β-galactosidase takes 6-12 hrs and is difficult to detect above background (it is a more subjective assay). The detection of senescence associated heterochromatic foci requires specific senescence pathways but is not applicable to all pathways leading to senescence. Experiments conducted during development of embodiments of the present invention demonstrate that several pathways leading to senescence are correlated with the loss of lamin B1.

The results of experiments conducted during development of embodiments of the present invention demonstrate that LB1 expression in WI-38 cells decreases during cellular senescence. Premature senescence induced by oncogenic Ras also decreases LB1 expression through a pRb-dependent mechanism. Silencing the expression of LB1 slows cell proliferation and induces premature senescence in WI-38 cells. The effects of LB1 silencing on proliferation require the activation of p53, but not pRb. However, the induction of premature senescence requires both the p53 and pRb. The proliferation defects induced by silencing LB1 are accompanied by a p53 dependent reduction in mitochondrial ROS which can be rescued by growth under hypoxic conditions. In contrast to the effects of LB1 silencing, overexpression of LB1 increases the proliferation rate and delays the onset of senescence of WI-38 cells. This overexpression eventually leads to cell cycle arrest at the G1/S boundary. These results demonstrate the importance of LB1 in regulating the proliferation and senescence of human diploid cells through a ROS signaling pathway.

One of the common features of cultured cells derived from progeria patients bearing different mutations in LMNA is their premature senescence in culture (McClintock et al. 2006; Taimen et al. 2009; herein incorporated by reference in its entirety). Interestingly, LB1 expression, but not LA/C expression, is significantly decreased as progeria cells become senescent (Scaffidi and Misteli 2005; Kandert et al.

2007; Taimen et al. 2009; Liu et al. 2011; herein incorporated by reference in their entireties). However, the physiological significance of reduced LB1 expression in the proliferation and premature senescence of progeria patient cells has not previously been explored. Additional insights into the functions of nuclear lamins in cell proliferation have been derived from mouse models. Fibroblasts derived from a transgenic mouse model for progeria exhibit premature senescence (Mounkes et al. 2003; herein incorporated by reference in its entirety). Lmna−/− mice appear to develop normally, but growth defects such as low body weight and small size become obvious within 4 weeks after birth and the mice die by ~8 weeks (Sullivan et al. 1999). In contrast, homozygous mutant lmnb1 Δ/Δ mice die at birth with defects in lung, bone and brain development (Vergnes et al. 2004; Coffinier et al. 2011; herein incorporated by reference in their entireties). Further examination of these mice revealed that the defects in brain development are likely due to defective neuronal migration (Coffinier et al. 2011; herein incorporated by reference in its entirety). Embryonic lmnb1Δ/Δ fibroblasts are aneuploid and stop growing prematurely (Vergnes et al. 2004; herein incorporated by reference in its entirety). In the case of lmnb2−/− mice, defects in brain development and neuronal migration have been described (Coffinier et al. 2011; herein incorporated by reference in its entirety), but embryonic lmnb2−/− fibroblasts appear to proliferate normally (Coffinier et al. 2010; herein incorporated by reference in its entirety). In a different study, mice with the conditional double knockouts of both LMNB1 and LMNB2 in their skin keratinocytes develop normally (Yang et al. 2011; herein incorporated by reference in its entirety). However, forebrain specific knockout of either LMNB1 or LMNB2 leads to poor forebrain development and the double knockout results in complete cortical atrophy (Coffinier et al. 2011; herein incorporated by reference in its entirety). These results suggest that proliferation defects induced by the absence of B-type lamins may be specific for particular tissue types.

The findings in mouse models and in human cell lines derived from progeria patients, suggest that LB1 expression is coupled to cell proliferation. Experiments were conducted during development of embodiments of the present invention to explore the role of LB1 in the proliferation of human diploid fibroblasts (HDFs). Results demonstrate that silencing LB1 expression slows proliferation and rapidly induces premature senescence. On the other hand, the over-expression of GFP-LB1 increases the proliferation rate and delays the onset of senescence of HDFs.

Experiments conducted during development of embodiments of the present invention indicate that the nuclear intermediate filament protein LB1 plays an important role in the maintenance of cell proliferation. As further evidence for this role, LB1 levels decrease dramatically as cells become senescent and, when LB1 is depleted from cells they become prematurely senescent. Although LA, LC and LB2 do not appreciably decrease in their expression during senescence, mutations in LMNA and alterations in the amount of wt LA and the unprocessed precursor of LA (pre-LA) have been shown to cause premature senescence (Huang et al. 2008; Kandert et al. 2009; Taimen et al. 2009; Ragnauth et al. 2010; Moiseeva et al. 2011; herein incorporated by reference in their entireties). One of these LMNA mutations, which is the most prevalent mutation causing Hutchinson-Gilford Progeria Syndrome (HGPS), results in the accumulation of a permanently farnesylated form of LA with a 50 amino acid deletion near the carboxyl terminus, called LAΔ50/progerin. Progerin has also been observed to accumulate in an age-dependent fashion in tissues of normal individuals and in late passage normal cultured cells (Scaffidi and Misteli 2006; McClintock et al. 2007; Rodriguez et al. 2009; Cao et al. 2011; herein incorporated by reference in their entireties). Pre-LA has also been reported to accumulate in senescent cells (Ukekawa et al. 2007; herein incorporated by reference in its entirety). However, the expression of either progerin or pre-LA was not detected in senescent WI-38 cells or in LB1 silencing-induced prematurely senescent cells (see FIGS. 1C and 3A).

LMNB1 is an E2F target gene (Hallstrom et al. 2008; herein incorporated by reference in its entirety) and the reduction of its expression during senescence is mediated by pRb. Silencing LB1 expression immediately slows proliferation and induces premature senescence in HDFs, similar to the effects of silencing other E2F target genes (Gjoerup et al. 2007; Ibarra et al. 2008; herein incorporated by reference in its entirety). Experiments show that LMNB1 expression is unaltered in quiescent cells as it is in the subset of E2F1 target genes that do not respond to serum stimulation (Hallstrom et al. 2008; herein incorporated by reference in its entirety). The induction of premature senescence by LB1 silencing requires both p53 and pRb, but only p53 is required for the inhibition of proliferation. Furthermore, LB1 silencing activates the p53 pathway up regulating the transcription of p53 target genes, such as p21. These results suggest that LB1 is involved in some activity that, when disrupted, signals through p53. Data also demonstrate that pRb levels decrease and the expression of RB1 is repressed within 3 days after LB1 silencing. The depletion of pRb from cells by E7 expression prior to LB1 silencing has no effect on the inhibition of proliferation by silencing suggesting that the proliferation defects are mediated primarily by p53 activation. Although E7 expression and LB1 silencing both decrease pRb levels, E7 expression increases proliferation rates, whereas LB1 silencing decreases proliferation rates. If LB1 is involved in a process required for proliferation, the loss of LB1 after silencing would prevent any increase in proliferation rates due to the silencing-induced loss of pRb control over cell cycle progression. It has been shown that B-type lamins are associated with sites of DNA replication during mid-late S (Moir et al. 1994; herein incorporated by reference in its entirety) and disruption of lamin networks inhibits replication (Spann et al. 1997; Moir et al. 2000a; herein incorporated by reference in their entireties). Therefore, DNA replication is one possible function that may be disrupted by LB1 silencing. The failure to correctly replicate DNA activates a DNA damage response, leading to activation of the p53 pathway, inhibition of proliferation and induction of the senescence program. While an increase in γ-H2AX foci was not observed after silencing, there was an increase in the expression of ATM, CHEK1 and CHEK2, suggesting that silencing LB1 leads to defects in DNA replication.

The reduction in ROS levels following selection for LB1 silencing is indicates the mechanisms behind the inhibition of proliferation and induction of premature senescence; although the present invention is not limited to any particular mechanism of action and an understanding of the mechanism of action is not necessary to practice the present invention. ROS levels steadily increase as cells progress through the cell cycle and antioxidant treatment induces cell cycle arrest in late G1 (Havens et al. 2006; herein incorporated by reference in its entirety). In addition, modest increases in ROS levels due to hypoxia or prooxidant treatment are known to increase the proliferation rates of normal cells in culture and whole organisms (Bell et al. 2007; Lee et al. 2010; Yang and Hekimi 2010; herein incorporated by reference in their entireties). Taken together, these findings suggest that the decreased ROS levels detected shortly after silencing LB1 are insufficient to promote proliferation. This idea is supported by the rescue of the LB1 silencing proliferation defect under hypoxic conditions, which increases ROS, and by the increased sensitivity of LB1 silenced cells to NAC under normoxic conditions. The activation of several antioxidant genes within the first three days after silencing is a likely cause of this decrease in ROS. p53 plays a central role in regulating metabolism, most prominently in stimulating mitochondrial oxidative phosphorylation (Matoba et al. 2006; herein incorporated by reference in its entirety). Many antioxidant genes are also regulated by p53, therefore their up regulation in our experiments is consistent with the observed activation of the p53 pathway (Sablina et al. 2005; herein incorporated by reference in its entirety). Interestingly, the mitochondrial superoxide dismutase 2 gene (SOD2) is significantly up regulated within 24 hrs after selection, prior to detectable activation of p53. This suggests that the up regulation of SOD2 may be independent of p53, although the up regulation of SOD2 induced by LB1 silencing may also contribute to the activation of p53 (Behrend et al. 2005; herein incorporated by reference in its entirety). The increased oxygen consumption and up regulation of antioxidant genes in LB1 silenced cells may be due to a positive feedback mechanism initiated by LB1 silencing. Lamins have been implicated in transcriptional control (Spann et al. 2002; herein incorporated by reference in its entirety) and bind directly to several transcription factors (Dechat et al. 2008; herein incorporated by reference in its entirety). Therefore, it is possible that LB1 may more directly regulate the expression of SOD2 as well as other genes through interactions with transcription factors. Alternatively, LB1 may regulate chromatin organization and gene expression at a more global level (Guelen et al. 2008; Shimi et al. 2008; herein incorporated by reference in its entirety). Consistent with previous studies demonstrating that senescent cells accumulate ROS (Hagen et al. 1997; herein incorporated by reference in its entirety), our results show that ROS levels increase as LB1 silenced cells become senescent. This later increase in ROS could be attributable to the activation of p21 since a feedback loop between p21 and ROS production is required for maintaining senescence (Macip et al. 2002; Passos et al. 2010; herein incorporated by reference in their entireties).

A requirement for continued LB1 expression to maintain proliferation may not be universal. If the effects of LB1 loss are mediated by ROS, cell types may differ in their response to LB1 loss relative to how they respond to changes in ROS. Cell type differences may be related to the wide ranges of oxygen tensions to which cells are exposed depending on their locations within the body. For example, keratinocytes produce more ROS than fibroblasts in response to stress (Varani et al. 2005; herein incorporated by reference in its entirety), and therefore fibroblasts may exhibit more significant proliferation defects than keratinocytes after the reduction of ROS caused by LB1 silencing. This may explain why keratinocytes derived from LMNB1Δ/Δ/LMNB2Δ/Δ. mice do not show proliferation defects (Yang et al. 2011; herein incorporated by reference in its entirety). It is important to note that one study found increased ROS levels in mouse fibroblasts following LB1 silencing (Malhas et al. 2009; herein incorporated by reference in its entirety). The discrepancy with the present results may be attributable to the differences in experimental design and in the known differences in susceptibility to oxidative stress in human compared to mouse fibroblasts (Parrinello et al. 2003; herein incorporated by reference in its entirety). Several studies have also highlighted differences in the senescence mechanisms between fibroblasts and mesothelial cells (Rheinwald et al. 2002; herein incorporated by reference in its entirety). In addition, there may also be differences in the sensitivity to ROS between dermal fibroblasts and primary fetal lung fibroblast lines like the WI-38 and IMR-90 cells used in this study (Atamna et al. 2000; Wright and Shay 2001; Rheinwald et al. 2002; herein incorporated by reference in their entireties).

Figure 7:
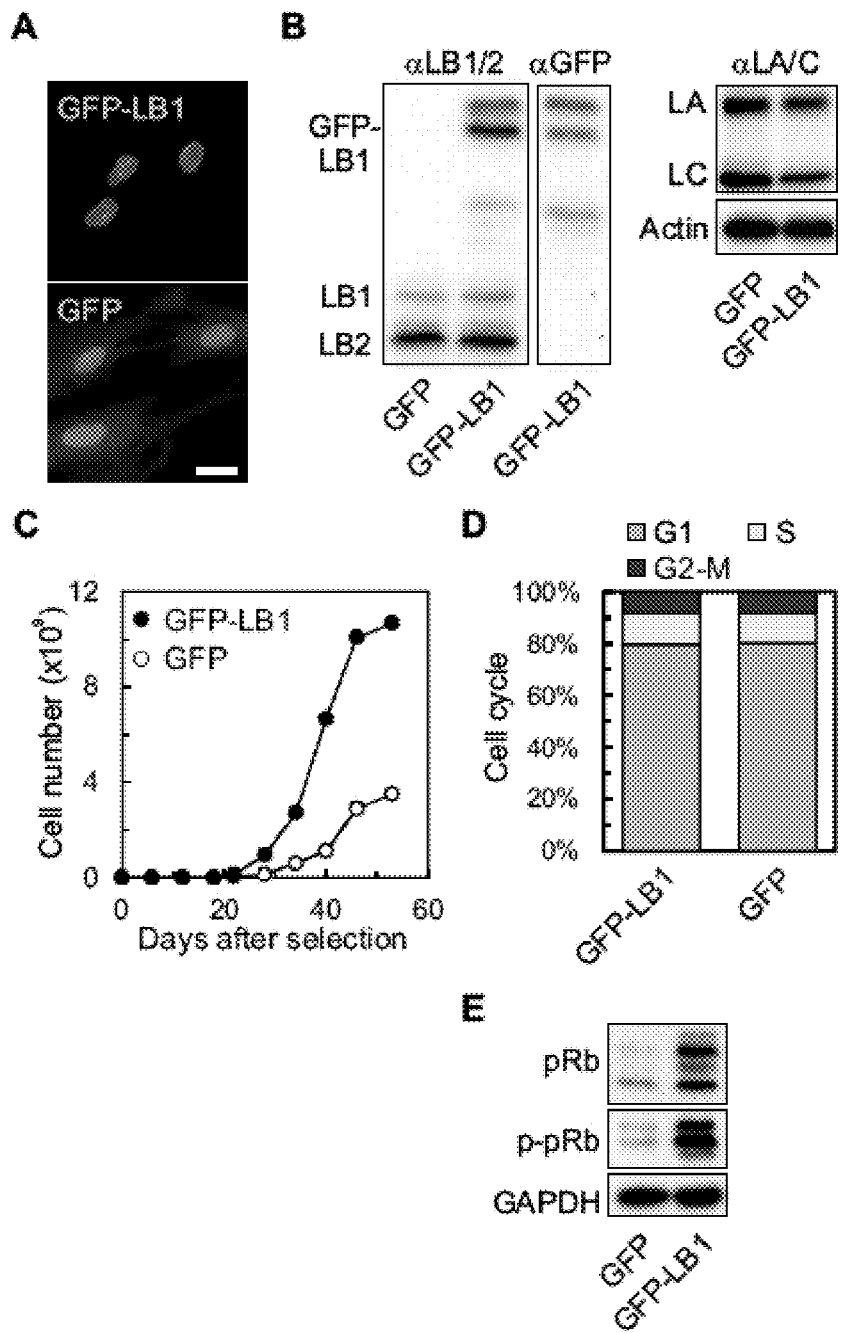
FIG. 7 shows the effects of GFP-LB1 over expression on cell proliferation. (A) Localization of GFP-LB1 and GFP (control) in WI-38 cells. Scale bar=10 μm. (B) The expression levels of GFP-LB1 and endogenous LA/C, LB1 and LB2 were determined by immunoblotting of whole cell lysates prepared 14 days following selection. Cells appeared to express multiple forms of LB1 including the top band most likely representing the non-farnesylated form of LB1 (see results) and the second band the farnesylated form. (C) Increased proliferation in GFP-LB1 (closed circle) expressing cells compared to GFP (open circle) expressing cells (see FIG. S4 for another proliferation curves). (D) Cell cycle analyses of the cells expressing GFP or GFP-LB1 by flow cytometry when they stopped proliferating. (E) Expression and phosphorylation of pRb in cells expressing GFP and GFP-LB 1. Phosphorylated pRb is indicated as p-pRb. GAPDH was used as a loading control.
Figure 8:
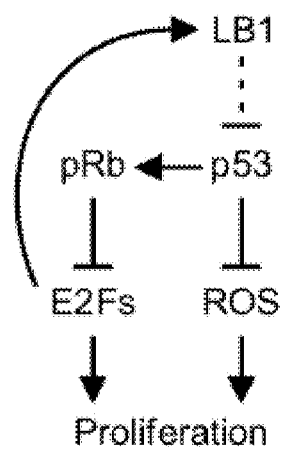
FIG. 8 shows result summary for LB1 function in cell proliferation. As an E2F target gene, LMNB1 expression is regulated in response to the proliferation state of the cell. The data show that LB1 functions are upstream of p53. However the exact mechanisms involved in the regulation of p53 by LB1 are not known (dashed line).
Figure 9:
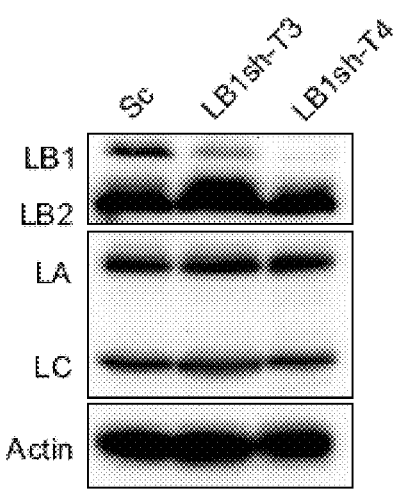
FIG. 9 shows validation of LB1 shRNAs to examine proliferation. (A) LB1 was silenced in WI-38 cells at PD24 using a scrambled sequence (Sc) and two different shRNA sequences targeting LMNB1 mRNA (LB1sh-T3 and LB1sh-T4; see Materials and Methods). The expression levels of LA/C, LB1 and LB2 were determined by immunoblotting. Actin was used as the loading control. (B) Growth curves of cells expressing different shRNAs. Open, closed circles and closed triangles represent Sc and LB1sh-T3 and LB1sh-T4 cells, respectively (n=4, *p=1.4×10−4 comparing Sc and LB1sh-T3; *p=4.5×10−8 comparing Sc and LB1sh-T4). (C) LB1 was silenced in IMR-90 cells at PD24 with LB1sh (LB1sh-T3) or Sc. GAPDH was used as the loading control. (D) Growth curves of Sc and LB1sh cells for 12 days after selection. Open and closed circles represent Sc and LB1sh cells, respectively (n=4; *p=1.0×10−2). Bars represent standard deviations. Asterisks indicate statistically significant changes (*p<5.0×10−2).
Figure 9:
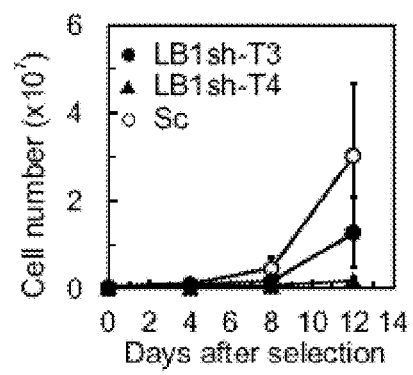
Figure 9:
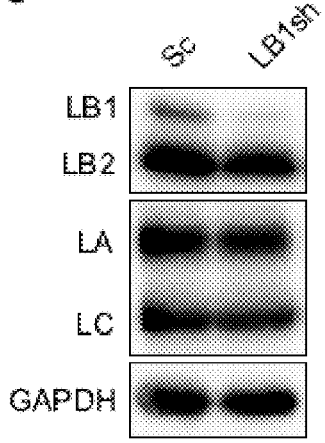
Figure 9:
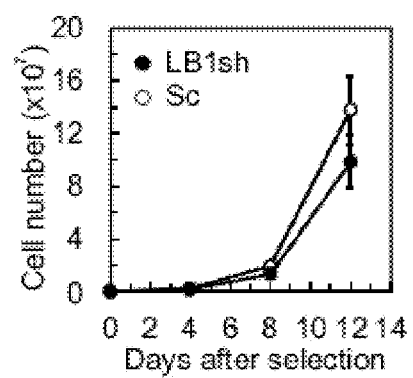
Figure 10:
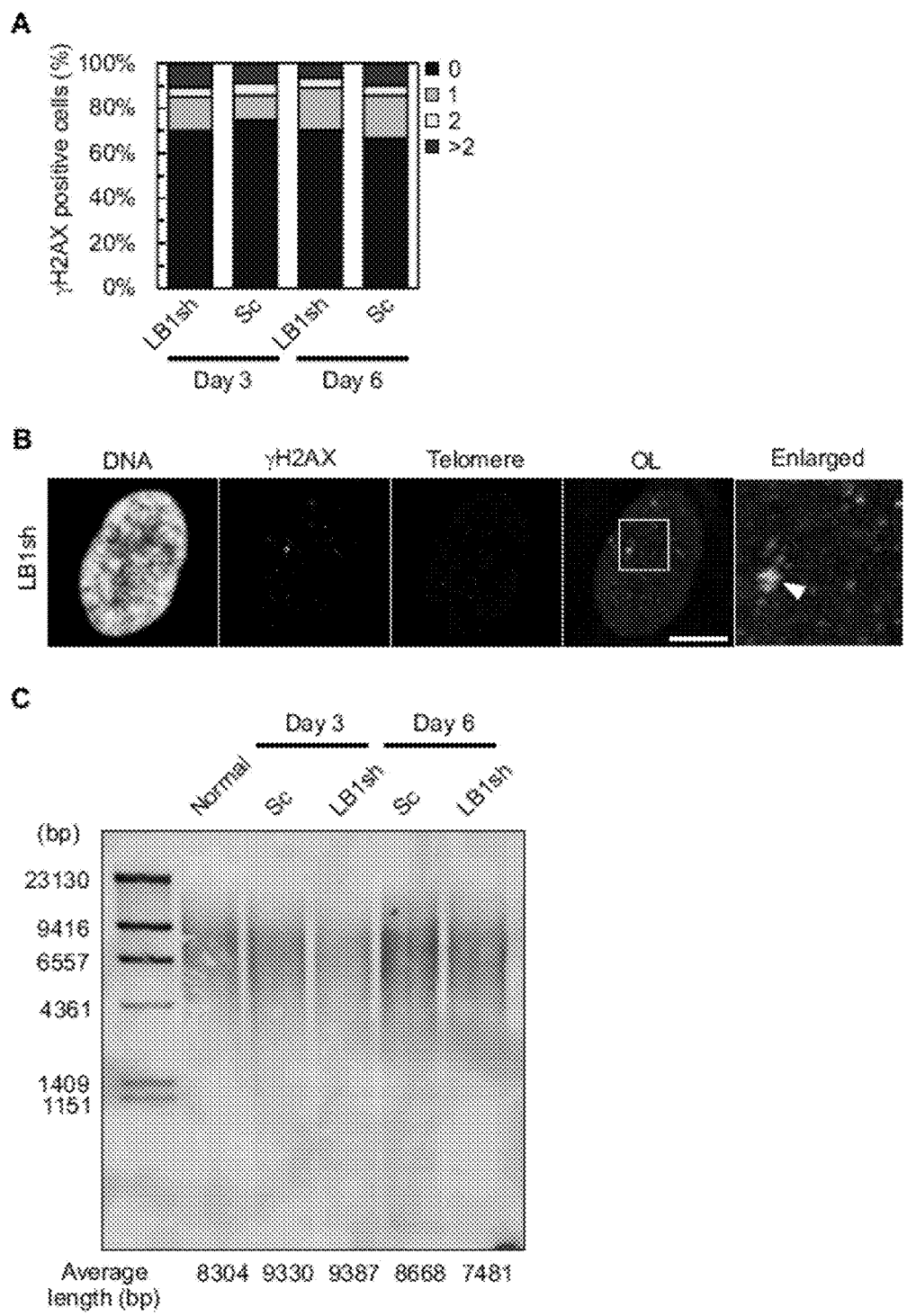
FIG. 10 shows analyses of telomere dysfunction in LB1 silenced WI-38 cells. (A) DNA damage foci were quantified by immunofluorescence with γH2AX antibody, 3 and 6 days after selection of LB1sh and Sc cells. Each color in the histogram represents the average number of γH2AX foci. (B) Localization of γH2AX (green) foci and telomeres (red) as visualized by immuno-FISH in LB1sh cells. (C) Telomere lengths were measured in normal (PD 24; untreated controls), LB1sh and Sc cells by southern blotting. Standard size markers are in the left lane.
Figure 11:
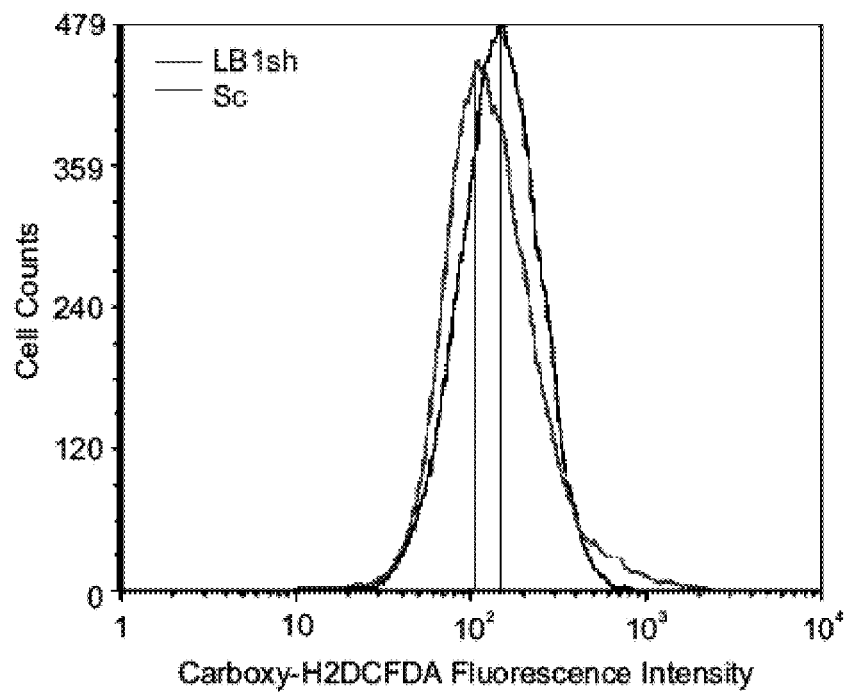
FIG. 11 shows determination of mitochondrial functions in LB1sh and Sc cells. (A) ROS was measured by carboxy-H2DCFDA 3 days after selection of LB1sh and Sc cells. Representative histograms of carboxy-H2DCFDA fluorescence signals in LB1sh (red) and Sc (black) cells are shown. The median values for fluorescence intensity were 11.9 for L δ 1 sh and 13.8 for Sc. (B) Mitochondrial mass in Sc and LB1sh was measured by MitoTracker Deep Red FM. Representative histograms of MitoTracker Deep Red fluorescence signals in LB1sh (red) and Sc (black) indicate that there were no changes in the number of mitochondria in LB1sh cells.
Figure 11:
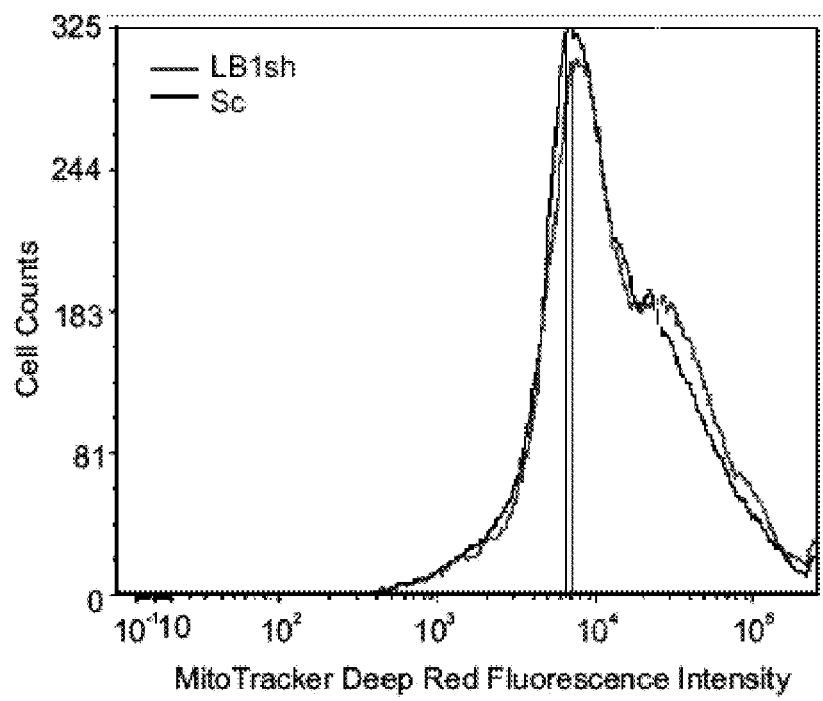
Figure 12:
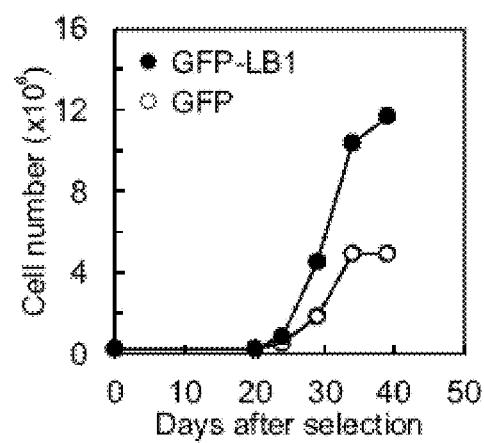
FIG. 12 shows validation of GFP-LB1 to examine proliferation. Another representative of increased proliferation in GFP-LB1 (closed circle) expressing cells compared to GFP (open circle) expressing cells (see FIG. 7C).

Experiments conducted during development of embodiments of the present invention also demonstrate that overexpression of GFP-LB1 and silencing of LB1 has opposite effects on the rate of cell proliferation. The mechanisms responsible for regulating proliferation and senescence by overexpressing LB1 remain unknown. It is possible that the overexpression of LB1 could act as a competitive inhibitor for farnesyltransferase and affect the farnesylation state of other proteins, such as Ras, that are involved in regulating cell proliferation (Sebti 2005; herein incorporated by reference in its entirety). However, accumulation of pre-LA or non-farnesylated endogenous LB1 and LB2 was not observed when LB1 was overexpressed, suggesting that other farnesylated proteins were probably not affected (see FIG. 7B). Surprisingly, when GFP-LB1 overexpressing cells cease proliferating, increased levels of both pRb and phosphorylated pRb were detected, indicating that their growth arrest is in late G1, most likely at the G1/S transition (Coller 2007; herein incorporated by reference in its entirety). In contrast, when cells become spontaneously senescent or prematurely senescent by LB1 silencing, pRb levels decrease and the cells arrest in early G1 (Burkhart and Sage 2008; herein incorporated by reference in its entirety). Together, these results imply that LB1 levels are important for regulating the entry of cells into S phase. It is also possible that mechanisms, such as the pRb pathway, might be affected through the association of LB1 with LA/C by regulating functional interactions between LA/C and other factors (Shimi et al. 2008; herein incorporated by reference in its entirety). Support for this idea comes from the findings that LA or LA-LAP2α complexes bind to and stabilizes pRb (Mancini et al. 1994; Nitta et al. 2006; Dorner et al. 2007; Pekovic et al. 2007 herein incorporated by reference in their entireties) and the stabilization of pRb by LA is associated with cell cycle arrest (Johnson et al. 2004; Rodriguez et al. 2010; herein incorporated by reference in their entireties). It is possible that the association of LB1 with LA/C affects the interactions of LA/C with other molecules, such as pRb. The roles of LB1 in regulating cell proliferation and senescence may be linked to pRb-mediated regulation of LMNB1 expression through a feedback loop (FIG. 8). Although the precise mechanisms linking LB1 functions to ROS signaling are unknown, these findings have significant implications for our understanding of cell proliferation and senescence in normal development, aging and cancer.

Antibodies

In certain embodiments, non-human antibodies are chimerized. In certain embodiments, mouse monoclonal antibodies that specifically bind human Lamin B1 are chimerized. Certain exemplary methods for making chimeric antibodies are provided, for example, in Morrison et al. (1984) Proc. Nat'l Acad. Sci. USA 81:6851-6855; Neuberger et al. (1984) Nature 312:604-608; Takeda et al. (1985) Nature 314:452-454; and U.S. Pat. Nos. 6,075,181 and 5,877,397; herein incorporated by reference in their entireties.

In certain embodiments, non-human antibodies are "humanized." In certain embodiments, mouse monoclonal antibodies that specifically bind human Lamin B1 are humanized. In certain embodiments, non-human (e.g., mouse) monoclonal antibodies raised against non-human Lamin B1, but which specifically bind (i.e., cross react) with human Lamin B1, are humanized. In certain embodiments, humanized antibodies retain their binding specificity and have reduced immunogenicity (e.g., reduced human anti-mouse antibody (HAMA) response) when administered to a human. In certain embodiments, humanization is achieved by methods including, but not limited to, CDR grafting and human engineering, as described in detail below.

In certain embodiments of humanized antibodies, one or more complementarity determining regions (CDRs) from the light and heavy chain variable regions of an antibody with the desired binding specificity (the "donor" antibody) are grafted onto human framework regions (FRs) in an "acceptor" antibody. Exemplary CDR grafting is described, e.g., in U.S. Pat. Nos. 6,180,370, 5,693,762, 5,693,761, 5,585,089, and 5,530,101; Queen et al. (1989) Proc. Nat'l Acad. Sci. USA 86:10029-10033; herein incorporated by reference in their entireties. In certain embodiments, one or more CDRs from the light and heavy chain variable regions are grafted onto consensus human FRs in an acceptor antibody. To create consensus human FRs, in certain embodiments, FRs from several human heavy chain or light chain amino acid sequences are aligned to identify a consensus amino acid sequence.

In certain embodiments, certain FR amino acids in the acceptor antibody are replaced with FR amino acids from the donor antibody. In certain such embodiments, FR amino acids from the donor antibody are amino acids that contribute to the affinity of the donor antibody for the target antigen. See, e.g., in U.S. Pat. Nos. 6,180,370, 5,693,762, 5,693,761, 5,585,089, and 5,530,101; Queen et al. (1989) Proc. Nat'l Acad. Sci. USA 86:10029-10033; herein incorporated by reference in its entirety. In certain embodiments, computer programs are used for modeling donor and/or acceptor antibodies to identify residues that are likely to be involved in binding antigen and/or to contribute to the structure of the antigen binding site, thus assisting in the selection of residues, such as FR residues, to be replaced in the donor antibody.

In certain embodiments, CDRs from a donor antibody are grafted onto an acceptor antibody comprising a human constant region. In certain such embodiments, FRs are also grafted onto the acceptor. In certain embodiments, CDRs from a donor antibody are derived from a single chain Fv antibody. In certain embodiments, FRs from a donor antibody are derived from a single chain Fv antibody. In certain embodiments, grafted CDRs in a humanized antibody are further modified (e.g., by amino acid substitutions, deletions, or insertions) to increase the affinity of the humanized antibody for the target antigen. In certain embodiments, grafted FRs in a humanized antibody are further modified (e.g., by amino acid substitutions, deletions, or insertions) to increase the affinity of the humanizedantibody for the target antigen.

In certain embodiments, non-human antibodies may be humanized using a "human engineering" method. See, e.g., U.S. Pat. Nos. 5,766,886 and 5,869,619; herein incorporated by reference in their entireties. In certain embodiments of human engineering, information on the structure of antibody variable domains (e.g., information obtained from crystal structures and/or molecular modeling) is used to assess the likelihood that a given amino acid residue in a variable region is (a) involved in antigen binding, (b) exposed on the antibody surface (i.e., accessible to solvent), or (c) buried within the antibody variable region (i.e., involved in maintaining the structure of the variable region). Furthermore, in certain embodiments, human variable region consensus sequences are generated to identify residues that are conserved among human variable regions. In certain embodiments, that information provides guidance as to whether an amino acid residue in the variable region of a non-human antibody should be substituted.

In certain embodiments, an antibody against Lamin B1 is of any isotype selected from IgM, IgD, IgG, IgA, and IgE. In certain embodiments, an antibody against Lamin B1 is of the IgG isotype. In certain such embodiments, an antibody is of the subclass IgG1, IgG2, IgG3, or IgG4. In certain embodiments, an antibody against Lamin B1 is of the IgM isotype. In certain such embodiments, an antibody is of the subclass IgM1 or IgM2. In certain embodiments, an antibody against Lamin B1 is of the IgA isotype. In certain such embodiments, an antibody is of the subclass IgA1 or IgA2. In certain embodiments, an antibody against Lamin B1 comprises a human kappa light chain and a human IgG1 or IgG2 heavy chain. In certain embodiments, an antibody against Lamin B1 comprises a mouse kappa light chain and a mouse IgG1 or IgG2 heavy chain.

In various embodiments, an antibody is modified to alter one or more of its properties. In certain embodiments, a modified antibody may possess advantages over an unmodified antibody, such as increased stability, increased time in circulation, or decreased immunogenicity (see, e.g., U.S. Pat. No. 4,179,337; herein incorporated by reference in its entirety). In certain embodiments, an antibody is modified by linking it to a nonproteinaceous moiety. In certain embodiments, an antibody is modified by altering the glycosylation state of the antibody, e.g., by altering the number, type, linkage, and/or position of carbohydrate chains on the antibody. In certain embodiments, an antibody is altered so that it is not glycosylated.

In certain embodiments, one or more chemical moieties are linked to the amino acid backbone and/or carbohydrate residues of the antibody. Certain exemplary methods for linking a chemical moiety to an antibody are known to those skilled in the art. Such methods include, but are not limited to, acylation reactions or alkylation reactions. See, for example, EP 0 401 384; Malik et al. (1992), Exp. Hematol., 20:1028-1035; Francis (1992), Focus on Growth Factors, 3(2):4-10, published by Mediscript, Mountain Court, Friern Barnet Lane, London N20 OLD, UK; EP 0 154 316; EP 0 401 384; WO 92/16221; WO 95/34326; WO 95/13312; WO 96/11953; WO 96/19459 and WO 96/19459; herein incorporated by reference in their entireties. In certain embodiments, any of these reactions are used to generate an antibody that is chemically modified at its amino-terminus.

In certain embodiments, an antibody is linked to a detectable label, such as an enzymatic, fluorescent, isotopic or affinity label. In certain such embodiments, a detectable label allows for the detection or isolation of the antibody. In certain embodiments, a detectable label allows for the detection of an antigen bound by the antibody.

In certain embodiments, an antibody is modified by linking it to one or more polymers. In certain embodiments, an antibody is linked to one or more water-soluble polymers. In certain such embodiments, linkage to a water-soluble polymer reduces the likelihood that the antibody will precipitate in an aqueous environment, such as a physiological environment. In certain embodiments, a therapeutic antibody is linked to a water-soluble polymer. In certain embodiments, one skilled in the art can select a suitable water-soluble polymer based on considerations including, but not limited to, whether the polymer/antibody conjugate will be used in the treatment of a patient and, if so, the pharmacological profile of the antibody (e.g., half-life, dosage, activity, antigenicity, and/or other factors).

Certain exemplary clinically acceptable, water-soluble polymers include, but are not limited to, polyethylene glycol (PEG); polyethylene glycol propionaldehyde; copolymers of ethylene glycol/propylene glycol; monomethoxy-polyethylene glycol; carboxymethylcellulose; dextran; polyvinyl alcohol (PVA); polyvinyl pyrrolidone, poly-1,3-dioxolane; poly-1,3,6-trioxane; ethylene/maleic anhydride copolymer; poly-.beta.-amino acids (either homopolymers or random copolymers); poly(n-vinyl pyrrolidone)polyethylene glycol; polypropylene glycol homopolymers (PPG) and other polyalkylene oxides; polypropylene oxide/ethylene oxide copolymers; polyoxyethylated polyols (POG) (e.g., glycerol) and other polyoxyethylated polyols; polyoxyethylated sorbitol, polyoxyethylated glucose, colonic acids or other carbohydrate polymers; and Ficoll, dextran, or mixtures thereof. Certain exemplary PEGs include, but are not limited to, certain forms known in the art to be useful in antibody modification, such as mono-(C.sub.1-C.sub.10) alkoxy- or aryloxy-PEG. In certain embodiments, PEG propionaldehyde may have advantages in manufacturing due to its stability in water.

In certain embodiments, a water-soluble polymer is of any molecular weight. In certain embodiments, a water-soluble polymer is branched or unbranched. In certain embodiments, a water-soluble polymer has an average molecular weight of about 2 kDa to about 100 kDa, including all points between the end points of the range. In certain embodiments, a water-soluble polymer has an average molecular weight of about 5 kDa to about 40 kDa. In certain embodiments, a water-soluble polymer has an average molecular weight of about 10 kDa to about 35 kDa. In certain embodiments, a water-soluble polymer has an average molecular weight of about 15 kDa to about 30 kDa.

In certain embodiments, an antibody is linked to PEG (i.e., an antibody is "pegylated"). In various embodiments, PEG has low toxicity in mammals. See Carpenter et al. (1971) Toxicol. Appl. Pharmacol., 18, 35-401; herein incorporated by reference in its entirety. In various embodiments, PEG may reduce the immunogenicity of antibodies. For example, in certain embodiments, linkage of PEG to an antibody having non-human sequences may reduce the antigenicity of that antibody when administered to a human.

In certain embodiments, a polymer is linked to one or more reactive amino acid residues in an antibody. Certain exemplary reactive amino acid residues include, but are not limited to, the alpha-amino group of the amino-terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, and activated glycosyl chains linked to certain asparagine, serine or threonine residues. Certain exemplary activated forms of PEG ("PEG reagents") suitable for direct reaction with proteins are known to those skilled in the art. For example, in certain embodiments, PEG reagents suitable for linkage to amino groups include, but are not limited to, active esters of carboxylic acid or carbonate derivatives of PEG, for example, those in which the leaving groups are N-hydroxysuccinimide, p-nitrophenol, imidazole or 1-hydroxy-2-nitrobenzene-4-sulfonate. In certain embodiments, PEG reagents containing maleimido or haloacetyl groups are used to modify sulfhydryl groups. In certain embodiments, PEG reagents containing amino, hydrazine and/or hydrazide groups may be used in reactions with aldehydes generated by periodate oxidation of carbohydrate groups in proteins.

In certain embodiments, a water-soluble polymer has at least one reactive group. In certain embodiments, an activated derivative of a water-soluble polymer, such as PEG, is created by reacting the water-soluble polymer with an activating group. In certain embodiments, an activating group may be monofunctional, bifunctional, or multifunctional. Certain exemplary activating groups that can be used to link a water-soluble polymer to two or more antibodies include, but are not limited to, the following groups: sulfone (e.g., chlorosulfone, vinylsulfone and divinylsulfone), maleimide, sulfhydryl, thiol, triflate, tresylate, azidirine, oxirane and 5-pyridyl. In certain embodiments, a PEG derivative is typically stable against hydrolysis for extended periods in aqueous environments at pHs of about 11 or less. In certain embodiments, a PEG derivative linked to another molecule, such as an antibody, confers stability from hydrolysis on that molecule. Certain exemplary homobifunctional PEG derivatives include, but are not limited to, PEG-bis-chlorosulfone and PEG-bis-vinylsulfone (see WO 95/13312; herein incorporated by reference in its entirety).

In certain embodiments, monoclonal antibodies are produced by standard techniques. In certain embodiments, monoclonal antibodies are produced by hybridoma-based methods. Certain such methods are known to those skilled in the art. See, e.g., Kohler et al. (1975) Nature 256:495-497; Harlow and Lane (1988) Antibodies: A Laboratory Manual Ch. 6 (Cold Spring Harbor Laboratory, Cold Spring Harbor, N.Y.; herein incorporated by reference in their entireties). In certain such embodiments, a suitable animal, such as a mouse, rat, hamster, monkey, or other mammal, is immunized with an immunogen to produce antibody-secreting cells. In certain embodiments, the antibody-secreting cells are B-cells, such as lymphocytes or splenocytes. In certain embodiments, lymphocytes (e.g., human lymphocytes) are immunized in vitro to generate antibody-secreting cells. See, e.g., Borreback et al. (1988) Proc. Nat'l Acad. Sci. USA 85:3995-3999; herein incorporated by reference in its entirety.

In certain embodiments, antibody secreting cells are fused with an "immortalized" cell line, such as a myeloid-type cell line, to produce hybridoma cells. In certain embodiments, hybridoma cells that produce the desired antibodies are identified, for example, by ELISA. In certain embodiments, such cells can then be subcloned and cultured using standard methods. In certain embodiments, such cells can also be grown in vivo as ascites tumors in a suitable animal host. In certain embodiments, monoclonal antibodies are isolated from hybridoma culture medium, serum, or ascites fluid using standard separation procedures, such as affinity chromatography. Guidance for the production of hybridomas and the purification of monoclonal antibodies according to certain embodiments is provided, for example, in Harlow and Lane (1988) Antibodies: A Laboratory Manual Ch. 8 (Cold Spring Harbor Laboratory, Cold Spring Harbor, N.Y.).

In certain embodiments, mouse monoclonal antibodies are produced by immunizing genetically altered non-human animals (e.g., mice) with an immunogen. In certain such embodiments, the animals are Lamin B1-deficient animals, which partially or completely lack Lamin B1 function. In certain such embodiments, the animals are "knockout" animals that lack all or part of a gene encoding Lamin B1. In certain embodiments, such knockout animals are immunized with Lamin B1. In certain embodiments, such knockout animals are immunized with human Lamin B1.

In certain embodiments, human monoclonal antibodies are raised in transgenic animals (e.g., mice) that are capable of producing human antibodies. See, e.g., U.S. Pat. Nos. 6,075,181 A and 6,114,598 A; and WO 98/24893 A2; herein incorporated by reference in their entireties. For example, in certain embodiments, human immunoglobulin genes are introduced (e.g., using yeast artificial chromosomes, human chromosome fragments, or germline integration) into mice in which the endogenous Ig genes have been inactivated. See, e.g., Jakobovits et al. (1993) Nature 362:255-258; Tomizuka et al. (2000) Proc. Nat'l Acad. Sci. USA 97:722-727; and Mendez et al. (1997) Nat. Genet. 15:146-156 (describing the XenoMouse II line of transgenic mice); herein incorporated by reference in their entireties.

In certain embodiments, such transgenic mice are immunized with an immunogen. In certain such embodiments, lymphatic cells (such as B-cells) from mice that express antibodies are obtained. In certain such embodiments, such recovered cells are fused with an "immortalized" cell line, such as a myeloid-type cell line, to produce hybridoma cells. In certain such embodiments, hybridoma cells are screened and selected to identify those that produce antibodies specific to the antigen of interest. Certain exemplary methods and transgenic mice suitable for the production of human monoclonal antibodies are described, e.g., in Jakobovits et al. (1993) Nature 362:255-258; Jakobovits (1995) Curr. Opin. Biotechnol. 6:561-566; Lonberg et al. (1995) Int. Rev. Immunol. 13:65-93; Fishwild et al. (1996) Nat. Biotechnol. 14:845-851; Mendez et al. (1997) Nat. Genet. 15:146-156; Green (1999) J. Immunol. Methods 231:11-23; Tomizuka et al. (2000) Proc. Nat'l Acad. Sci. USA 97:722-727; and reviewed in Little et al. (2000) Immunol. Today 21:364-370; and WO 98/24893; herein incorporated by reference in their entireties. In certain embodiments, human monoclonal antibodies against Lamin B1 are suitable for use as diagnostic or therapeutic antibodies.

In certain embodiments, human monoclonal antibodies are produced using a display-based method, such as, for example, any of those described below.

In certain embodiments, a monoclonal antibody is produced using phage display techniques. Certain exemplary antibody phage display methods are known to those skilled in the art and are described, for example, in Hoogenboom, Overview of Antibody Phage-Display Technology and Its Applications, from Methods in Molecular Biology: Antibody Phage Display: Methods and Protocols (2002) 178:1-37 (O'Brien and Aitken, eds., Human Press, Totowa, N.J.); herein incorporated by reference in their entireties.

In certain embodiments, an antibody phage-display library can be prepared using certain methods known to those skilled in the art. See, e.g., Hoogenboom, Overview of Antibody Phage-Display Technology and Its Applications, from Methods in Molecular Biology: Antibody Phage Display: Methods and Protocols (2002) 178:1-37 (O'Brien and Aitken, eds., Human Press, Totowa, N.J.); herein incorporated by reference in their entireties. In certain embodiments, variable gene repertoires are prepared by PCR amplification of genomic DNA or cDNA derived from the mRNA of antibody-secreting cells. For example, in certain embodiments, cDNA is prepared from mRNA of B-cells. In certain embodiments, cDNA encoding the variable regions of heavy and light chains is amplified, for example, by PCR.

In certain embodiments, heavy chain cDNA and light chain cDNA are cloned into a suitable vector. In certain embodiments, heavy chain cDNA and light chain cDNA are randomly combined during the cloning process, thereby resulting in the assembly of a cDNA library encoding diverse scFvs or Fabs. In certain embodiments, heavy chain cDNA and light chain cDNA are ligated before being cloned into a suitable vector. In certain embodiments, heavy chain cDNA and light chain cDNA are ligated by stepwise cloning into a suitable vector.

In certain embodiments, cDNA is cloned into a phage display vector, such as a phagemid vector. Certain exemplary phagemid vectors, such as pCES1, are known to those skilled in the art. In certain embodiments, cDNA encoding both heavy and light chains is present on the same vector. For example, in certain embodiments, cDNA encoding scFvs are cloned in frame with all or a portion of gene III, which encodes the minor phage coat protein pIII. In certain such embodiments, the phagemid directs the expression of the scFv-pIII fusion on the phage surface. Alternatively, in certain embodiments, cDNA encoding heavy chain (or light chain) is cloned in frame with all or a portion of gene III, and cDNA encoding light chain (or heavy chain) is cloned downstream of a signal sequence in the same vector. The signal sequence directs expression of the light chain (or heavy chain) into the periplasm of the host cell, where the heavy and light chains assemble into Fab fragments. Alternatively, in certain embodiments, cDNA encoding heavy chain and cDNA encoding light chain are present on separate vectors. In certain such embodiments, heavy chain and light chain cDNA is cloned separately, one into a phagemid and the other into a phage vector, which both contain signals for in vivo recombination in the host cell.

In certain embodiments, recombinant phagemid or phage vectors are introduced into a suitable bacterial host, such as E. coli. In certain embodiments using phagemid, the host is infected with helper phage to supply phage structural proteins, thereby allowing expression of phage particles carrying the antibody-pIII fusion protein on the phage surface.

In certain embodiments, "synthetic" antibody libraries are constructed using repertoires of variable genes that are rearranged in vitro. For example, in certain embodiments, individual gene segments encoding heavy or light chains are randomly combined using PCR. In certain such embodiments, additional sequence diversity can be introduced into the CDRs, and possibly FRs, e.g., by error prone PCR.

In certain embodiments, the selection of antibodies having the desired binding specificity from a phage display library is achieved by successive panning steps. In certain embodiments of panning, library phage preparations are exposed to antigen. In certain such embodiments, the phage-antigen complexes are washed, and unbound phage are discarded. In certain such embodiments, bound phage are recovered and subsequently amplified by infecting E. coli. In certain such embodiments, monoclonal antibody-producing phage may be cloned by picking single plaques. In certain embodiments, the above process is repeated. In certain embodiments, the antigen used in panning is any of the immunogens described below. In certain embodiments, the antigen is immobilized on a solid support to allow purification of antigen-binding phage by affinity chromatography. In certain embodiments, the antigen is biotinylated, thereby allowing the separation of bound phage from unbound phage using streptavidin-coated magnetic beads. In certain embodiments, the antigen may be immobilized on cells (for direct panning), in tissue cryosections, or on membranes (e.g., nylon or nitrocellulose membranes). Other variations of certain panning procedures may be routinely determined by one skilled in the art.

In certain embodiments, a yeast display system is used to produce monoclonal antibodies. In certain such systems, an antibody is expressed as a fusion protein with all or a portion of the yeast AGA2 protein, which becomes displayed on the surface of the yeast cell wall. In certain such embodiments, yeast cells expressing antibodies with the desired binding specificity can then be identified by exposing the cells to fluorescently labeled antigen. In certain such embodiments, yeast cells that bind the antigen can then be isolated by flow cytometry. See, e.g., Boder et al. (1997) Nat. Biotechnol. 15:553-557; herein incorporated by reference in its entirety.

In certain embodiments, the affinity of an antibody for a particular antigen is increased by subjecting the antibody to affinity maturation (or "directed evolution") in vitro. In vivo, native antibodies undergo affinity maturation through somatic hypermutation followed by selection. Certain in vitro methods mimic that in vivo process, thereby allowing the production of antibodies having affinities that equal or surpass that of native antibodies. In certain embodiments of affinity maturation, mutations are introduced into a nucleic acid sequence encoding the variable region of an antibody having the desired binding specificity. See, e.g., Hudson et al. (2003) Nature Med. 9:129-134; Brekke et al. (2002) Nature Reviews 2:52-621; herein incorporated by reference in their entireties. In certain embodiments, mutations are introduced into the variable region of the heavy chain, light chain, or both. In certain embodiments, mutations are introduced into one or more CDRs. In certain such embodiments, mutations are introduced into H3, L3, or both. In certain embodiments, mutations are introduced into one or more FRs. In certain embodiments, a library of mutations is created, for example, in a phage, ribosome, or yeast display library, so that antibodies with increased affinity may be identified by standard screening methods. See, e.g., Boder et al. (2000) Proc. Nat'l Acad. Sci. USA 97:10701-10705; Foote et al. (2000) Proc. Nat'l Acad. Sci. USA 97:10679-10681; Hoogenboom, Overview of Antibody Phage-Display Technology and Its Applications, from Methods in Molecular Biology: Antibody Phage Display: Methods and Protocols (2002) 178:1-37 (O'Brien and Aitken, eds., Human Press, Totowa, N.J.); and Hanes et al. (1998) Proc. Nat'l Acad. Sci. USA 95:14130-14135; herein incorporated by reference in their entireties.

In certain embodiments, mutations are introduced by site-specific mutagenesis based on information on the antibody's structure, e.g., the antigen binding site. In certain embodiments, mutations are introduced using combinatorial mutagenesis of CDRs. In certain embodiments, all or a portion of the variable region coding sequence is randomly mutagenized, e.g., using *E. coli* mutator cells, homologous gene rearrangement, or error prone PCR. In certain embodiments, mutations are introduced using "DNA shuffling." See, e.g., Crameri et al. (1996) Nature Med. 2:100-102; Fermer et al. (2004) Tumor Biology 25:7-13; herein incorporated by reference in their entireties.

In certain embodiments, "chain shuffling" is used to generate antibodies with increased affinity. In certain embodiments of chain shuffling, one of the chains, e.g., the light chain, is replaced with a repertoire of light chains, while the other chain, e.g., the heavy chain, is unchanged, thus providing specificity. In certain such embodiments, a library of chain shuffled antibodies is created, wherein the unchanged heavy chain is expressed in combination with each light chain from the repertoire of light chains. In certain embodiments, such libraries may then be screened for antibodies with increased affinity. In certain embodiments, both the heavy and light chains are sequentially replaced. In certain embodiments, only the variable regions of the heavy and/or light chains are replaced. In certain embodiments, only a portion of the variable regions, e.g., CDRs, of the heavy and/or light chains are replaced. See, e.g., Hudson et al. (2003) Nature Med. 9:129-134; Brekke et al. (2002) Nature Reviews 2:52-62; Kang et al. (1991) Proc. Nat'l Acad. Sci. USA 88:11120-11123; Marks et al. (1992) Biotechnology 10:779-83; herein incorporated by reference in their entireties.

In certain embodiments, mouse monoclonal antibodies that specifically bind human Lamin B1 (including, but not limited to, mouse monoclonal antibodies raised against mouse Lamin B1 but which specifically bind (i.e., cross react) with human Lamin B1) are subject to sequential chain shuffling. In certain embodiments, for example, the heavy chain of a given mouse monoclonal antibody is combined with a new repertoire of human light chains, and antibodies with the desired affinity are selected. In certain such embodiments, the light chains of the selected antibodies are then combined with a new repertoire of human heavy chains, and antibodies with the desired affinity are selected. Thus, in certain embodiments, human antibodies having the desired antigen binding specificity and affinity are selected.

Alternatively, in certain embodiments, the heavy chain of a given mouse monoclonal antibody is combined with a new repertoire of human light chains, and antibodies with the desired affinity are selected from this first round of shuffling. In certain embodiments, the light chain of the original mouse monoclonal antibody is combined with a new repertoire of human heavy chains, and antibodies with the desired affinity are selected from this second round of shuffling. In certain embodiments, human light chains from the antibodies selected in the first round of shuffling are then combined with human heavy chains from the antibodies selected in the second round of shuffling. Thus, in certain embodiments, human antibodies having the desired antigen binding specificity and affinity are selected.

In certain embodiments, a "ribosome display" method is used that alternates antibody selection with affinity maturation. In certain embodiments of a ribosome display method, antibody-encoding nucleic acid is amplified by RT-PCR between the selection steps. Thus, in certain embodiments, error prone polymerases may be used to introduce mutations into the nucleic acid. A nonlimiting example of such a method is described in detail in Hanes et al. (1998) Proc. Nat'l Acad. Sci. USA 95:14130-14135; herein incorporated by reference in its entirety.

In certain embodiments, a monoclonal antibody is produced by recombinant techniques. See, e.g., U.S. Pat. No. 4,816,567; herein incorporated by reference in its entirety. In certain such embodiments, nucleic acid encoding monoclonal antibody chains are cloned and expressed in a suitable host cell. For example, in certain embodiments, RNA can be prepared from cells expressing the desired antibody, such as mature B-cells or hybridoma cells, using standard methods. In certain embodiments, the RNA can then be used to make cDNA using standard methods. In certain embodiments, cDNA encoding a heavy or light chain polypeptide is amplified, for example, by PCR, using specific oligonucleotide primers. In certain embodiments, the cDNA is cloned into a suitable expression vector. In certain embodiments, the expression vector is then transformed or transfected into a suitable host cell, such as a host cell that does not endogenously produce antibody. Certain exemplary host cells include, but are not limited to, *E. coli*, COS cells, Chinese hamster ovary (CHO) cells, and myeloma cells. In certain embodiments, wherein heavy and light chains are coexpressed in the same host, reconstituted antibody may be isolated.

In certain embodiments, cDNA encoding a heavy or light chain can be modified. For example, in certain embodiments, the constant region of a mouse heavy or light chain can be replaced with the constant region of a human heavy or light chain. In this manner, in certain embodiments, a chimeric antibody can be produced which possesses human antibody constant regions but retains the binding specificity of a mouse antibody.

In certain embodiments, recombinant antibodies can be expressed in certain cell lines. In certain embodiments, sequences encoding particular antibodies can be used for transformation of a suitable mammalian host cell. According to certain embodiments, transformation can be by any known method for introducing polynucleotides into a host cell. Certain exemplary methods include, but are not limited to, packaging the polynucleotide in a virus (or into a viral vector) and transducing a host cell with the virus (or vector) and using certain transfection procedures known in the art, as exemplified by U.S. Pat. Nos. 4,399,216, 4,912,040, 4,740,461, and 4,959,455; herein incorporated by reference in their entireties. In certain embodiments, the transformation procedure used may depend upon the host to be transformed. Certain exemplary methods for introduction of heterologous polynucleotides into mammalian cells are known in the art and include, but are not limited to, dextran-mediated transfection, calcium phosphate precipitation, polybrene mediated transfection, protoplast fusion, electroporation, encapsulation of the polynucleotide(s) in liposomes, and direct microinjection of the DNA into nuclei.

Certain exemplary mammalian cell lines available as hosts for expression are known in the art and include, but are not limited to, many immortalized cell lines available from the American Type Culture Collection (ATCC), including but not limited to, Chinese hamster ovary (CHO) cells, HeLa cells, baby hamster kidney (BHK) cells, monkey kidney cells (COS), human hepatocellular carcinoma cells (e.g., Hep G2), and a number of other cell lines. In certain embodiments, cell lines may be selected by determining which cell lines produce high levels of antibodies that specifically bind Lamin B1.

In certain embodiments, to generate antibodies, an animal is immunized with an immunogen. In certain embodiments, an immunogen is a polypeptide comprising Lamin B1. In certain embodiments, an immunogen is a polypeptide comprising a fragment of Lamin B1. In certain embodiments, an immunogen is a polypeptide comprising the N-terminal coiled-coil domain of Lamin B1.).

Certain exemplary algorithms are known to those skilled in the art for predicting whether a peptide segment of a protein is hydrophilic and therefore likely to be exposed on the surface of the protein. Certain such algorithms use the primary sequence information of a protein to make such predictions. Certain such algorithms are based on the method of, for example, Hopp and Woods (1981) Proc. Nat'l Acad. Sci. USA 78:3824-3828, or Kyte and Doolittle (1982) J. Mol. Biol. 157:105-132. Certain exemplary algorithms are known to those skilled in the art for predicting the secondary structure of a protein based on the primary amino acid sequence of the protein. See, e.g., Corrigan et al. (1982) Comput. Programs Biomed. 3:163-168. Certain such algorithms are based on the method of, for example, Chou and Fasman (1978) Ann. Rev. Biochem. 47:25-276. In certain embodiments, peptide segments that are predicted to form .beta.-turns, and are therefore likely to be exposed on the surface of a protein, may be selected as immunogens.

In certain embodiments, an animal is immunized with an immunogen and one or more adjuvants. In certain embodiments, an adjuvant is used to increase the immunological response, depending on the host species. Certain exemplary adjuvants include, but are not limited to, Freund's adjuvant (complete and incomplete), mineral salts such as aluminum hydroxide or aluminum phosphate, surface active substances, chitosan, lysolecithin, pluronic polyols, polyanions, peptides, oil emulsions, and potentially useful human adjuvants such as BCG (bacille Calmette-Guerin) and *Corynebacterium parvum*. In certain embodiments, the immune response to an immunogen, e.g., a peptide immunogen, is enhanced by coupling the immunogen to another immunogenic molecule or "carrier protein." Certain exemplary carrier proteins include, but are not limited to, keyhole limpet hemocyanin (KLH), tetanus toxoid, diphtheria toxoid, ovalbumin, cholera toxoid, and immunogenic fragments thereof. For exemplary guidance in coupling peptide immunogens to carrier proteins, see, e.g., Ausubel et al. (1989) Current Protocols in Molecular Biology Ch. 11.15 (John Wiley & Sons, NY); and Harlow and Lane (1988) Antibodies: A Laboratory Manual Ch. 5 (Cold Spring Harbor Laboratory, Cold Spring Harbor, N.Y.); herein incorporated by reference in their entireties.

In certain embodiments, antibodies are screened for binding to Lamin B1 using certain routine methods that detect binding of antibody to antigen. For example, in certain embodiments, the ability of a monoclonal antibody to bind Lamin B1 is assayed by standard immunoblotting methods, such as Western blot. See, e.g., Ausubel et al. (1992) Current Protocols in Molecular Biology Ch. 10.8 (John Wiley & Sons, NY); Harlow and Lane (1988) Antibodies: A Laboratory Manual (Cold Spring Harbor Laboratory, Cold Spring Harbor, N.Y.); herein incorporated by reference in their entireties. In certain embodiments, Lamin B1 to be used in such assays may be isolated or may be present in a complex mixture of proteins and/or macromolecules.

In certain embodiments, the ability of a monoclonal antibody to bind Lamin B1 is assayed using a competitive binding assay, which evaluates the ability of a candidate antibody to compete with a known anti-Lamin B1 antibody for binding to Lamin B1.

In certain embodiments, a binding assay is used to quantify the binding kinetics (e.g., rate constant) or the binding affinity (e.g., association or dissociation constant) of an antibody against Lamin B1. In certain embodiments, the kinetics or affinity of binding is determined in the "solid-phase" by immobilizing antigen (e.g., Lamin B1) on a solid support. The immobilized antigen "captures" antibody from solution. In certain embodiments, the kinetics or affinity of binding is determined in the "solid-phase" by immobilizing antibody (e.g., antibody against Lamin B1) on a solid support. The immobilized antibody "captures" antigen from solution.

In certain embodiments, binding kinetics or binding affinity is determined using ELISA-based methods. In certain embodiments, binding kinetics or binding affinity is determined using biosensor-based technology, such as Biacore surface plasmon resonance technology (Biacore, Piscataway, N.J.). Certain such methods are known to those skilled in the art. See, e.g., McCafferty et al. (eds.) (1996) Antibody Engineering: A Practical Approach (IRL, Oxford, UK); Goldberg et al. (1993) Curr. Opin. Immunol. 5:278-281; Karlsson et al. (1991) J. Immunol. Methods 145:229-240; Malmgvist (1993) Curr. Opin. Immunol. 5:282-286; for review, see Hoogenboom, Overview of Antibody Phage-Display Technology and Its Applications, from Methods in Molecular Biology: Antibody Phage Display: Methods and Protocols (2002) 178: 1-37 at 19 (O'Brien and Aitken, eds., Human Press, Totowa, N.J.); herein incorporated by reference in their entireties.

In certain embodiments, the binding kinetics or binding affinity of a Fab fragment that specifically binds to Lamin B1 is determined. In certain instances, Fab fragments have the property of not multimerizing. Multimerization can, in certain instances, complicate the measurement of binding kinetics and binding affinity in "solid phase" methods. See, e.g., Hoogenboom, Overview of Antibody Phage-Display Technology and Its Applications, from Methods in Molecular Biology: Antibody Phage Display: Methods and Protocols (2002) 178:1-37 at 19 (O'Brien and Aitken, eds., Human Press, Totowa, N.J.); herein incorporated by reference in its entirety. Thus, in certain embodiments, a Fab fragment that specifically binds to Lamin B1 is suitable for use in a binding assay in which antigen is immobilized to a solid support, such as, for example, an ELISA-based assay or a Biacore assay. In certain embodiments, Fab fragments are generated from an intact antibody that specifically binds to Lamin B1 using enzymatic methods. In certain embodiments, Fab fragments are produced by expressing nucleic acids encoding Fab fragments in a recombinant expression system.

In certain embodiments, the binding kinetics or binding affinity of an antibody against Lamin B1 is determined using "solution phase" methods. In such methods, the kinetics or affinity of binding is measured for an antibody-antigen complex in solution. Certain such methods are known to those skilled in the art. A nonlimiting example of such a method is the "kinetic exclusion assay," or "KinExA." See, e.g., Blake et al. (1996) J. Biol. Chem. 271:27677-27685; Drake et al. (2004) Anal. Biochem. 328:35-43 (comparing Biacore "solid phase" and KinExA "solution phase" methods); herein incorporated by reference in their entireties.

In certain embodiments, the binding kinetics or binding affinity of a multivalent antibody or an antibody that multimerizes is determined using a solution phase method. In certain instances, the measurement of the binding kinetics or the binding affinity of a multivalent antibody or an antibody that multimerizes is amenable to solution phase analysis.

In certain embodiments, the binding affinity of an anti-Lamin B1 antibody, as measured by its $K_D$, is about $10^{-6}$ M or less. In certain embodiments, the binding affinity of an anti-Lamin B1 antibody is about $10^{-7}$ M, about $10^{-8}$ M, or about $10^{-9}$ M or less. In certain such embodiments, an anti-Lamin B1 antibody may be used as a therapeutic antibody. See, e.g., Hudson et al. (2003) Nature Med. 9:129-134. In certain embodiments, binding affinities of less than 10.sup.-9 M (e.g., binding affinities from about 500 pM to about 0.5 pM, including but not limited to, binding affinities from about 100 pM to about 5 pM) are achievable, e.g., using affinity maturation techniques. See, e.g., Boder et al. (2000) Proc. Nat'l Acad. Sci. USA 97:10701-10705; herein incorporated by reference in its entirety.

In certain embodiments, antibodies against Lamin B1 are used to detect the presence of Lamin B1 in vivo or in vitro. In certain embodiments, the level of Lamin B1 is measured. Certain exemplary detection methods are known in the art and include, but are not limited to, ELISA, radioimmunoassay, immunoblot, Western blot, immunofluorescence, and immunoprecipitation. In certain embodiments, antibodies against Lamin B1 are modified so that they may be directly detected, for example, by linking the antibody to a label. Certain exemplary labels include, but are not limited to, fluorophores, chromophores, radioactive atoms, electron-dense reagents, enzymes, and ligands. In certain embodiments, antibodies against Lamin B1 are detected by using a labeled "secondary" antibody that binds to a class of antibodies (e.g., a goat anti-mouse antibody).

EXPERIMENTAL

Example 1

Materials and Methods

Cell Culture

The human lung embryonic fibroblast lines WI-38 and IMR-90 (Coriell Cell Repositories) were cultured in modified Eagle's medium (MEMalpha, Invitrogen) supplemented with 10% fetal calf serum and 50 units/ml penicillin G/50 μg/ml streptomycin sulfate (Invitrogen) at 37° C. in a humidified CO2 incubator. For hypoxia experiments, cells were cultured in medium containing 20 mM HEPES (Invitrogen) at 1.5% O2 in an Invivo2 Hypoxia Workstation (Ruskinn Technology). To reduce reactive oxygen species, cells were cultured in medium containing 1 mM N-acetyl-L-cysteine (NAC, Sigma-Aldrich) and 20 mM HEPES both during and after selection. The medium was changed every 2 days with fresh medium supplemented with NAC.

Proliferation Assays

For proliferation assays, cells were passaged at 3-7 day intervals plating 2.5×105 cells/10 cm dish. At each passage, the cells from two 10 cm plates for each condition (control and experimental) were removed from the plates by trypsinization and counted using a hemocytometer. Population doublings (PD) were calculated using the equation: PD=log (Nh/Ns)/log 2, where Nh=number of harvested cells and Ns=number of seeded cells. Cumulative PDs were calculated by summing the PDs from all passages. Statistical analyses were performed using Gnumeric 1.10.16. The Student's T-test was used for most analyses. Differences in cell proliferation rates between samples were analyzed by two factor ANOVA with replication. Proliferation rates (PRs) in exponential growth phase were calculated using the equation: PR=(Nh−Nreh)/Nreh, where Nreh=number of harvested cells at the previous time point.

Retrovirus Vectors

For silencing the expression of LB1, the retrovirus vectors pSilencer-HsLMNB1shRNA-T3, pSilencer-HsLMNB1shRNA-T4, and pSilencer-Scrambled (used as a control) were prepared according to the manufacturer's instructions (Ambion). pSilencer 5.1-H1 Retro precut with Hind III and Bam HI was ligated with the target sequences for silencing LB1 (Shimi et al. 2008). For overexpressing GFP and GFP-LB1, the retrovirus vectors pQCXIP-GFP and pQCXIP-GFP-myc-HsLMNB1 were prepared using In-Fusion HD EcoDry Cloning System (Clontech). The DNA fragments of GFP and GFP-myc-HsLMNB1 with Bam HI was PCR-amplified using pEGFP-C1 (Clontech) and pEGFP-myc-HsLMNBJ (Moir et al. 2000b) and inserted into pQCXIP vector (Clontech). For induction of oncogenic stress, RasG12V was expressed from pBABE-puro-RasG12V with pBABE-puro as a control (both provided by Dr. Scott Lowe, Cold Spring Harbor Laboratory through Addgene; Weinberg, Whitehead Institute for Biomedical Research through Addgene) or silenced using pMSCV-hygro-miR30 (p53 shRNA) with pMSCVhygro as a control (both provided by Dr. Scott Lowe, Cold Spring Harbor Laboratory). For retrovirus production, 20 μg of virus vector and 1 μg of pVSV-G (Clontech) were electroporated into GP2-293 packaging cells (Clontech). Virus containing culture supernatants were collected at 24, 36 and 48 hrs following transfection. For transduction of virus into cells the culture supernatants containing virus were diluted 6-fold in fresh medium containing 4 μg/ml polybrene (Sigma-Aldrich) and incubated with WI-38 cells (PD 24) for 12 hrs. The culture medium was replaced with fresh virus-containing medium for an additional 12 hrs before replacement with medium containing antibiotics for selection. Virally transduced cells were selected by incubation in medium containing 3 μg/ml puromycin (Sigma-Aldrich), 200 μg/ml hygromycin B (Sigma-Aldrich) or 300 μg/ml G-418 (Clontech) for 3, 4 or 7 days, respectively. Following selection, the cells were incubated in medium without antibiotics. When two retrovirus vectors containing different selection markers were used, the viral transduction procedures for each vector were carried out sequentially prior to selection. Cells selected with antibiotics were incubated in fresh medium without antibiotics for at least 12 hrs before any assays were performed.

Measurement of Reactive Oxygen Species (ROS)

Mitochondrial ROS were determined by expressing roGFP fused to a mitochondrial localization sequence (Dooley et al. 2004; Hanson et al. 2004; Guzy et al. 2008). roGFP was introduced into the cells by adenovirus infection (5 PFU/cell). After 24 hrs, the infected cells were trypsinized and resuspended in PBS. The mean oxidation state of the roGFP was determined by measuring its fluorescence intensity with a Coulter CyAn (Becton Dickinson, emission 535 nm; excitation 405 nm and 488 nm). The fluorescence intensity was expressed as the ratio of oxidized (405 nm) to reduced (488 nm) roGFP. Maximum and minimum oxidation was determined after the cells were treated for 10 min with 1 mM t-butyl hydroperoxide or 1 mM dithiothreitol respectively. Percent oxidation in the test sample was calculated by subtracting the minimum value from both the test sample and the maximum value and determining the ratio between those two values (Bell et al. 2007). Fold oxidation was calculated by normalizing the silenced samples to the controls. As an alternative method to measure ROS, total ROS was determined using Image-iT LIVE Green Reactive Oxygen Species Detection Kit (Invitrogen) according to the manufacturer's instructions. $1.0 \times 10^6$ cells grown in 10 cm culture dishes were incubated with Leibovitz's L-15 Medium (Invitrogen) with 25 μM of 5-(and-6)-carboxy-2',7'-dichlorodihydrofluorescein diacetate (carboxy-H2DCFDA) for 30 min at 37° C. Treated cells were trypsinized and resuspended in PBS. The oxidation product of carboxy-H2DCFDA was measured with a Coulter Epics XL-MCL (Becton Dickinson).

Measurement of Mitochondrial Mass

Mitochondrial mass was determined using MitoTrackerR Deep Red FM (Invitrogen) according to the manufacturer's instructions. $1.0 \times 10^6$ cells grown in 10 cm culture dishes were incubated with Leibovitz's L-15 Medium (Invitrogen) with 100 nM of MitoTracker Deep Red FM for 30 min at 37° C. Treated cells were trypsinized and resuspended in PBS. The signal of MitoTrackerR Deep Red FM was measured with a Coulter Epics XL-MCL (Becton Dickinson).

Measurement of Oxygen Consumption Rate (OCR)

OCR was measured with a Seahorse Bioscience instrument (model XF24) as previously described (Weinberg et al., 2010). $5.0 \times 10^4$ cells were seeded in the custom 24-well plate in growth medium for 24 hrs before assay. Prior to the assay the cells were equilibrated with bicarbonate-free DMEM (Invitrogen) at 37° C. for 1 hr in an incubator lacking CO2. In the assay, 5 μM oligomycin (oligo) for ATP inhibition and 10 μM carbonyl cyanide ptrifluoromethoxy-phenylhydrazone (FCCP) for mitochondrial uncoupling or 2 μM antimycin A/rotenone (Ant/Rot) for inhibiting electron transfer in complex I and III were added to the basal media. 5 minutes after the addition of each reagent, the rates of change of dissolved O2 concentration immediately surrounding the cells were measured for 1 min three times.

Quantitative RT-PCR

Total RNA from WI-38 cells was harvested using Trizol (Applied Biosystems) and subjected to DNAse I (Promega) treatment (3 u/μl of reaction mixture) followed by an additional precipitation with Trizol. An ND-1000 Spectrophotometer (NanoDrop Technologies) was used to assess the quality and concentration of the RNA preparations. RT-PCR reactions were carried out with the SuperScript VILO cDNA Synthesis kit (Invitrogen). For quantitative PCR (qRT-PCR) reactions, the Qiagen QuantiFast Multiplex RT-PCR Kit was used. The primers for LMNA, LMNB1, LMNB2, TP53, CDKN1A, SOD1, SOD2, SESN1, SESN2, PPARGC1A, PPARGC1B and GAPDH (QuantiTect Primer Assays kits) were obtained from Qiagen. For analysis of GPX1 forward primer: TTCCCGTGCAACCAGTTTG (SEQ ID NO.: 1) and reverse primer: TTCACCTCGCACTTCTCGAA (SEQ ID No.: 2) were used. The data were analyzed as described (Schefe et al. 2006). In addition, Human Cellular Senescence PCR Array analysis was performed according to the manufacturer's protocol (SABiosciences, Qiagen). Each experiment was repeated at least twice using parallel cultures and employing multiple technical repeats. The qRT-PCR analyses were carried out in an MJ Engine using Opticon 3 software. Real-time PCR p-values were determined by Student's T-test comparing $\Delta CT$ for the target genes to the average $\Delta CT$ for the reference genes (Yuan et al. 2006).

Immunofluorescence

Cells grown on glass coverslips were fixed either in methanol for 10 min at $-20°$ C. or in 3.7% formaldehyde in phosphate buffered saline (PBS) for 10 min on ice followed by extraction in 0.1% TRITON X-100 (octoxynol-9) in PBS for 10 min at 22°C. Primary antibodies included mouse anti-LA/C (1:200; JoL2, Chemicon), rabbit anti-LA/C (1:500; #266), rabbit anti-LB1 (1:1000) (Moir et al. 1995), goat anti-LB1 (1:300; M-20, Santa Cruz), mouse anti-LB2 (1:200; LN43, Abcam), rabbit anti-LB2 (1:1000; #327) (Shimi et al. 2008). Secondary antibodies included goat anti-mouse IgG-Alexa Fluor 488, goat anti-mouse IgG-Alexa Fluor 568 and donkey anti-goat Alexa Fluor 568 (all used at 1:200; Invitrogen). DNA was stained with 1 μg/mL of Hoechst 33258 (Invitrogen). Following processing, coverslips were mounted on slides in 20 mM Tris-Cl pH with 50% glycerol and containing 1% phenylenediamine (Sigma-Aldrich). Fixed cells were observed with either a Zeiss Axiolmager Z1 or a Zeiss LSM 510 META (Carl Zeiss) microscope using oil immersion objective lenses (PlanApochromat, 63× and 100×, 1.40 NA; Carl Zeiss).

Replication Labeling

Detection of DNA replication was carried out as described (Moir et al. 1994). Cells were labeled with 10 μM BrdU (Sigma-Aldrich) in growth medium for 6 hrs at 37° C. BrdU-labeled DNA was detected with mouse monoclonal anti-BrdU (1:500; BU-33, Sigma-Aldrich), followed with goat anti-mouse IgG-Alexa Fluor 488 (1:200; Invitrogen).

Detection of Senescence Associated β-Galactosidase (SA-β-gal) Activity

SA-β-gal was detected as described (Dimri et al. 1995). Cells grown on coverslips were fixed with 2.0% glutaraldehyde/3.7% formaldehyde for 15 min at room temperature. Following two washes with PBS, cells were incubated for 4 hrs at 37° C. in a solution containing 5-bromo-4-chloro-3-indolyl-β-D-galactopyranoside.

Detection of Apoptosis

Apoptosis was detected using the In Situ Cell Death Detection Kit, TMR red (Roche) according to the manufacturer's instructions. Cell grown on glass coverslips were fixed in 37% formaldehyde in PBS for 60 min at room temperature followed by extraction in 0.1% TRITON X-100 (octoxynol-9) in PBS for 2 min on ice. Fragmented DNA was labeled by the TUNEL reaction for 60 min at 37° C. The TUNEL reaction was terminated by washing in PBS and the total DNA was stained with Hoechst 33258.

Fluorescence In Situ Hybridization Combined with Immunofluorescence (Immuno-FISH)

Telomeres were localized in nuclei of cells grown on coverslips using the PNA FISH Kit/Cy3 (Dako) according to the manufacturer's instructions. Following the in situ hybridization, the cells were processed for indirect immunofluorescence with mouse anti-γH2AX antibody (Millipore) and Alexa Fluor 488-goat anti-mouse IgG (Molecular Probes). DNA was stained with Hoechst 33258.

Measurement of Telomere Restriction Fragments (TRF)

Telomere length was determined by terminal restriction fragment analysis. Total genomic DNA was isolated from WI-38 cells using the DNeasy Blood & Tissue Kit (Qiagen) and digested with a HinfI/RsaI enzyme mix (20 units per sample; New England Biolabs) at 37° C. overnight. The digested DNA was resolved by electrophoresis through a 0.8% agarose gel at 5 V/cm for 4 hrs, then denatured, neutralized, and transferred using capillary transfer overnight to a nylon membrane (Amersham Hybond-N+). An 800 bp T2AG3 telomere repeat probe was prepared from pSty11 (provided by Dr. Titia de Lange, Rockefeller University through Addgene) by excision, gel extraction, and end-labeling with digoxigenin d-UTP (Roche). The probe was hybridized to the transfer membrane under standard conditions and visualized using chemiluminescence with alkaline phosphatase. The mean telomere length was determined as previously described (Harley et al. 1990).

Cell Cycle Analysis $1.0 \times 10^6$ cells were collected and fixed on ice in 70% ethanol for 2 hrs. The cells were then incubated for 20 min at 37° C. in PBS containing 50 µg/mL propidium iodide, 200 µg/mL RNase A and 0.1% TRITON X-100 (octoxynol-9)followed by resuspension in PBS. The DNA content of each cell was measured by cell sorting with a Coulter Epics XLMCL (Becton Dickinson).

Example 2

Changes in the Expression of LB1 During Senescence

In order to determine if LB1 expression is correlated with the proliferation state of human diploid fibroblasts (HDFs), the expression and nuclear organization of A- and B-type lamins were studied in the HDF cell line WI-38. Cellproliferation and lamin expression were examined as a function of cumulative population doublings (PDs) beginning with cells at PD30 and ending when the cells became senescent at PD41. Senescent cells were identified using senescence-associated β-galactosidase (SA-β-gal) activity (Dimri et al. 1995), the formation of senescence associated heterochromatic foci (SAHF) (Narita et al. 2003), and the absence of BrdU incorporation (Kennedy et al. 2000; Johnson et al. 2004). The percentages of cells positive for SA-β-gal activity increased from ~1% (n=110) to ~55% (n=413) to ~100% (n=175); SAHF increased from ~3% (n=460) to ~32% (n=261) to ~55% (n=264); and BrdU incorporation decreased from ~30% (n=460) to ~11% (n=261) to 0% (n=304) at PD30, PD39 and PD41 respectively (FIG. 1A). Together, these results showed that in ~45 days the cells went from actively proliferating to pre-senescent and finally senescent at PD30, PD39 and PD41. Immunofluorescence revealed that all the lamins were localized normally in the lamina and nucleoplasm (FIG. 1A). However, by the time of senescence at PD41, LB1 staining was greatly reduced, while no obvious changes in LA/C and LB2 could be detected (FIG. 1A). There was also an obvious increase in cell size at PD41 and the nuclei in the senescent cells were larger and more convoluted than nuclei in actively growing cells.

Quantitative immunoblotting showed that the amount of LB1 decreased by ~80-90% as cells became senescent over the 45 days required to progress from PD30 to PD41 (FIG. 1B). The loss of LB1 first became noticeable between PDs 36-37 (days 19-24) and the amount of LB1 decreased gradually until the majority of cells were senescent at PD41 (day 45) (FIG. 1B, bottom panel). The protein levels of LA/C and LB2 in senescent cells (PD41) remained unchanged compared to actively proliferating cells at PD30 (FIG. 1C). To determine whether the loss of LB1 could be the result of decreased proliferation, PD30 cells were made quiescent by serum starvation for 72 hrs. Under these conditions the protein levels of all lamins remained unaltered compared to actively proliferating cells (FIG. 1C). The mRNA levels of LMNA, LMNB1, and LMNB2 were also assayed by qRT-PCR at PDs 30, 39 and 41. The LMNB1 transcripts decreased by ~95%, between PD30 and 41 (FIG. 1D). There were also much smaller decreases in LMNB2 mRNA levels while the expression of LMNA mRNA appeared to be maintained as cells entered senescence. Together, these results demonstrate that LB1 expression is transcriptionally down regulated as cells become senescent.

Example 3

Figure 2:
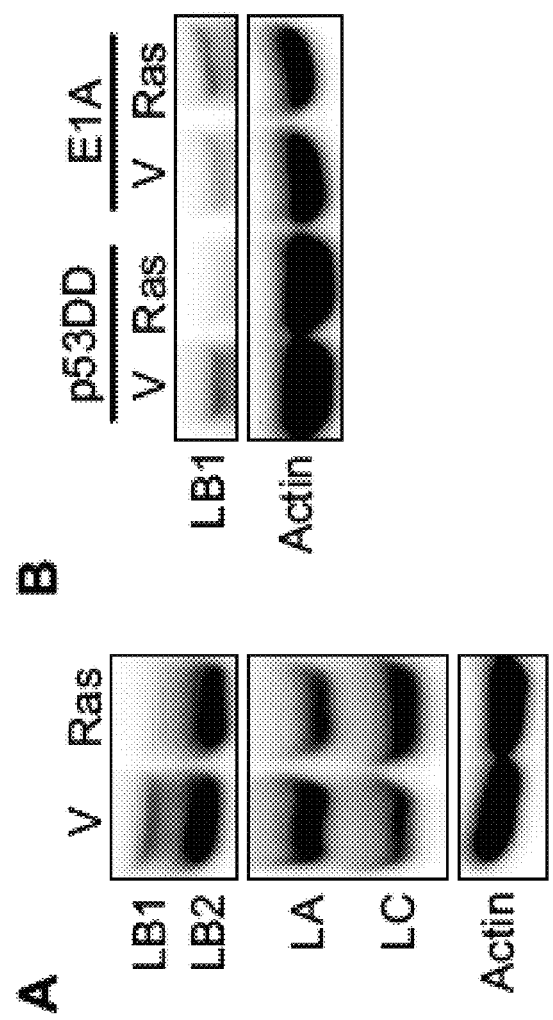
FIG. 2 shows senescence induced by the expression of oncogenic Ras (RasG12V) results in the down regulation of LB1. (A) RasG12V (Ras) or an empty vector (V) was expressed at PD24 in WI-38 cells. The expression levels of LB1, LB2, and LA/C in these cells were determined by immunoblotting 7 days following selection. (B) The expression levels of LB1 were determined after inhibition of either the p53 or pRb pathways by the expression of p53DD or E1A, respectively, followed by the expression of RasG12V to induce senescence.

Oncogenic Ras Induces Premature Senescence and the Resulting Loss of LB1 Requires pRb Premature senescence can be induced in HDFs by expression of an active form of oncogenic Ras (RasG12V) (Serrano et al. 1997). The expression of RasG12V in WI-38 cells at PD24 induced premature senescence within 7 days after selection. At this time, ~88% (n=432) of the cells were positive for SAHFs vs ~2% (n=430) in controls transfected with an empty vector (V); ~83% (n=166) contained SA-β-gal vs ~0.6% (n=168) for V; and ~0.5% (n=172) incorporated BrdU vs 17% (n=674) for V. In these prematurely senescent cells, LB1 levels decreased by ~98% and no substantial changes could be detected in LA/C and LB2 (FIG. 2A). These results showed that the rapid induction of premature senescence by oncogenic Ras is accompanied by a loss of LB1, similar to that seen in spontaneous senescence.

Attempts were then made to identify which of the well defined pathways leading to senescence were associated with the loss of LB1. The transcription factors p53 and retinoblastoma (pRb) are major regulators of genes involved in the control of cell cycle progression and proliferation (Polager and Ginsberg 2009). In response to the stress induced by oncogenic Ras in HDFs, both the p53 and pRb pathways are activated and mediate the steps involved in senescence (Campisi and d'Adda di Fagagna 2007; Rodier et al. 2011). Therefore, the involvement of each pathway in regulating LB1 expression during senescence was investigated. The p53 pathway was examined by expressing the dominant negative mutant p53DD which inhibits the activation of p53 (Shaulian et al. 1992). In cells stably expressing p53DD, RasG12V expression induced senescence within 7 days after selection. There was an increase in the number of cells positive for SA-β-gal (~65% [n=230] vs ~0.6% [n=333] for controls (p53DD/V)); SAHFs (~49% [n=268] vs 0% [n=386] for p53DD/V); and the number of cells incorporating BrdU decreased (~19% [n=268] vs ~31% [n=386] for p53DD/V). At the sametime, the level of LB1 decreased by ~98% (FIG. 2B) similar to the decrease in LB1 in cells induced to senesce with RasG12V in the absence of p53DD (see FIG. 2A). These results demonstrate that the loss of LB1 in premature senescence induced by RasG12V does not require activation of the p53 pathway.

To examine the role of the pRb pathway in mediating the decrease in LB1 protein levels during senescence, pRb was inactivated by expression of the adenovirus E1A oncoprotein (Jones 1990; Serrano et al. 1997). E1A rescues RasG12V-induced senescence by multiple pathways including overriding the negative effects of the Rb family on proliferation-associated genes and inhibiting the activation of p53 (Serrano et al. 1997; Deng et al. 2005). Since the previous experiment showed that the p53 pathway is not required for the reduction of LB1 expression induced by RasG12V, E1A expression can be used to test the role of pRb in the loss of LB1. When either the empty vector (V) or RasG12V vector was expressed in cells stably expressing E1A, the cells did not become senescent as determined by measuring the accumulation of the senescence markers and BrdU incorporation (Serrano et al. 1997). In contrast to the ~98% reduction in LB1 levels in cells made senescent by expressing RasG12V alone (FIG. 2A), LB1 levels were increased by ~72% in E1A/RasG12V expressing cells relative to controls (E1A/V) (FIG. 2B, right lanes). Therefore, the decrease in LB1 expression during RasG12V-induced senescence is probably due to the action of pRb. These results are consistent with previous studies showing that the E2F family of transcription factors regulates LMNB1 expression (Hallstrom et al. 2008).

Example 4

LB1 Silencing Inhibits Proliferation and Induces Premature Senescence

Figure 3:
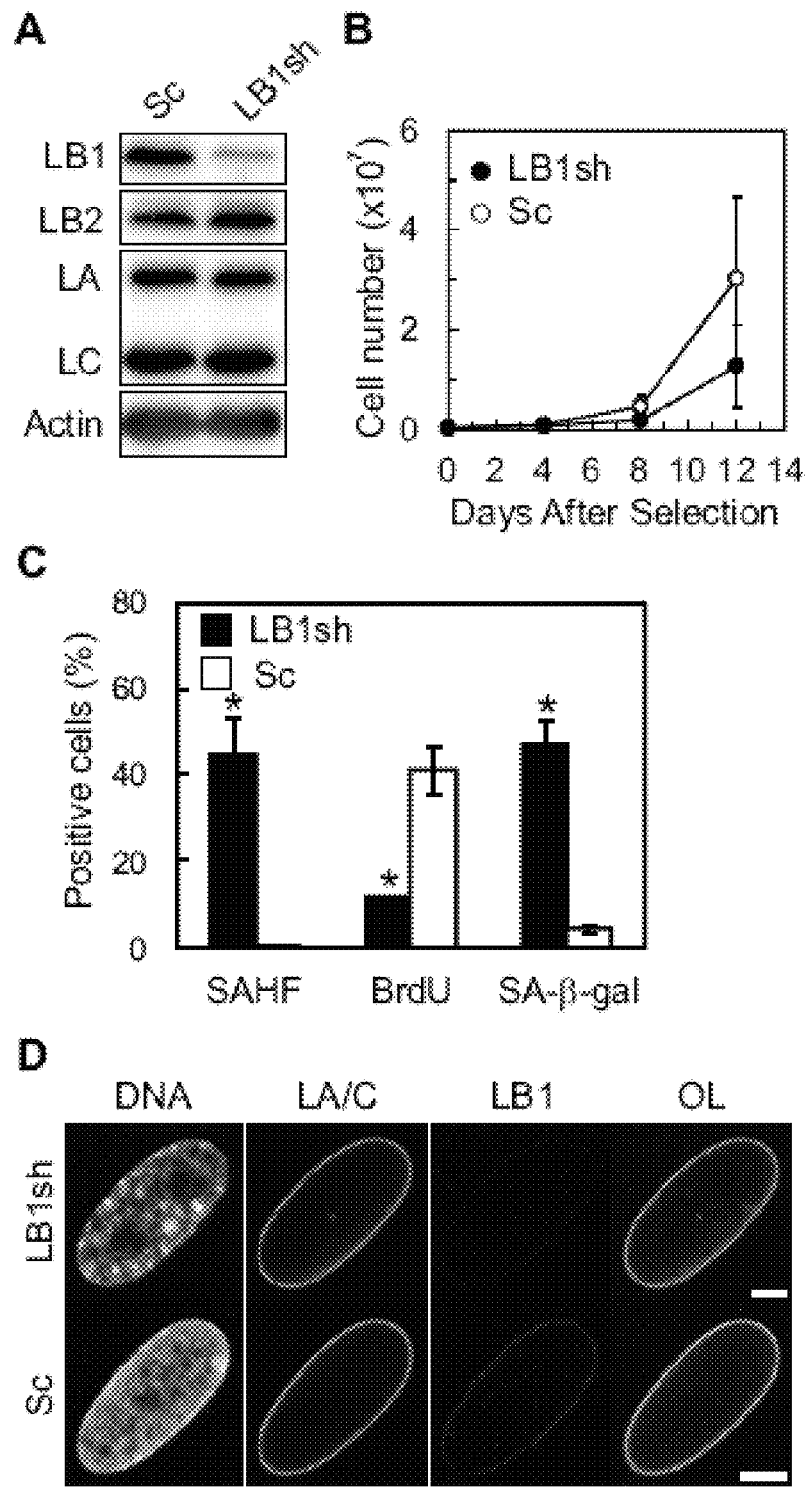
FIG. 3 shows silencing LB1 induces premature senescence. The effects of silencing LB1 expression on cell proliferation were determined at PD24 in WI-38 cells. (A) The expression levels of LB1, LB2, and LA/C were determined by immunoblotting at 8 days after selection for the vector expressing the LB1 targeted shRNA (LB1sh-T3; LB1sh) or a scrambled sequence (Sc). (B) Growth curves comparing the proliferation rates of Sc and LB1sh cells compared for 12 days following selection (n=4; p=1.4×10−4). Error bars represent standard deviations. (C) Senescence markers quantified 11 days following selection. The error bars indicate the standard deviations. There was a significant increase in the percentage of cells containing SAHF (n=2; *p=1.9×10−2) and SA-β-gal (n=2; *p=8.8×10−3) and a decrease in cells incorporating BrdU (n=2; *p=1.5×10−2) in LB1 silenced cells. Asterisks indicate statistically significant changes (*p<5.0×10−2). (D) Immunofluorescence of Sc and LB1sh cells. Anti-LA/C (green), anti-LB1 (red), and DNA stained with Hoechst 33258 (white or blue in overlay (OL)) Scale bar=5 µm.

The fact that LMNB1 expression is regulated by E2F transcription factors suggests that LB1 may have an important role in WI-38 cell proliferation. To test this, shRNAs targeted to LMNB1 transcripts (LB1sh) were used to silence LB1 expression in PD24 cells (Shimi et al. 2008). Two shRNA target sequences were examined and both shRNAs resulted in a ~80-90% decrease of LB1 at 8 days following selection, with no obvious changes in the expression levels of LA/C and LB2 (FIG. 3A, S1A). At 12 days, the proliferation rate of LB1 silenced cells was significantly decreased compared to controls with a scrambled sequence (Sc) (FIGS. 3B and S1B). A reduction in the rate of proliferation was also seen in another HDF line, IMR-90 (FIG. S1 C, D) although the effect was not as strong as in WI-38 cells. This is most likely due to the fact that the IMR-90 cells used go through ~60 PDs prior to senescence (Forsyth et al. 2003). In the case of WI-38 cells, these observations were extended to show that the slow proliferation following LB1 silencing was not attributable to a loss of cells by apoptosis, as determined by the TUNEL reaction. In addition, after 12 days, the number of LB1 silenced cells positive for SAHFs (~45% [n=432] LB1sh; ~0.5% [n=430] Sc) and SA-β-gal activity (~42% [n=434] LB1sh; ~4% [n=481] Sc) increased and there was a large decrease in cells incorporating BrdU (~12% LB1sh [n=745]; 41% Sc [n=697]) (see FIG. 3C). In addition, LB1 could not be detected by microscopy in cells containing nuclei with SAHFs (FIG. 3D). These results demonstrate that LB1 silencing slows cell proliferation and induces premature senescence.

Example 5

The Roles of p53 and pRb in the Inhibition of Cell Proliferation and the Induction of Premature Senescence by LB1 Silencing In order to investigate the process of premature senescence induced by LB1 silencing, the human cellular senescence PCR array (SA-Biosciences, Quiagen) was used to analyze 84 genes involved in the initiation and progression of senescence. To identify mechanisms involved following LB1 silencing, this analysis was carried out 3 days following selection. This is the time at which recognizable changes in the proliferation rate of WI-38 cells were first observed (see FIG. 3B). The mRNA levels of 45 genes were significantly altered by over two fold; 43 genes were up regulated and 2 genes were down regulated. Among the 45 genes affected, 41 were altered as expected for cells undergoing senescence by known mechanisms (GeneCards) (Table 1).

TABLE 1

Table 1. qRT-PCR array for Senescence pathways.

|  | C(t) of Sc in Exp. 1 | C(t) of LB1sh in Exp. 1 | C(t) of Sc in Exp. 2 | C(t) of LB1sh in Exp. 2 | Ave. LB1sh/ Sc in Exp. 1 | Ave. LB1sh/ Sc in Exp. 2 |
|---|---|---|---|---|---|---|
| Senescence Pathway | | | | | | |
| ATM | 23.56 | 22.53 | 21.14 | 19.84 | 2.67 | 2.55 |
| BMI1 | 20.22 | 20.04 | 19.48 | 19.49 | 1.47 | 1.03 |
| CCND1 | 16.21 | 14.47 | 17.27 | 14.99 | 4.36 | 5.03 |
| CCNE1 | 20.46 | 20.80 | 20.18 | 20.60 | 1.03 | 0.77 |
| CDK2 | 19.90 | 19.20 | 18.38 | 17.19 | 2.11 | 2.37 |
| CDK4 | 20.75 | 20.78 | 19.83 | 19.42 | 1.28 | 1.38 |
| CDK6 | 19.85 | 18.27 | 19.81 | 18.02 | 3.89 | 3.59 |
| CDKN1A | 14.70 | 12.52 | 15.60 | 13.20 | 5.92 | 5.48 |
| CDKN2A | 21.65 | 20.93 | 19.62 | 18.40 | 2.14 | 2.42 |
| CDKN2D | 22.47 | 21.10 | 22.24 | 20.57 | 3.36 | 3.28 |
| CHEK1 | 19.35 | 18.85 | 19.37 | 18.53 | 1.84 | 1.85 |
| CHEK2 | 20.31 | 19.55 | 22.22 | 20.94 | 2.20 | 2.52 |
| E2F1 | 19.84 | 19.68 | 21.10 | 20.31 | 1.45 | 1.79 |
| E2F3 | 22.13 | 22.26 | 22.39 | 22.06 | 1.19 | 1.30 |
| ETS1 | 20.05 | 19.23 | 19.91 | 18.10 | 2.30 | 3.63 |
| ETS2 | 19.33 | 18.09 | 19.46 | 18.01 | 3.06 | 2.83 |
| MDM2 | 19.08 | 17.24 | 19.18 | 17.05 | 4.65 | 4.52 |
| RB1 | 22.22 | 24.77 | 22.43 | 24.38 | 0.22 | 0.27 |
| RBL2 | 24.28 | 23.39 | 21.33 | 19.87 | 2.41 | 2.86 |
| TP53 | 22.90 | 20.37 | 19.78 | 16.82 | 7.52 | 8.08 |
| TWIST1 | 20.32 | 22.97 | 20.05 | 20.33 | 0.21 | 0.85 |
| p53 and pRb Signaling | | | | | | |
| ABL1 | 19.42 | 19.39 | 18.66 | 18.33 | 1.33 | 1.31 |
| AKT1 | 18.00 | 19.65 | 18.01 | 18.19 | 0.41 | 0.91 |
| ALDH1A3 | 21.52 | 20.80 | 19.47 | 18.20 | 2.14 | 2.49 |
| CCNA2 | 18.65 | 19.02 | 18.55 | 18.69 | 1.01 | 0.94 |
| CCNB1 | 19.15 | 18.94 | 18.62 | 18.10 | 1.51 | 1.48 |
| CDC25C | 23.66 | 23.33 | 21.39 | 21.64 | 1.64 | 0.87 |
| CDKN1C | 22.54 | 20.85 | 20.57 | 18.46 | 4.20 | 4.47 |
| CDKN2B | 21.52 | 19.11 | 22.29 | 19.42 | 6.93 | 7.58 |
| CDKN2C | 22.47 | 20.53 | 22.16 | 19.83 | 5.01 | 5.19 |
| CITED2 | 16.11 | 15.04 | 18.10 | 16.60 | 2.74 | 2.93 |
| CREG1 | 21.46 | 20.14 | 22.60 | 20.98 | 3.26 | 3.18 |
| GSK3B | 21.08 | 18.38 | 20.85 | 17.76 | 8.43 | 8.80 |
| ID1 | 18.04 | 17.97 | 17.58 | 17.18 | 1.37 | 1.37 |
| IGFBP3 | 17.34 | 18.15 | 18.61 | 18.84 | 0.74 | 0.88 |
| ING1 | 21.45 | 21.14 | 21.07 | 21.13 | 1.62 | 0.99 |
| MAP2K6 | 26.22 | 26.07 | 26.14 | 26.11 | 1.44 | 1.06 |
| MAPK14 | 20.38 | 18.48 | 20.81 | 18.52 | 4.87 | 5.04 |
| MORC3 | 21.08 | 20.48 | 21.68 | 20.94 | 1.97 | 1.73 |
| MYC | 20.36 | 20.07 | 21.10 | 20.31 | 1.58 | 1.79 |
| PCNA | 15.50 | 17.78 | 17.30 | 19.16 | 0.27 | 0.29 |
| PIK3CA | 20.47 | 20.55 | 19.97 | 19.59 | 1.23 | 1.34 |
| PLAU | 17.88 | 16.53 | 16.35 | 14.63 | 3.32 | 3.40 |
| RBL1 | 22.61 | 22.83 | 21.66 | 22.03 | 1.12 | 0.80 |
| SERPINB2 | 22.23 | 21.01 | 22.67 | 21.14 | 3.03 | 3.00 |
| SERPINE1 | 16.24 | 14.34 | 16.59 | 14.32 | 4.87 | 5.00 |
| SIRT1 | 20.62 | 18.53 | 21.31 | 18.72 | 5.54 | 6.23 |
| SPARC | 12.47 | 11.38 | 13.80 | 12.39 | 2.77 | 2.75 |
| TGFB1 | 18.47 | 16.63 | 18.07 | 15.78 | 4.64 | 5.08 |
| Interferon-related | | | | | | |
| ALDH1A3 | 21.52 | 20.80 | 19.47 | 18.20 | 2.14 | 2.49 |
| CDKN1A | 14.70 | 12.52 | 15.60 | 13.20 | 5.92 | 5.48 |
| CDKN1B | 18.71 | 17.75 | 20.04 | 18.74 | 2.52 | 2.55 |
| EGR1 | 19.55 | 18.59 | 19.83 | 18.72 | 2.54 | 2.24 |
| IFNG | 24.46 | 24.20 | 24.78 | 24.32 | 1.56 | 1.42 |

TABLE 1-continued

Table 1. qRT-PCR array for Senescence pathways.

| | C(t) of Sc in Exp. 1 | C(t) of LB1sh in Exp. 1 | C(t) of Sc in Exp. 2 | C(t) of LB1sh in Exp. 2 | Ave. LB1sh/ Sc in Exp. 1 | Ave. LB1sh/ Sc in Exp. 2 |
|---|---|---|---|---|---|---|
| IGFBP3 | 17.34 | 18.15 | 18.61 | 18.84 | 0.74 | 0.88 |
| IGFBP7 | 15.39 | 14.48 | 14.87 | 13.60 | 2.45 | 2.49 |
| IRF3 | 19.47 | 18.34 | 19.42 | 17.76 | 2.85 | 3.27 |
| IRF5 | 28.01 | 28.13 | 24.77 | 24.68 | 1.19 | 1.10 |
| IRF7 | 23.08 | 23.17 | 22.29 | 21.92 | 1.22 | 1.33 |
| NFKB1 | 25.27 | 25.17 | 25.05 | 24.25 | 1.39 | 1.79 |
| RB1 | 22.22 | 24.77 | 22.43 | 24.38 | 0.22 | 0.27 |
| SERPINB2 | 22.23 | 21.01 | 22.67 | 21.14 | 3.03 | 3.00 |
| Insulin Growth Factor Related | | | | | | |
| IGF1 | 31.18 | 31.58 | 29.71 | 29.61 | 0.99 | 1.12 |
| IGF1R | 25.98 | 25.63 | 23.84 | 23.75 | 1.66 | 1.10 |
| IGFBP3 | 17.34 | 18.15 | 18.61 | 18.84 | 0.74 | 0.88 |
| IGFBP5 | 14.69 | 13.41 | 13.64 | 12.11 | 3.15 | 3.00 |
| IGFBP7 | 15.39 | 14.48 | 14.87 | 13.60 | 2.45 | 2.49 |
| Mitogen-related | | | | | | |
| HRAS | 19.25 | 19.21 | 19.19 | 19.10 | 1.34 | 1.10 |
| MAP2K1 | 24.75 | 23.29 | 24.07 | 22.15 | 3.57 | 3.89 |
| MAP2K3 | 17.63 | 17.68 | 18.27 | 18.08 | 1.26 | 1.18 |
| MAP2K6 | 26.22 | 26.07 | 26.14 | 26.11 | 1.44 | 1.06 |
| MAPK14 | 20.38 | 18.48 | 20.81 | 18.52 | 4.87 | 5.04 |
| Oxidative Stress | | | | | | |
| ALDH1A3 | 21.52 | 20.80 | 19.47 | 18.20 | 2.14 | 2.49 |
| HRAS | 19.25 | 19.21 | 19.19 | 19.10 | 1.34 | 1.10 |
| MAPK14 | 20.38 | 18.48 | 20.81 | 18.52 | 4.87 | 5.04 |
| NOX4 | 25.51 | 23.36 | 23.63 | 21.07 | 5.77 | 6.10 |
| PRKCD | 21.59 | 21.10 | 21.75 | 21.06 | 1.83 | 1.68 |
| SOD1 | 17.36 | 16.14 | 17.63 | 16.10 | 3.02 | 2.99 |
| SOD2 | 17.35 | 16.53 | 17.37 | 16.25 | 2.29 | 2.25 |
| DNA Damage | | | | | | |
| ATM | 23.56 | 22.53 | 21.14 | 19.84 | 2.67 | 2.55 |
| GADD45A | 21.32 | 20.21 | 19.48 | 18.15 | 2.80 | 2.60 |
| NBN | 23.30 | 22.90 | 22.04 | 21.58 | 1.72 | 1.42 |
| PCNA | 15.50 | 17.78 | 17.30 | 19.16 | 0.27 | 0.29 |
| TERF2 | 19.14 | 19.09 | 19.40 | 19.23 | 1.35 | 1.16 |
| TERT | 37.95 | 38.07 | 38.96 | 38.96 | 1.20 | 1.04 |
| TP53BP1 | 21.83 | 19.46 | 20.29 | 17.38 | 6.73 | 7.75 |
| P53 Effectors | | | | | | |
| ALDH1A3 | 21.52 | 20.80 | 19.47 | 18.20 | 2.14 | 2.49 |
| E2F1 | 19.84 | 19.68 | 21.10 | 20.31 | 1.45 | 1.79 |
| HRAS | 19.25 | 19.21 | 19.19 | 19.10 | 1.34 | 1.10 |
| IGFBP3 | 17.34 | 18.15 | 18.61 | 18.84 | 0.74 | 0.88 |
| MYC | 20.36 | 20.07 | 21.10 | 20.31 | 1.58 | 1.79 |
| p21 Effectors | | | | | | |
| CALR | 14.37 | 14.02 | 14.40 | 14.17 | 1.66 | 1.21 |
| p16 Effectors | | | | | | |
| TBX2 | 18.84 | 19.12 | 19.22 | 19.09 | 1.07 | 1.14 |
| TBX3 | 18.40 | 19.07 | 19.28 | 19.75 | 0.82 | 0.75 |
| Cytoskeleton-related | | | | | | |
| AKT1 | 18.00 | 19.65 | 18.01 | 18.19 | 0.41 | 0.91 |
| FN1 | 13.17 | 12.30 | 13.74 | 12.43 | 2.38 | 2.57 |
| HRAS | 19.25 | 19.21 | 19.19 | 19.10 | 1.34 | 1.10 |
| PIK3CA | 20.47 | 20.55 | 19.97 | 19.59 | 1.23 | 1.34 |
| PLAU | 17.88 | 16.53 | 16.35 | 14.63 | 3.32 | 3.40 |
| SERPINE1 | 16.24 | 14.34 | 16.59 | 14.32 | 4.87 | 5.00 |
| SPARC | 12.47 | 11.38 | 13.80 | 12.39 | 2.77 | 2.75 |
| THBS1 | 15.45 | 12.93 | 15.85 | 13.43 | 7.46 | 5.54 |
| VIM | 16.08 | 16.06 | 15.40 | 15.05 | 1.32 | 1.31 |
| Cell Adhesion | | | | | | |
| CD44 | 13.42 | 13.52 | 14.44 | 14.10 | 1.21 | 1.31 |
| COL1A1 | 10.42 | 10.54 | 10.88 | 10.68 | 1.20 | 1.19 |
| COL3A1 | 17.22 | 17.55 | 17.95 | 17.57 | 1.04 | 1.34 |
| TGFB1 | 18.47 | 16.63 | 18.07 | 15.78 | 4.64 | 5.08 |
| TGFB1I1 | 17.87 | 16.14 | 17.37 | 15.31 | 4.29 | 4.34 |
| THBS1 | 15.45 | 12.93 | 15.85 | 13.43 | 7.46 | 5.54 |
| Others | | | | | | |
| GLB1 | 22.24 | 19.76 | 21.73 | 18.84 | 7.28 | 7.67 |
| PTEN | 19.96 | 18.94 | 19.29 | 18.14 | 2.64 | 2.31 |

Figure 4:
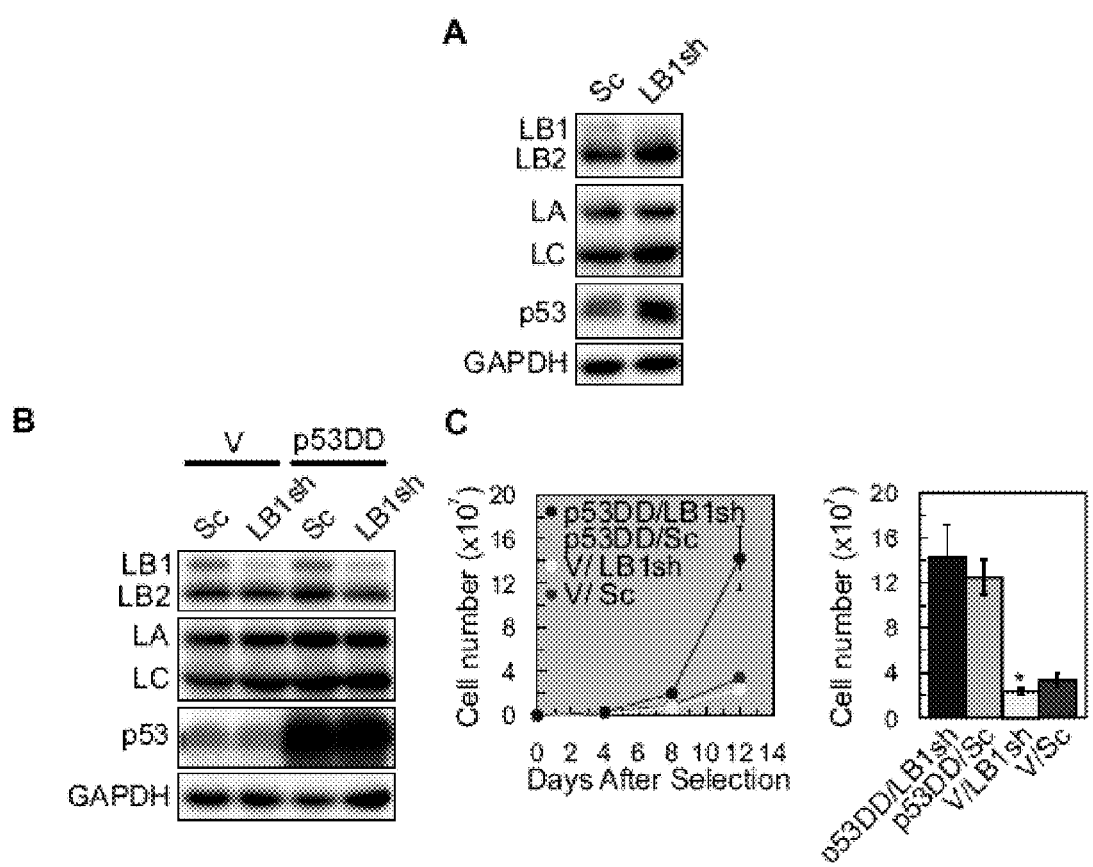
FIG. 4 shows p53 but not pRb is required for the inhibition of cell proliferation by LB1 silencing. (A) WI-38 cells (PD24) were transfected with either the LB1sh or Sc vector. Six days after selection the expression levels of LB1, LB2, LA/C, and p53 were determined by immunoblotting. (B-G) The requirements of the p53 and pRb pathways for the LB1 silencing effects on cell proliferation were examined. (B) Cells were transfected with either a p53 deletion mutant (p53DD) or a control vector (V), and then transfected with either LB1sh or Sc. (C) The graph shows that expression of p53DD resulted in increased proliferation and that there was no significant difference between p53DD/Sc (green) and p53DD/LB1sh (blue) (n=3; p=3.2×10−1) but there was a change in proliferation between cells expressing V/Sc (red) and V/LB1sh (yellow) (n=3; *p=8.0×10−3). (D) Cells were transfected with either a p53 shRNA vector (p53sh) or a control vector (V), and then transfected with either LB1sh or Sc. (E) The graph shows that proliferation increased in cells with less p53 expression, and that there was no significant difference in proliferation between p53sh/LB1sh (blue) and p53sh/Sc (green) (n=3; p=9.7×10−1), but there was a significant difference between V/LB1sh (yellow) and V/Sc (red) (n=3; *p=5.7×10−4). The error bars for p53sh/LB1sh and p53sh/Sc overlap. (F) Cells were transfected with either a HPV E7 vector or a control vector (V), and then transfected with either LB1sh or Sc. Non-phosphorylated and phosphorylated pRb are indicated as non-p-pRb and p-pRb, respectively. (G) Thegraph shows that the proliferation of V/LB1sh (yellow) decreased compared to V/Sc (red) controls (n=3; *p=7.9×10−3). The rates of cell proliferation increased in E7/LB1sh and E7/Sc cells compared to V/LB1sh and V/Sc cells; there were even greater increases in the E7/Sc (green) compared to E7/LB1sh (blue) (n=3; *p=1.6×10−2). For clarity the data from day 12 following selection are also displayed as histograms in C, E and G. No significant changes in LB2 and LA/C protein levels were detected in any of the cells examined. GAPDH was used as a loading control. Error bars in graphs represent standard deviations. The bars with an asterisk mark experiments with significant changes (*p<5.0×10−2).
Figure 4:
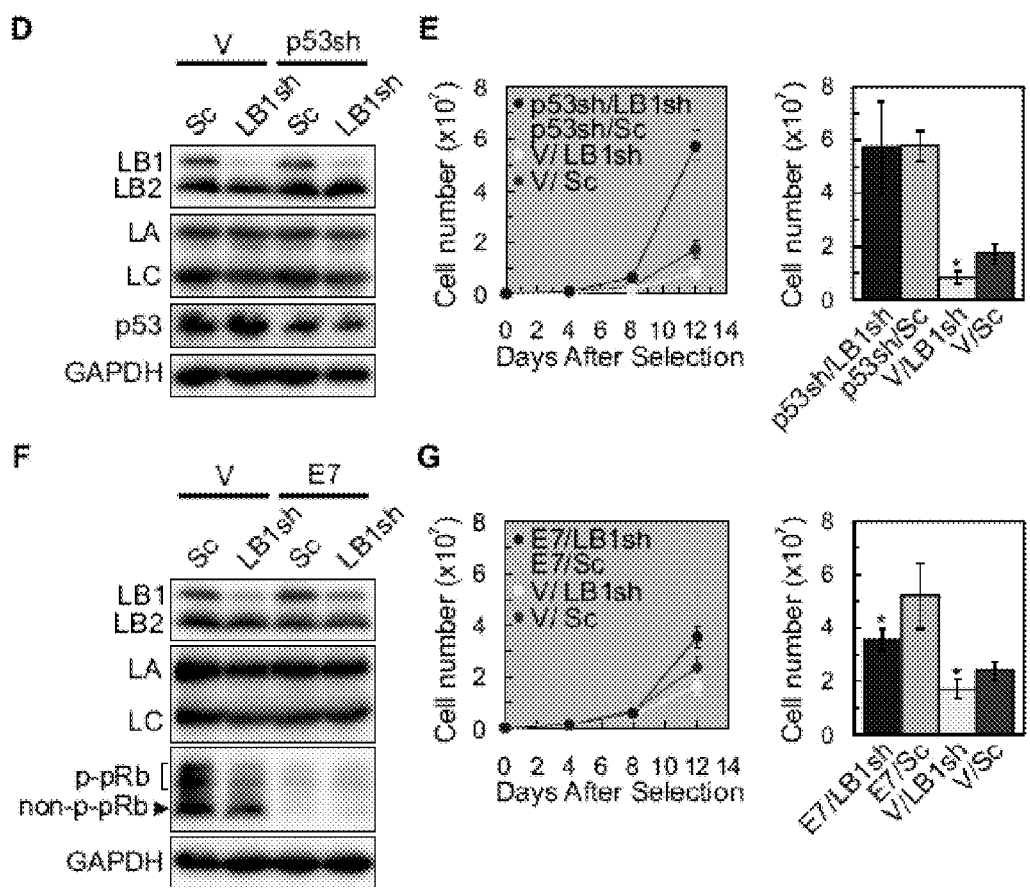

The involvement of the p53 pathway in the LB1 silencing effects was examined using immunoblotting to measure p53 levels in whole cell lysates prepared 6 days after selection. LB1 silencing caused a ~39% increase in p53 compared to Sc (FIG. 4A). At 3 days following selection, the transcript levels of the p53 gene, TP53, increased ~7.5-fold and the transcript levels of the mediator of p53-dependent senescence, p21 (CDKN1A) increased ~6-fold over control levels (Table 1). The contribution of p53 to proliferation and senescence was investigated by expressing the p53 mini-protein p53DD and subsequently silencing LB1. p53DD inactivates p53 and prevents its degradation (Shaulian et al. 1992) as evidenced by increased levels of p53 in p53DD expressing cells (FIG. 4B). When p53 was inactivated by p53DD expression, the proliferation rates of both LB1sh and Sc cells were increased (FIG. 4C), with no significant differences between the two detected within 12 days (FIG. 4C). In addition, no differences in the numbers of cells with SAHFs, staining for SA-β-gal or incorporating BrdU were detected. Similarly, in cells where p53 was down regulated by shRNA, there was no significant difference in proliferation between Sc and LB1 silenced cell regulated by shRNA, there was no significant difference in proliferation between Sc and LB1 silenced cells (FIGS. 4D and E). Therefore, a functional p53 pathway is required for both the decreased proliferation rate and the induction of premature senescence caused by LB1 silencing.

The involvement of the pRb pathway in the effects of LB1 silencing was analyzed by immunoblotting of whole cell lysates prepared 6 days after selection. LB1 silencing caused a 71% decrease in nonphosphorylated pRb and a 75% decrease in phospho-pRb as compared to controls (FIG. 4F, left 2 lanes) (DeCaprio et al. 1989). In addition, the level of RB1 transcripts was decreased by ~5-fold by 3 days following selection (Table 1). The contribution of pRb to proliferation and senescence was investigated by expression of the HPV oncoprotein E7 to induce pRb degradation (FIG. 4F) (Boyer et al. 1996). E7 was used in this experiment rather than E1A (see FIG. 2B) since it specifically inhibits the Rb family and does not sensitize the cells to apoptosis as is the case with E1A (Deng et al. 2005). In our hands, attempts to silence LB1 in E1Aexpressing cells led to increased apoptosis with both the LB1 silencing and control vectors. When LB1 was silenced in E7 expressing cells, both silenced and Sc cells showed increased proliferation rates relative to non-E7 expressing cells (FIG. 4G). However the proliferation rates of LB1 silenced cells was consistently slower than Sc cells whether or not pRb was inactivated (FIG. 4G). This slower proliferation was not attributable to apoptosis, as determined by the TUNEL reaction. Additionally, E7 expressing cells did not become senescent as evidenced by continuous proliferation and the lack of senescence marks. These results demonstrate that the pRb pathway is not required for the decreased proliferation induced by LB1 silencing. However pRb is required for LB1 silenced cells to become prematurely senescent.

Example 6

The Decrease in Cell Proliferation Accompanying LB1 Silencing is Independent of Telomere Dysfunction The requirement for activation of p53 for the slow proliferation and premature senescence induced by LB1 silencing suggests that LB1 has a role in the maintenance of cell proliferation upstream of the p53 pathway. One possible upstream process involving LB1 is telomere dysfunction. Although there is no known relationship between LB1 and telomeres, it has been shown that the A-type lamins are involved in the maintenance of telomeres (Gonzalez-Suarez et al. 2009) and that dysfunctional telomeres are associated with DNA damage foci as marked by γH2AX (d'Adda di Fagagna et al. 2003). Therefore, the association between γH2AX foci and telomeres was examined by immunofluorescence 3 and 6 days after selection of LB1 silenced cells. The majority of LB1sh and Sc cells contained only 1 or 2 of the large γH2AX foci (FIG. S2A) typically associated with sites of DNA damage (d'Adda di Fagagna et al. 2003). The association of telomeres with γH2AX foci was examined by fluorescence in situ hybridization combined with immunofluorescence (Immuno-FISH). The results showed no colocalization between telomeres and γH2AX foci in LB1sh cells (FIG. S2B). Furthermore, no significant changes in telomere length could be detected as assayed by telomere restriction fragment analyses on DNA isolated from LB1 silenced and control cells at both 3 and 6 days following selection (FIG. S2C). These results demonstrate that telomere dysfunctions are not major contributors to the premature senescence induced by LB1 silencing.

Example 7

Figure 5:
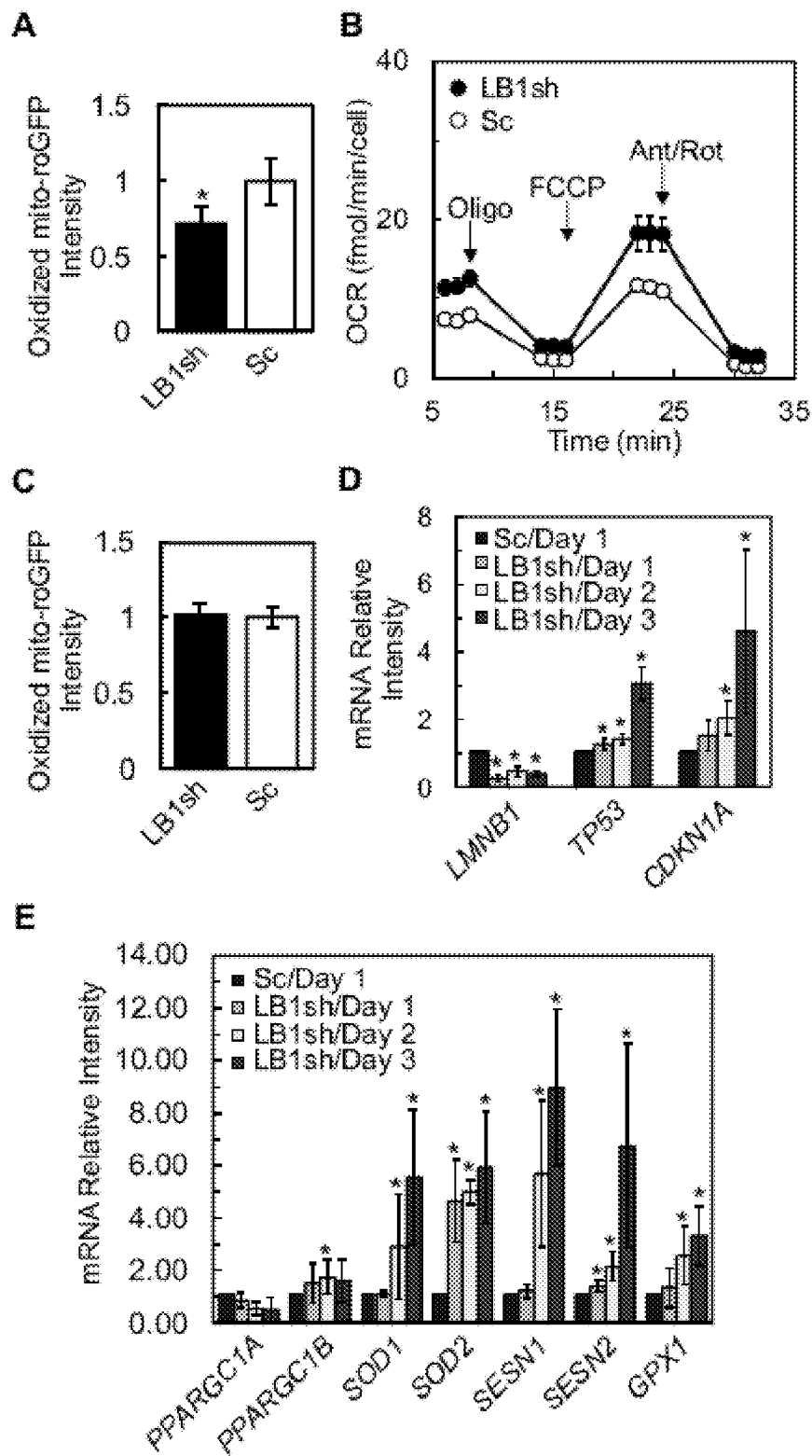
FIG. 5 shows the effects of LB1 silencing on mitochondrial ROS. Expression of roGFP was examined in WI-38 cells 3 days after selection for cells expressing either LB1sh or Sc. (A) Flow cytometric analysis indicates that LB1sh reduces the amount of oxidized roGFP. The black and white bars indicate the normalized mean oxidation of roGFP in LB1sh and Sc cells, respectively (n=6, *p=1.6×10−2). (B) Oxygen consumption rate (OCR) was measured in LB1sh and Sc cells incubated in basal medium and subsequently exposed to oligomycin (oligo) for ATP inhibition, carbonyl cyanide p-trifluoromethoxyphenylhydrazone (FCCP) for mitochondrial uncoupling, and antimycin A/rotenone (Ant/Rot) for inhibiting electron transfer in complex I and III (see Materials and Methods). There was a significant difference between LB1sh and Sc cells (*p=5.6×10−4, 3.4×10−5, 6.6×10−6 and 2.2×10−3), respectively. The bars represent the standard errors of the mean. (C) Expression of p53DD inhibits the decrease in roGFP in LB1sh cells. There was no significant difference in the amount of oxidized roGFP between LB1sh and Sc (n=6; p=6.5×10−1). (D) The levels of transcripts (mRNAs) of the LB1 gene (LMNB1), the p53 gene (TP53) and the p21 gene (CDKN1A) were determined in LB1sh and Sc cells by quantitative PCR every 24 hrs for 3 days after selection (n=4; *p<5.0×10−2 between Sc and LB1sh at day 1, 2 and 3). (E) The levels of transcripts (mRNAs) of the SOD1 (SOD1), SOD2 (SOD2), sestrin 1 (SESN1), sestrin 2 (SESN2), GPX1 (GPX1), PGC-1α (PPARGC1A) and PGC-1β (PPARGC1B) genes in LB1sh and Sc cells were determined by quantitative PCR every 24 hrs for 3 days after selection (n=4; *p<5.0×10−2 between Sc and LB1sh at day 1, 2 and 3). The error bars in A, C, D and E represent standard deviations. The bars with an asterisk mark experiments with significant changes (*p<5.0×10−2).

LB1 Silencing Inhibits Cell Proliferation Through a Reactive Oxygen Species (ROS) Signaling Pathway Another upstream event that acts through the p53 pathway to induce premature senescence is the production of abnormally high levels of reactive oxygen species (ROS) (Finkel and Holbrook 2000). To determine if increased ROS levels were a possible cause of the premature senescence in LB1 silenced cells, a mitochondrial matrix-targeted redox-sensitive green fluorescent protein, roGFP, was expressed (Dooley et al. 2004). In order to minimize the normal accumulation of mitochondrial ROS as cells approach senescence (Hagen et al. 1997), the analyses were carried out 3 days after selection for LB1 silencing at which time LB1sh cells showed no changes in senescence markers. Mitochondrial ROS was determined by roGFP fluorescence using flow cytometry. Surprisingly, there was a ~28% (n=6) decrease in ROS in LB1 silenced cells compared to controls (FIG. 5A). These results were confirmed using another ROS indicator, carboxy-H2DCFDA (FIG. S3A). Since mitochondrial oxidative phosphorylation is a major source of ROS in non-transformed cells, the oxygen consumption rate (OCR) of LB1 silenced and control cells was measured (Weinberg et al. 2010). LB1 silenced cells exhibited an increased OCR (FIG. 5B), but no change in mitochondrial mass (FIG. S3B), suggesting that the oxidative capacity of individual mitochondria was increased.

The decrease in ROS in LB1 silenced cells even as oxygen consumption was increased suggested that LB1 silencing may up regulate genes involved in the antioxidant response. Since p53 is activated by LB1 silencing and p53 regulates anti-oxidant genes (Sablina et al. 2005), the role of p53 in mediating the decrease in ROS in LB1 silenced cells was investigated. The results showed no reduction in ROS in LB1sh cells expressing p53DD (FIG. 5C), demonstrating that activation of p53 was required for the decrease in ROS. Other evidence supporting the activation of p53 after LB1 silencing was obtained by measuring the mRNA levels of p53 (TP53) and the p53-target gene p21 (CDKN1A) by qRT-PCR every 24 hours beginning immediately after selection. The mRNA levels of both genes gradually increased after LB1 silencing (FIG. 5D), indicating that the p53-p21 pathway was activated by LB1 silencing within 3 days after selection. In addition, the human cellular senescence PCR array data showed that other p53 target genes such as PAI-1 (SERPINE1) were up regulated (Table 1). Furthermore, several p53-target genes involved in the antioxidant response including superoxide dismutase1 and 2 (SOD1 and SOD2), sestrin 1/PA26 (SESN1), sestrin 2/Hi95 (SESN2) and glutathione peroxidase 1 (GPX1) (Hussain et al. 2004; Sablina et al. 2005; Lebedeva et al. 2009; Spanier et al. 2009) were also analyzed by qRT-PCR during the first 3 days after selection. The transcript levels of each of these genes increased by ~3-8 fold in LB1sh compared to Sc cells in a time dependent fashion (FIG. 5E). Interestingly, transcription of SOD2 increased much earlier than the responses of the other antioxidant genes (FIG. 5E). In addition, two p53 regulated factors involved in regulating mitochondrial biogenesis, peroxisome proliferator activated receptor gamma 1α and β (PGC-1α and PGC-1β; PPARGC1A and 1B) were examined (Sahin et al. 2011). No significant changes in transcription of these factors were detected, consistent with the observation that mitochondrial mass did not change in LB1sh cells (FIGS. 5E and S3). Taken together, these qRT-PCR analyses further demonstrate that LB1 silencing results in the reduction of mitochondrial ROS due to the activation of antioxidant genes regulated by p53.

Figure 6:
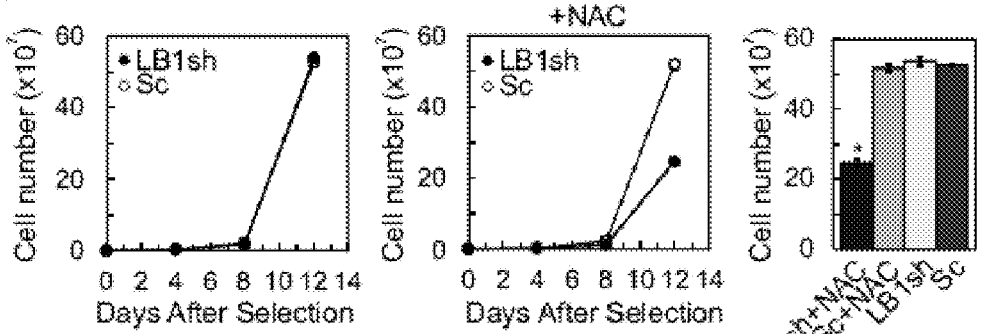
FIG. 6 shows hypoxia rescues the slow proliferation induced by LB1 silencing. (A) Proliferation of LB1sh and Sc cells under hypoxic conditions (1.5% O2) in the presence or absence of NAC during selection and for 12 days after selection (see Materials and Methods; n=3, p=8.5×10−1 between Sc and LB1sh; *p=3.2×10−2 between Sc/NAC and LB1sh/NAC). NAC treatment slowed proliferation in LB1sh (LB1sh/NAC) relative to non-treated LB1sh (n=3; *p=2.3×10−3). (B) Proliferation of LB1sh and Sc cells grown under normoxic conditions (21% O2) in the presence or absence of NAC during and for 12 days after selection (see Materials and Methods; n=3, *p=3.8×10−3 for the difference between Sc (red) and LB1sh (yellow); *p=1.3×10−4 for the difference between Sc/NAC (green) and LB1sh/NAC (blue)). NAC treatment slowed proliferation in LB1sh (LB1sh/NAC) compared to non-treated LB1sh (n=3; *p=2.3×10−3). The histograms in FIGS. 6A and B show the cell numbers at 12 days after selection. Error bars in graphs represent standard deviations. The bars with an asterisk mark experiments with significant changes (*p<5.0×10−2).
Figure 6:
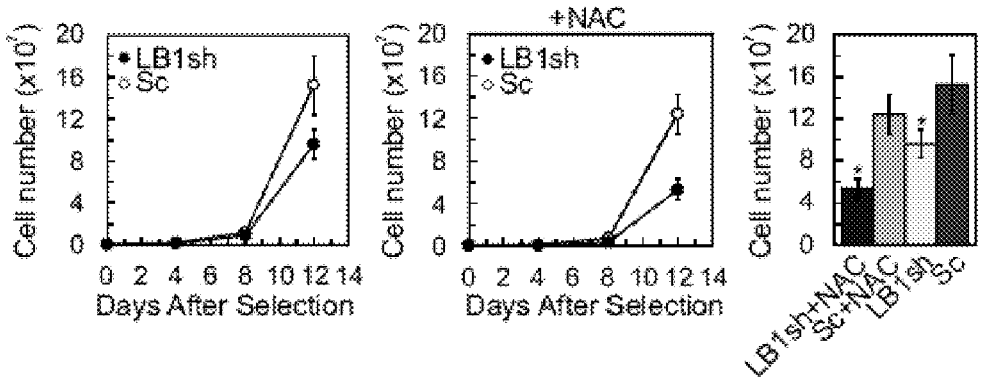

The rapid decrease in ROS following the initiation of LB1 silencing suggested that increasing the levels of ROS might rescue the reduced proliferation caused by the loss of LB 1. In support of this, several studies have shown that hypoxia (1.5% O2) causes moderate increases in ROS and promotes the proliferation and longevity of HDFs in culture (Packer and Fuehr 1977; Bell et al. 2007). Therefore it was determined that the proliferation rates of LB1 silenced and control cells under hypoxic conditions. The results showed that the rates of proliferation of LB1sh and Sc cells were indistinguishable (FIG. 6A, left and right) and both were faster than cells grown in normoxic conditions (FIG. 6B, left). In order to demonstrate the specific contribution of ROS to the rate of proliferation in LB1sh cells under hypoxic conditions, a ROS scavenger, N-acetyl-L-cysteine (NAC), was added to the cultures (Sekharam et al. 1998). Under these conditions, only the LB1sh cells showed decreased rates of proliferation (FIG. 6A, middle and right), suggesting that LB1sh cells are more sensitive than control cells to hypoxia induced increases in ROS.

Both NAC treated LB1sh and Sc cells grown under normoxic (21% O2) conditions exhibited slower proliferation rates than untreated cells (FIG. 6B, left and middle). Importantly, NAC treatment slowed proliferation of LB1sh cells to an even greater extent than the proliferation of non-treated LB1sh cells (FIG. 6B, right). Based upon these observations it was also determined whether NAC treatment accelerated entry into senescence under normoxic conditions. At 8 days following selection, the number of cells positive for SA-β-gal increased with NAC treatment (~15% [n=450] for LB1sh; ~22% [n=432] for LB1sh with NAC; ~3.4% [n=500] for Sc; ~7% [n=430] for Sc with NAC); and SAHFs (~14% [n=594] for LB1sh; ~21% [n=584] for LB1sh with NAC; ~0.5% [n=769] for Sc; ~5% [n=658] for Sc with NAC). There was also a decrease in cells incorporating BrdU (~18% [n=707] for LB1sh; ~11% [n=906] for LB1sh with NAC; ~39% [n=779] for Sc; ~27% [n=738] for Sc with NAC). Taken together, the results of silencing LB1 expression under hypoxic or normoxic conditions suggest that a ROS signaling pathway is responsible for the effects of silencing on proliferation and induction of the senescence program.

Example 7

Over Expression of LB1 Increases the Proliferation Rate and Arrests Cells in the G1 Phase of the Cell Cycle Since LB1 silencing slowed the proliferation rate and induced the premature senescence of WI-38 cells, it seemed plausible that the over-expression of LB1 might affect the proliferation rate and the onset of senescence. To test these possibilities, GFP-LB1 was expressed in WI-38 cells at PD24 and cell proliferation was monitored. The expression levels of LA/C, LB1 and LB2 in cells expressing GFP-LB1 were analyzed by fluorescence microscopy and immunoblotting 14 days after selection (FIG. 7A-B). There were no significant changes in the expression of endogenous LA/C, LB1 and LB2 in either GFP-LB1 expressing cells or in controls expressing only GFP (FIG. 7B). The amount of GFP-LB1 expressed was ~10 to 15-fold greater than the level of endogenous LB1 (FIG. 7B). The two bands migrating near the predicted molecular weight of GFP-LB1 probably represent the farnesylated and non-farnesylated forms of the protein (Maske et al. 2003). This accumulation could be attributable to the overexpression of the non-farnesylated form which likely overwhelms the lamin processing enzymes (our unpublished observations). The lower molecular weight bands seen in the GFP-LB1 expressing cells have been reported in HDFs expressing different types of GFP-fusion proteins (Narita et al. 2006). These bands probably represent prematurely truncated or incompletely translated proteins due to overexpression. Importantly, the average proliferation rate of the GFP-LB1 expressing cells was ~1.4 times faster than that of GFP-expressing control cells in the time period between 18 and 34 days after selection (see Materials and Methods, FIGS. 7C; and S4). Flow cytometric analyses of the cells at the time they stopped proliferating (53 days after selection) showed that ~80% of both the GFP-LB1 expressing cells and the controls were in G1, which is consistent with senescence (FIG. 7D; (Campisi and d'Adda di Fagagna 2007)). Since LB1 silenced cells exhibit reduced pRb phosphorylation (see FIG. 4D), the phosphorylation state of pRb was examined in the GFP-LB1 expressing cells at day 53. Surprisingly, there was a 9-fold increase in both pRb and in phospho-pRb in GFP-LB1 expressing compared to GFP-expressing cells (FIG. 7E). These results show that over-expression of LB1 increases the rate of proliferation and delays the onset of senescence of HDFs.

REFERENCES

All publications and patents listed below and/or mentioned in the above specification are herein incorporated by reference in their entireties.

Aebi U, Cohn J, Buhle L, Gerace L. 1986. The nuclear lamina is a meshwork of intermediate-type filaments. *Nature* 323: 560-564.

Atamna H, Paler-Martinez A, Ames B N. 2000. N-t-butyl hydroxylamine, a hydrolysis product of alpha-phenyl-N-t-butyl nitrone, is more potent in delaying senescence in human lung fibroblasts. *The Journal of biological chemistry* 275: 6741-6748.

Behrend L, Mohr A, Dick T, Zwacka R M. 2005. Manganese superoxide dismutase induces p53-dependent senescence in colorectal cancer cells. *Molecular and cellular biology* 25: 7758-7769.

Bell E L, Klimova T A, Eisenbart J, Schumacker P T, Chandel N S. 2007. Mitochondrial reactive oxygen species trigger hypoxia-inducible factor-dependent extension of the replicative life span during hypoxia. *Molecular and cellular biology* 27: 5737-5745.

Boyer S N, Wazer D E, Band V. 1996. E7 protein of human papilloma virus-16 induces degradation of retinoblastoma protein through the ubiquitin-proteasome pathway. *Cancer research* 56: 4620-4624.

Burkhart D L, Sage J. 2008. Cellular mechanisms of tumour suppression by the retinoblastoma gene. *Nat Rev Cancer* 8: 671-682.

Campisi J, d'Adda di Fagagna F. 2007. Cellular senescence: when bad things happen to good cells. *Nat Rev Mol Cell Biol* 8: 729-740.

Cao K, Blair C D, Faddah D A, Kieckhaefer J E, Olive M, Erdos M R, Nabel E G, Collins F S. 2011. Progerin and telomere dysfunction collaborate to trigger cellular senescence in normal human fibroblasts. *The Journal of clinical investigation* 121: 2833-2844.

Coffinier C, Chang S Y, Nobumori C, Tu Y, Farber E A, Toth J I, Fong L G, Young S G. 2010. Abnormal development of the cerebral cortex and cerebellum in the setting of lamin B2 deficiency. *Proceedings of the National Academy of Sciences of the United States of America* 107: 5076-5081.

Coffinier C, Jung H J, Nobumori C, Chang S, Tu Y, Barnes R H, 2nd, Yoshinaga Y, de Jong P J, Vergnes L, Reue K et al. 2011. Deficiencies in lamin B1 and lamin B2 cause neurodevelopmental defects and distinct nuclear shape abnormalities in neurons. *Molecular biology of the cell.*

Coller H A. 2007. What's taking so long? S-phase entry from quiescence versus proliferation. *Nat Rev Mol Cell Biol* 8: 667-670.

d'Adda di Fagagna F, Reaper P M, Clay-Farrace L, Fiegler H, Can P, Von Zglinicki T, Saretzki G, Carter N P, Jackson S P. 2003. A DNA damage checkpoint response in telomere-initiated senescence. *Nature* 426: 194-198.

DeCaprio J A, Ludlow J W, Lynch D, Furukawa Y, Griffin J, Piwnica-Worms H, Huang C M, Livingston D M. 1989. The product of the retinoblastoma susceptibility gene has properties of a cell cycle regulatory element. *Cell* 58: 1085-1095.

Dechat T, Pfleghaar K, Sengupta K, Shimi T, Shumaker D K, Solimando L, Goldman R D. 2008. Nuclear Lamins: Major Factors in the Structural Organization and Function of the Nucleus and Chromatin. *Genes and Development* 22: 832-853.

Deng Q, Li Y, Tedesco D, Liao R, Fuhrmann G, Sun P. 2005. The ability of E1A to rescue ras-induced premature senescence and confer transformation relies on inactivation of both p300/CBP and Rb family proteins. *Cancer research* 65: 8298-8307.

Dimri G P, Lee X, Basile G, Acosta M, Scott G, Roskelley C, Medrano E E, Linskens M, Rubelj I, Pereira-Smith O et al. 1995. A biomarker that identifies senescent human cells in culture and in aging skin in vivo. *Proceedings of the National Academy of Sciences of the United States of America* 92: 9363-9367.

Dooley C T, Dore T M, Hanson G T, Jackson W C, Remington S J, Tsien R Y. 2004. Imaging dynamic redox changes in mammalian cells with green fluorescent protein indicators. *The Journal of biological chemistry* 279: 22284-22293.

Dorner D, Gotzmann J, Foisner R. 2007. Nucleoplasmic lamins and their interaction partners, LAP2alpha, Rb, and BAF, in transcriptional regulation. *Febs J* 274: 1362-1373.

Finkel T, Holbrook N J. 2000. Oxidants, oxidative stress and the biology of ageing. *Nature* 408: 239-247.

Forsyth N R, Evans A P, Shay J W, Wright W E. 2003. Developmental differences in the immortalization of lung fibroblasts by telomerase. *Aging cell* 2: 235-243.

Gjoerup O V, Wu J, Chandler-Militello D, Williams G L, Zhao J, Schaffhausen B, Jat P S, Roberts T M. 2007. Surveillance mechanism linking Bub1 loss to the p53 pathway. *Proceedings of the National Academy of Sciences of the United States of America* 104: 8334-8339.

Goldman R D, Shumaker D K, Erdos M R, Eriksson M, Goldman A E, Gordon L B, Gruenbaum Y, Khuon S, Mendez M, Varga R et al. 2004. Accumulation of mutant lamin A causes progressive changes in nuclear architecture in Hutchinson-Gilford progeria syndrome. *Proceedings of the National Academy of Sciences of the United States of America* 101: 8963-8968.

Gonzalez-Suarez I, Redwood A B, Perkins S M, Vermolen B, Lichtensztejin D, Grotsky D A, Morgado-Palacin L, Gapud E J, Sleckman B P, Sullivan T et al. 2009. Novel roles for A-type lamins in telomere biology and the DNA damage response pathway. *EMBO J* 28: 2414-2427.

Guelen L, Pagie L, Brasset E, Meuleman W, Faza M B, Talhout W, Eussen B H, de Klein A, Wessels L, de Laat W et al. 2008. Domain organization of human chromosomes revealed by mapping of nuclear lamina interactions. *Nature* 453: 948-951.

Guzy R D, Sharma B, Bell E, Chandel N S, Schumacker P T. 2008. Loss of the SdhB, but Not the SdhA, subunit of complex II triggers reactive oxygen species-dependent hypoxia-inducible factor activation and tumorigenesis. *Molecular and cellular biology* 28: 718-731.

Hagen T M, Yowe D L, Bartholomew J C, Wehr C M, Do K L, Park J Y, Ames B N. 1997. Mitochondrial decay in hepatocytes from old rats: membrane potential declines, heterogeneity and oxidants increase. *Proceedings of the National Academy of Sciences of the United States of America* 94: 3064-3069.

Hallstrom T C, Mori S, Nevins J R. 2008. An E2F1-dependent gene expression program that determines the balance between proliferation and cell death. *Cancer cell* 13: 11-22.

Hanson G T, Aggeler R, Oglesbee D, Cannon M, Capaldi R A, Tsien R Y, Remington S J. 2004. Investigating mitochondrial redox potential with redox-sensitive green fluorescent protein indicators. *The Journal of biological chemistry* 279: 13044-13053.

Harley C B, Futcher A B, Greider C W. 1990. Telomeres shorten during ageing of human fibroblasts. *Nature* 345: 458-460.

Havens C G, Ho A, Yoshioka N, Dowdy S F. 2006. Regulation of late G1/S phase transition and APC Cdh1 by reactive oxygen species. *Molecular and cellular biology* 26: 4701-4711.

Huang S, Risques R A, Martin G M, Rabinovitch P S, Oshima J. 2008. Accelerated telomere shortening and replicative senescence in human fibroblasts overexpressing mutant and wild-type lamin A. *Experimental cell research* 314: 82-91.

Hussain S P, Amstad P, He P, Robles A, Lupold S, Kaneko I, Ichimiya M, Sengupta S, Mechanic L, Okamura S et al. 2004. p53-induced up-regulation of MnSOD and GPx but not catalase increases oxidative stress and apoptosis. *Cancer research* 64: 2350-2356.

Ibarra A, Schwob E, Mendez J. 2008. Excess MCM proteins protect human cells from replicative stress by licensing backup origins of replication. *Proceedings of the National Academy of Sciences of the United States of America* 105: 8956-8961.

Johnson B R, Nitta R T, Frock R L, Mounkes L, Barbie D A, Stewart C L, Harlow E, Kennedy B K. 2004. A-type lamins regulate retinoblastoma protein function by promoting subnuclear localization and preventing proteasomal degradation. *Proceedings of the National Academy of Sciences of the United States of America* 101: 9677-9682.

Jones N C. 1990. Transformation by the human adenoviruses. *Semin Cancer Biol* 1: 425-435.

Kandert S, Luke Y, Kleinhenz T, Neumann S, Lu W, Jaeger V M, Munck M, Wehnert M, Muller C R, Zhou Z et al. 2007. Nesprin-2 giant safeguards nuclear envelope architecture in LMNA S143F progeria cells. *Hum Mol Genet.* 16: 2944-2959.

Kandert S, Wehnert M, Muller C R, Buendia B, Dabauvalle M C. 2009. Impaired nuclear functions lead to increased senescence and inefficient differentiation in human myoblasts with a dominant p.R545c mutation in the LMNA gene. *European journal of cell biology* 88: 593-608.

Kapinos L E, Schumacher J, Mucke N, Machaidze G, Burkhard P, Aebi U, Strelkov S V, Herrmann H. 2010. Characterization of the head-to-tail overlap complexes formed by human lamin A, B1 and B2 "halfminilamin" dimers. *J Mol Biol* 396: 719-731.

Kennedy B K, Barbie D A, Classon M, Dyson N, Harlow E. 2000. Nuclear organization of DNA replication in primary mammalian cells. *Genes Dev* 14: 2855-2868.

Kosak S T, Skok J A, Medina K L, Riblet R, Le Beau M M, Fisher A G, Singh H. 2002. Subnuclear compartmentalization of immunoglobulin loci during lymphocyte development. *Science* 296: 158-162.

Kumaran R I, Spector D L. 2008. A genetic locus targeted to the nuclear periphery in living cells maintains its transcriptional competence. *J Cell Biol* 180: 51-65.

Laemmli U K. 1970. Cleavage of structural proteins during the assembly of the head of bacteriophage T4. *Nature* 227: 680-685.

Lebedeva M A, Eaton J S, Shadel G S. 2009. Loss of p53 causes mitochondrial DNA depletion and altered mitochondrial reactive oxygen species homeostasis. *Biochim Biophys Acta* 1787: 328-334.

Lee S J, Hwang A B, Kenyon C. 2010. Inhibition of respiration extends C. elegans life span via reactive oxygen species that increase HIF-1 activity. *Curr Biol* 20: 2131-2136.

Liu G H, Barkho B Z, Ruiz S, Diep D, Qu J, Yang S L, Panopoulos A D, Suzuki K, Kurian L, Walsh C et al. 2011. Recapitulation of premature ageing with iPSCs from Hutchinson-Gilford progeria syndrome. *Nature* 472: 221-225.

Macip S, Igarashi M, Fang L, Chen A, Pan Z Q, Lee S W, Aaronson S A. 2002 Inhibition of p21-mediated ROS accumulation can rescue p21-induced senescence. *EMBO J.* 21: 2180-2188.

Malhas A N, Lee C F, Vaux D J. 2009. Lamin B1 controls oxidative stress responses via Oct.-1. *J Cell Biol* 184:45-55.

Mancini M A, Shan B, Nickerson J A, Penman S, Lee W H. 1994. The retinoblastoma gene product is a cell cycle-dependent, nuclear matrix-associated protein. *Proceedings of the National Academy of Sciences of the United States of America* 91: 418-422.

Maske C P, Hollinshead M S, Higbee N C, Bergo M O, Young S G, Vaux D J. 2003. A carboxyl-terminal interaction of lamin B1 is dependent on the CAAX endoprotease Rce1 and carboxymethylation. *J Cell Biol* 162: 1223-1232.

Matoba S, Kang J G, Patino W D, Wragg A, Boehm M, Gavrilova O, Hurley P J, Bunz F, Hwang P M. 2006. p53 regulates mitochondrial respiration. *Science* 312: 1650-1653.

McClintock D, Gordon L B, Djabali K. 2006. Hutchinson-Gilford progeria mutant lamin A primarily targets human vascular cells as detected by an anti-Lamin A G608G antibody. *Proceedings of the National Academy of Sciences of the United States of America* 103: 2154-2159.

McClintock D, Ratner D, Lokuge M, Owens D M, Gordon L B, Collins F S, Djabali K. 2007. The mutant form of lamin A that causes Hutchinson-Gilford progeria is a biomarker of cellular aging in human skin. PloS one 2: e1269.

Meaburn K J, Cabuy E, Bonne G, Levy N, Morris G E, Novelli G, Kill I R, Bridger J M. 2007. Primary laminopathy fibroblasts display altered genome organization and apoptosis. *Aging cell.*

Moir R D, Montag-Lowy M, Goldman R D. 1994. Dynamic properties of nuclear lamins: lamin B is associated with sites of DNA replication. *J Cell Biol* 125: 1201-1212.

Moir R D, Spann T P, Goldman R D. 1995. The dynamic properties and possible functions of nuclear lamins. *Int Rev Cytol:* 141-182.

Moir R D, Spann T P, Herrmann H, Goldman R D. 2000a. Disruption of nuclear lamin organization blocks the elongation phase of DNA replication. *J Cell Biol* 149: 1179-1192.

Moir R D, Yoon M, Khuon S, Goldman R D. 2000b. Nuclear Lamins A and B1. Different pathways of assembly during nuclear envelope formation in living cells. *J Cell Biol* 151: 1155-1168.

Moiseeva O, Bourdeau V, Vernier M, Dabauvalle M C, Ferbeyre G. 2011. Retinoblastoma-independent regulation of cell proliferation and senescence by the p53-p21 axis in lamin A/C-depleted cells. *Aging cell* 10: 789-797.

Mounkes L, Kozlov S, Burke B, Stewart C L. 2003. The laminopathies: nuclear structure meets disease. *Curr Opin Genet Dev* 13: 223-230.

Narita M, Krizhanovsky V, Nunez S, Chicas A, Hearn S A, Myers M P, Lowe S W. 2006. A novel role for highmobility group a proteins in cellular senescence and heterochromatin formation. *Cell* 126: 503-514.

Narita M, Nunez S, Heard E, Lin A W, Hearn S A, Spector D L, Hannon G J, Lowe S W. 2003. Rb-mediated heterochromatin formation and silencing of E2F target genes during cellular senescence. *Cell* 113: 703-716.

Nitta R T, Jameson S A, Kudlow B A, Conlan L A, Kennedy B K. 2006. Stabilization of the retinoblastoma protein by A-type nuclear lamins is required for INK4A-mediated cell cycle arrest. *Molecular and cellular biology* 26: 5360-5372.

Packer L, Fuehr K. 1977. Low oxygen concentration extends the lifespan of cultured human diploid cells. *Nature* 267: 423-425.

Parrinello S, Samper E, Krtolica A, Goldstein J, Melov S, Campisi J. 2003. Oxygen sensitivity severely limits the replicative lifespan of murine fibroblasts. *Nat Cell Biol* 5: 741-747.

Passos J F, Nelson G, Wang C, Richter T, Simillion C, Proctor C J, Miwa S, Olijslagers S, Hallinan J, Wipat A et al. 2010. Feedback between p21 and reactive oxygen production is necessary for cell senescence. *Mol Syst Biol* 6: 347.

Pekovic V, Harborth J, Broers J L, Ramaekers F C, van Engelen B, Lammens M, von Zglinicki T, Foisner R, Hutchison C, Markiewicz E. 2007. Nucleoplasmic LAP2{alpha}-lamin A complexes are required to maintain a proliferative state in human fibroblasts. *J Cell Biol* 176: 163-172.

Polager S, Ginsberg D. 2009. p53 and E2f: partners in life and death. *Nat Rev Cancer* 9: 738 748.

Ragnauth C D, Warren D T, Liu Y, McNair R, Tajsic T, Figg N, Shroff R, Skepper J, Shanahan C M. 2010. Prelamin A acts to accelerate smooth muscle cell senescence and is a novel biomarker of human vascular aging. *Circulation* 121: 2200-2210.

Rheinwald J G, Hahn W C, Ramsey M R, Wu J Y, Guo Z, Tsao H, De Luca M, Catricala C, O'Toole K M. 2002. A two-stage, p16(INK4A)- and p53-dependent keratinocyte senescence mechanism that limits replicative potential independent of telomere status. *Molecular and cellular biology* 22: 5157-5172.

Rodier F, Munoz D P, Teachenor R, Chu V, Le O, Bhaumik D, Coppe J P, Campeau E, Beausejour C M, Kim S H et al. 2011. DNA-SCARS: distinct nuclear structures that sustain damage-induced senescence growth arrest and inflammatory cytokine secretion. *J Cell Sci* 124: 68-81.

Rodriguez J, Calvo F, Gonzalez J M, Casar B, Andres V, Crespo P. 2010. ERK1/2 MAP kinases promote cell cycle entry by rapid, kinase-independent disruption of retinoblastoma-lamin A complexes. *J Cell Biol* 191: 967-979.

Rodriguez S, Coppede F, Sagelius H, Eriksson M. 2009. Increased expression of the Hutchinson-Gilford progeria syndrome truncated lamin A transcript during cell aging. *European journal of human genetics: EJHG* 17: 928-937.

Sablina A A, Budanov A V, Ilyinskaya G V, Agapova L S, Kravchenko J E, Chumakov P M. 2005. The antioxidant function of the p53 tumor suppressor. *Nature medicine* 11: 1306-1313.

Sahin E, Colla S, Liesa M, Moslehi J, Muller F L, Guo M, Cooper M, Kotton D, Fabian A J, Walkey C et al. 2011. Telomere dysfunction induces metabolic and mitochondrial compromise. *Nature* 470: 359-365.

Scaffidi P, Misteli T. 2005. Reversal of the cellular phenotype in the premature aging disease Hutchinson-Gilford progeria syndrome. *Nature medicine* 11: 440-445.

Scaffidi P, Misteli T. 2006. Lamin A-dependent nuclear defects in human aging. *Science* 312: 1059-1063.

Schefe J H, Lehmann K E, Buschmann I R, Unger T, Funke-Kaiser H. 2006. Quantitative real-time RT-PCR data analysis: current concepts and the novel "gene expression's CT difference" formula. *J Mol Med* 84: 901-910.

Schermelleh L, Carlton P M, Haase S, Shao L, Winoto L, Kner P, Burke B, Cardoso M C, Agard D A, Gustafsson M G et al. 2008. Subdiffraction multicolor imaging of the nuclear periphery with 3D structured illumination microscopy. *Science* 320: 1332-1336.

Sebti S M. 2005. Protein farnesylation: implications for normal physiology, malignant transformation, and cancer therapy. *Cancer cell* 7: 297-300.

Sekharam M, Trotti A, Cunnick J M, Wu J. 1998. Suppression of fibroblast cell cycle progression in G1 phase by N-acetylcysteine. *Toxicology and applied pharmacology* 149: 210-216.

Serrano M, Lin A W, McCurrach M E, Beach D, Lowe S W. 1997. Oncogenic ras provokes premature cell senescence associated with accumulation of p53 and p16INK4a. *Cell* 88: 593-602.

Shaulian E, Zauberman A, Ginsberg D, Oren M. 1992. Identification of a minimal transforming domain of p53: negative dominance through abrogation of sequence-specific DNA binding. *Molecular and cellular biology* 12: 5581-5592.

Shimi T, Pfleghaar K, Kojima S, Pack C, Solovei I, Goldman A E, Adam S A, Shumaker D K, Kinjo M, Cremer T et al. 2008. The A- and B-type Nuclear Lamin Networks: Microdomains Involved in Chromatin Organization and Transcription. *Genes Dev* 22: 3409-3421.

Shumaker D K, Solimando L, Sengupta K, Shimi T, Adam S A, Grunwald A, Strelkov S V, Aebi U, Cardoso M C, Goldman R D. 2008. The Highly Conserved Nuclear Lamin Ig-fold Binds to PCNA: Its Role in DNA Replication. *J Cell Biol* 181: 269-280.

Spanier G, Xu H, Xia N, Tobias S, Deng S, Wojnowski L, Forstermann U, Li H. 2009. Resveratrol reduces endothelial oxidative stress by modulating the gene expression of superoxide dismutase 1 (SOD1), glutathione peroxidase 1 (GPx1) and NADPH oxidase subunit (Nox4). *J Physiol Pharmacol* 60 Suppl 4:111-116.

Spann T P, Goldman A E, Wang C, Huang S, Goldman R D. 2002. Alteration of nuclear lamin organization inhibits RNA polymerase II-dependent transcription. *J Cell Biol* 156: 603-608.

Spann T P, Moir R D, Goldman A E, Stick R, Goldman R D. 1997. Disruption of nuclear lamin organization alters the distribution of replication factors and inhibits DNA synthesis. *J Cell Biol* 136: 1201-1212.

Sullivan T, Escalante-Alcalde D, Bhatt H, Anver M, Bhat N, Nagashima K, Stewart C L, Burke B. 1999. Loss of A-type lamin expression compromises nuclear envelope integrity leading to muscular dystrophy. *J Cell Biol* 147: 913-920.

Taimen P, Pfleghaar K, Shimi T, Moller D, Ben-Harush K, Erdos M R, Adam S A, Herrmann H, Medalia O, Collins F S et al. 2009. A progeria mutation reveals functions for lamin A in nuclear assembly, architecture, and chromosome organization. *Proceedings of the National Academy of Sciences of the United States of America* 106: 20788-20793.

Ukekawa R, Miki K, Fujii M, Hirano H, Ayusawa D. 2007. Accumulation of multiple forms of lamin A with down-regulation of FACE-1 suppresses growth in senescent human cells. *Genes to cells: devoted to molecular & cellular mechanisms* 12: 397-406.

Varani J, Bhagavathula N, Nerusu K C, Sherzer H, Fay K, Boitano A E, Glick G D, Johnson K, Kang S, Opipari A W, Jr. 2005. A novel benzodiazepine selectively inhibits keratinocyte proliferation and reduces retinoid-induced epidermal hyperplasia in organ-cultured human skin. *The Journal of pharmacology and experimental therapeutics* 313: 56-63.

Vergnes L, Peterfy M, Bergo M O, Young S G, Reue K. 2004. Lamin B1 is required for mouse development and nuclear integrity. *Proceedings of the National Academy of Sciences of the United States of America* 101: 10428-10433.

Weinberg F, Hamanaka R, Wheaton W W, Weinberg S, Joseph J, Lopez M, Kalyanaraman B, Mutlu G M, Budinger G R, Chandel N S. 2010. Mitochondrial metabolism and ROS generation are essential for Kras-mediated tumorigenicity. *Proceedings of the National Academy of Sciences of the United States of America* 107: 8788-8793.

Wright W E, Shay J W. 2001. Cellular senescence as a tumor-protection mechanism: the essential role of counting. *Curr Opin Genet Dev* 11:98-103.

Yang S H, Chang S Y, Yin L, Tu Y, Hu Y, Yoshinaga Y, de Jong P J, Fong L G, Young S G. 2011. An absence of both lamin B1 and lamin B2 in keratinocytes has no effect on cell proliferation or the development of skin and hair. *Hum Mol Genet.* 20: 3537-3544.

Yang W, Hekimi S. 2010. A mitochondrial superoxide signal triggers increased longevity in *Caenorhabditis elegans*. *PLoS biology* 8: e1000556.

Yuan J S, Reed A, Chen F, Stewart C N, Jr. 2006. Statistical analysis of real-time PCR data. *BMC Bioinformatics* 7: 85.

The invention claimed is:

1. A method comprising:

(a) contacting a population of chemically-fixed human cells comprising both proliferating and senescent cells with non-human antibodies that specifically bind human lamin B1 (anti-LB 1 antibodies) under conditions which result in formation of a complex between the anti-LB 1 antibodies and human lamin B1 present on cells within the population, wherein said anti-LB 1 antibodies bind to lamin B1, but not to Lamin B2 and Lamin A/C;

(b) binding fluorophore-tagged secondary antibodies to said anti-LB 1 antibodies; and (c) detecting fluorescence from said fluorophore.

* * * * *